United States Patent
Geho et al.

(10) Patent No.: US 10,751,418 B2
(45) Date of Patent: Aug. 25, 2020

(54) ORALLY BIOAVAILABLE LIPID-BASED CONSTRUCTS

(71) Applicant: SDG, Inc., Cleveland, OH (US)

(72) Inventors: W. Blair Geho, Wooster, OH (US); John R. Lau, Howard, OH (US)

(73) Assignee: SDG, Inc., Cleveland, OH (US)

( * ) Notice: Subject to any disclaimer, the term of this patent is extended or adjusted under 35 U.S.C. 154(b) by 341 days.

(21) Appl. No.: 13/785,591

(22) Filed: Mar. 5, 2013

(65) Prior Publication Data

US 2013/0183270 A1 Jul. 18, 2013

Related U.S. Application Data

(63) Continuation of application No. 12/413,293, filed on Mar. 27, 2009, now abandoned, which is a
(Continued)

(51) Int. Cl.
*A61K 47/44* (2017.01)
*A61K 9/48* (2006.01)
*A61K 9/107* (2006.01)
*A61K 38/26* (2006.01)
*A61K 38/23* (2006.01)
(Continued)

(52) U.S. Cl.
CPC ............ *A61K 47/44* (2013.01); *A61K 9/1075* (2013.01); *A61K 9/4858* (2013.01); *A61K 9/4866* (2013.01); *A61K 31/405* (2013.01); *A61K 38/23* (2013.01); *A61K 38/26* (2013.01);
(Continued)

(58) Field of Classification Search
CPC .................................. A61K 9/167; A61K 4/47
See application file for complete search history.

(56) References Cited

U.S. PATENT DOCUMENTS

| 4,501,728 A | 2/1985 | Geho et al. |
| 4,603,044 A | 7/1986 | Geho et al. |

(Continued)

FOREIGN PATENT DOCUMENTS

| CN | 1274605 A | 11/2000 |
| CN | 1895224 A | 1/2007 |

(Continued)

OTHER PUBLICATIONS

Ansell et al. (2000). "4: Antibody Conjugation Methods for Active Targeting of Liposomes." Methods in Molecular Medicine, vol. 25: Drug Targeting: Strategies, Principles, and Applications. Ed. G. E. Francis and C. Delgado. Totowa: Humana Press, 2000. 51-67.*

(Continued)

*Primary Examiner* — Benjamin J Packard
(74) *Attorney, Agent, or Firm* — Saul Ewing Arnstein & Lehr LLP; Kathryn Doyle; Domingos J. Silva

(57) ABSTRACT

The present invention is embodied by a composition capable of chaperoning a typically non-orally available therapeutic or diagnostic agent through the environment of the digestive tract such that the therapeutic or diagnostic agent is bioavailable. The composition may or may not be targeted to specific cellular receptors, such as hepatocytes. Therapeutic agents include, but are not limited to, insulin, calcitonin, serotonin, and other proteins. Targeting is accomplished with biotin or metal based targeting agents.

9 Claims, 14 Drawing Sheets

Related U.S. Application Data continuation of application No. PCT/US2008/077990, filed on Sep. 26, 2008, which is a continuation of application No. 11/904,937, filed on Sep. 28, 2007.

(51) Int. Cl.
   *A61K 38/28* (2006.01)
   *A61K 31/405* (2006.01)
   *A61K 9/20* (2006.01)

(52) U.S. Cl.
   CPC ............ *A61K 38/28* (2013.01); *A61K 9/2013* (2013.01); *A61K 9/2063* (2013.01)

(56) References Cited

U.S. PATENT DOCUMENTS

| | | | |
|---|---|---|---|
| 4,740,375 A | 4/1988 | Geho et al. | |
| 4,946,787 A | 8/1990 | Eppstein et al. | |
| 5,000,960 A * | 3/1991 | Wallach | A61K 9/1272 264/4.3 |
| 5,019,369 A * | 5/1991 | Presant | A61K 9/1271 424/1.21 |
| 5,104,661 A | 4/1992 | Lau | |
| 5,120,710 A * | 6/1992 | Liedtke | A61K 9/485 424/85.4 |
| 5,399,331 A * | 3/1995 | Loughrey | A61K 9/1271 424/417 |
| 5,411,730 A | 5/1995 | Kirpotin et al. | |
| 5,514,670 A * | 5/1996 | Friedman | A61K 9/006 424/185.1 |
| 5,567,432 A | 10/1996 | Lau et al. | |
| 5,795,895 A | 8/1998 | Anchors | |
| 5,968,972 A * | 10/1999 | Broder | A61K 38/13 514/15.4 |
| 6,063,400 A | 5/2000 | Geho et al. | |
| 6,177,099 B1 | 1/2001 | Lau et al. | |
| 6,365,156 B1 | 4/2002 | Lee | |
| 6,726,924 B2 | 4/2004 | Keller | |
| 7,169,410 B1 | 1/2007 | Lau et al. | |
| 7,858,116 B2 | 12/2010 | Lau et al. | |
| 7,871,641 B2 | 1/2011 | Lau et al. | |
| 8,962,015 B2 | 2/2015 | Lau et al. | |
| 2002/0039595 A1 | 4/2002 | Keller et al. | |
| 2003/0133972 A1 | 7/2003 | Danthi et al. | |
| 2004/0016035 A1 | 1/2004 | Floyd | |
| 2005/0026826 A1 | 2/2005 | Hoenig | |
| 2005/0059100 A1 | 3/2005 | Meares et al. | |
| 2006/0008461 A1 | 1/2006 | Yatvin et al. | |
| 2006/0009381 A1 | 1/2006 | Reutelingsperger | |
| 2006/0141047 A1 | 6/2006 | Heller et al. | |
| 2006/0222697 A1 | 10/2006 | Lau et al. | |
| 2006/0222698 A1 | 10/2006 | Lau et al. | |
| 2007/0104777 A1 | 5/2007 | Lau et al. | |
| 2007/0218117 A1 | 9/2007 | Lau et al. | |
| 2007/0281325 A1 | 12/2007 | Danielzadeh | |
| 2008/0014255 A1 | 1/2008 | Tagawa et al. | |
| 2008/0050372 A1 | 2/2008 | Grunberger et al. | |
| 2008/0305156 A1 | 12/2008 | Laing et al. | |
| 2009/0042945 A1 | 4/2009 | Frank et al. | |
| 2009/0087479 A1 | 4/2009 | Lau et al. | |
| 2009/0185976 A1 * | 7/2009 | See | A61K 9/127 424/9.1 |
| 2011/0135725 A1 | 6/2011 | Lau et al. | |
| 2015/0125518 A1 | 5/2015 | Lau et al. | |

FOREIGN PATENT DOCUMENTS

| | | |
|---|---|---|
| EP | 0577146 A2 | 1/1994 |
| JP | H11116478 A | 4/1999 |
| WO | 85/03640 A1 | 8/1985 |
| WO | 87/01587 A1 | 3/1987 |
| WO | 1996010585 A1 | 4/1996 |
| WO | 1999059545 A1 | 11/1999 |
| WO | 0032167 A1 | 6/2000 |
| WO | 2006127361 A2 | 11/2006 |
| WO | 2009042945 A1 | 4/2009 |
| WO | 2009045873 | 4/2009 |

OTHER PUBLICATIONS

Iwanaga et al (International Journal of Pharmaceutics 157 (1997) 73-80). (Year: 1997).*

Ansell, S.M. et al., "3-(2-Pyridyldithio)propionic Acid Hydrazide as a Cross-Linker in the Formation of Liposome—Antibody Conjugates," Bioconjugate Chem., 1996, vol. 7, No. 4, pp. 490-496.

Cantenys, D. et al., "Covalent Attachment of Insulin to the Outer Surface of Liposomes," Biochemical and Biophysical Research Communications, 1983, vol. 117, No. 2, pp. 399-405.

Dong, C. et al., "Acacia-Gelatin Microencapsulated Liposomes: Preparation, Stability, and Release of Acetylsalicylic Acid," 1993, Pharmaceutical Research, vol. 10, No. 1, pp. 141-146.

Erion, M.D. et al., "Targeting Thyroid Hormone Receptor-b Agonists to the Liver Reduces Cholesterol and Triglycerides and Improves the Therapeutic Index," PNAS, 2007, vol. 104, No. 39, pp. 15490-15495.

Hermanson, G.T., "Heterobifunctional Crosslinkers," Bioconjugate Techniques, 2008, Elsevier, XP-002738503.

Manjappa, A.S. et al., "Antibody Derivatization and Conjugation Strategies: Application in Preparation of Stealth Immunoliposome to Target Chemotherapeutics to Tumor," Journal of Controlled Release, 2011, vol. 150, No. 1, pp. 2-22.

Takeoka, S. et al., "Rolling Properties of rGPIba-conjugated Phospholipid Vesicles with Different Membrane Flexibilities on vWf Surface Under Flow Conditions," Biochemical and Biophysical Research Communications, 2002, vol. 296, pp. 765-770.

Walde, P. et al., "Enzymes Inside Lipid Veiscles: Preparation, Reactivity and Applications," 2001, Biomolecular Engineering, vol. 18, pp. 143-177.

* cited by examiner

ORALLY BIOAVAILABLE LIPID-BASED CONSTRUCTS

CROSS-REFERENCE TO RELATED APPLICATIONS

The present application is a continuation of, and claims priority to, U.S. application Ser. No. 12/413,293, filed Mar. 27, 2009, which is a continuation-in-part of, and claims priority to, International Application No. PCT/US2008/077990, filed Sep. 26, 2008, and published under PCT Article 21(2) in English, which is a continuation-in-part of, and claims priority to U.S. application Ser. No. 11/904,937, filed Sep. 28, 2007, all of which applications are hereby incorporated by reference in their entireties herein.

BACKGROUND OF THE INVENTION

One of the most preferred ways to deliver a pharmaceutical to a subject is in an oral formulation. However, oral formulations of many pharmaceutical compounds are often unavailable due to the pharmaceutical's incompatibility with the harsh environment of the digestive tract. This is particularly true for pharmaceutical compounds such as peptides, proteins, certain small molecules, and nucleic acids. Representative examples include calcitonin, serotonin, parathyroid hormone, GLP-1, erythropoietin, interferon of various types, human growth hormone, monoclonal antibodies, and many others, the utilities of which have been extensively reviewed in the literature.

Thus, what is needed in the field of oral drug delivery is a composition that enables oral delivery of a wide range of pharmaceutical products and other therapeutic agents. The present invention meets and addresses this need.

BRIEF SUMMARY OF THE INVENTION

The present invention includes compositions that facilitate and/or enable absorption of therapeutics which are not typically orally bioavailable. In one embodiment, a composition of the invention functions by associating with a therapeutic agent and chaperoning or escorting the therapeutic agent through the lumen of the gut into the portal blood flow and finally on to the systemic circulation. In certain embodiments, the composition of the invention possesses many unique and advantageous properties. One of these properties is the ability to insert into intercellular gaps and pass through the mammalian gut into the portal circulation. In certain embodiments, a composition of the invention may be targeted to specific cellular or extracellular receptors via one or more targeting agents. As an alternative to incorporation of a targeting agent, or optionally in addition to a targeting agent, a composition of the invention may further include one or more RES masking agents.

In a typical embodiment, an orally bioavailable composition of the invention comprises various lipid-based constituents, at least one therapeutic or diagnostic agent, an optional targeting agent, and/or an optional RES masking agent.

The various lipid-based constituents include, but are not limited to, dynamically sized liposomes, dynamically sized liposome fragments, and dynamically sized lipid particles. A lipid particle comprises at least one, but preferably more than one, molecule of a single lipid. A liposome or liposome fragment comprise at least two structurally unique lipid molecules. These lipid-based constituents may be formed when lipids are combined according to the procedures set forth herein.

In certain embodiments, the lipids are selected from the group consisting of MPB-PE, MCC-PE, 1,2-distearoyl-sn-glycero-3-phosphocholine, 1,2-dipalmitoyl-sn-glycero-3-phosphocholine, 1,2-dimyristoyl-sn-glycero-3-phosphocholine, cholesterol, cholesterol oleate, dihexadecyl phosphate, 1,2-distearoyl-sn-glycero-3-phosphate, 1,2-dipalmitoyl-sn-glycero-3-phosphate, 1,2-dimyristoyl-sn-glycero-3-phosphate, 1,2-distearoyl-sn-glycero-3-phosphoethanolamine, 1,2-dipalmitoyl-sn-glycero-3-phosphoethanolamine, 1,2-dimyristoyl-sn-glycero-3-phosphoethanolamine, 1,2-dipalmitoyl-sn-glycero-3-phospho-2-mercaptoethanol, 1,2-dipalmitoyl-sn-glycero-3-phosphoethanolamine-N-(succinyl), 1,2-dipalmitoyl-sn-glycero-3-[phospho-rac-(1-glycerol)] (sodium salt), and triethylammonium 2,3-diacetoxypropyl 2-(5-((3aS,6aR)-2-oxohexahydro-1H-thieno[3,4-d]imidazol-4-yl)pentanamido)ethyl phosphate.

In certain embodiments, the therapeutic agent is selected from the group consisting of insulin, interferon, erythropoietin, parathyroid hormone, calcitonin, serotonin, rituximab, trastuzumab, uricase, tissue plasminogen activator, thymoglobin, a vaccine, heparin or a heparin analog, antithrombin, III, filgrastin, pramilitide acetate, exanatide, epifibatide, antivenins, IgG, IgM, HGH, thyroxine, GLP-1, blood clotting Factors VII, VIII, IX, Kallikrein, Kininogen, Hageman Factor (XII), plasma thromboplastin antecedent Factor (XI), tissue factor, Stuart Factor (X), accelerin (V), prothrombin (II), and fibrin stabilizing Factor (XIII); a monoclonal antibody, and glycolipids that act as therapeutic agents.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

DETAILED DESCRIPTION OF THE INVENTION

Figure 1:
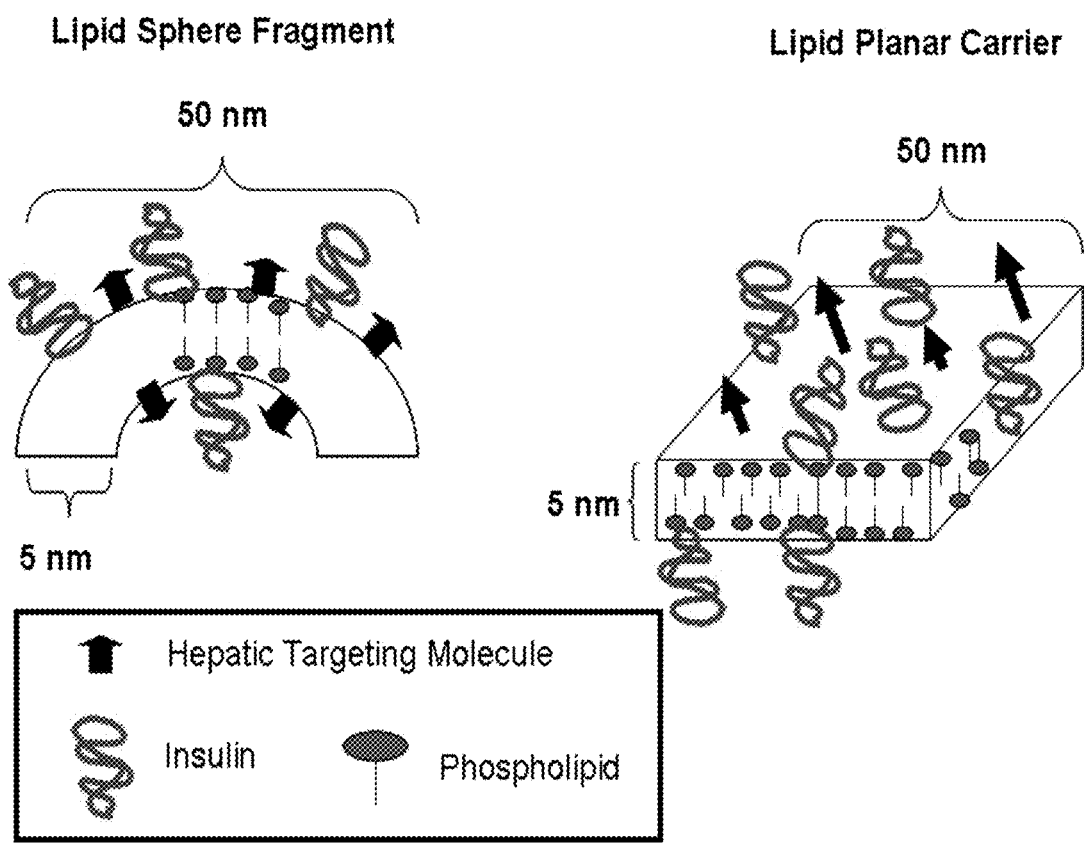
FIG. 1 is a schematic representation of a composition of the invention.

The present invention includes compositions that facilitate and/or enable absorption of therapeutics which are not typically orally bioavailable. The compounds of the present invention may further act to enhance the oral bioavailability of compounds that are already orally bioavailable. In one embodiment, a composition of the invention functions by associating with a therapeutic agent and chaperoning the therapeutic agent through the lumen of the gut into the portal blood flow and finally on to the systemic circulation. The composition of the invention possess many unique and advantageous properties. One of these properties is the ability to insert into intercellular gaps and pass through the mammalian gut into the portal circulation. In certain embodiments, a composition of the invention may be targeted to specific cellular or extracellular receptors via one or more targeting agents. As an alternative to incorporation of a targeting agent, or optionally in addition to a targeting agent, a composition of the invention may further include one or more reticuloendothelial system ("RES") masking agents.

Although the present invention bears some resemblance to the composition disclosed in PCT/US06/19119, U.S. patent application Ser. No. 11/904,937, and PCT/US08/77990, the compositions of the present invention may be differentiated from all three applications. The present invention may be differentiated from PCT/U06/19119 by the size of the composition as well as the use of covalent linkages to tether a given therapeutic agent. The present invention may be differentiated from PCT/US08/77990 and Ser. No. 11/904,937 by the chemical structure of the linker used to link a given therapeutic agent to the composition. The present invention may be further differentiated from U.S. patent application Ser. No. 11/904,937 and PCT/US08/77990 by the therapeutic agent associated with the composition.

In a typical embodiment, an orally bioavailable composition of the invention comprises various lipid-based constituents, at least one therapeutic or diagnostic agent, an optional targeting agent, and/or an optional RES masking agent.

Definitions

Unless defined otherwise, all technical and scientific terms used herein generally have the same meaning as commonly understood by one of ordinary skill in the art to which the invention belongs. Generally, the nomenclature used herein and the laboratory procedures in organic chemistry and protein chemistry are those well known and commonly employed in the art.

The articles "a" and "an" are used herein to refer to one or to more than one (i.e. to at least one) of the grammatical object of the article. By way of example, "an element" means one element or more than one element.

As used herein, amino acids are represented by the full name thereof, by the three-letter code as well as the one-letter code corresponding thereto, as indicated in the following table:

| Full Name | 3 Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "lower", when used in reference to a chemical structure, describes a group containing from 1 to 6 carbon atoms.

The term "alkyl", by itself or as part of another substituent means, unless otherwise stated, a straight, branched or cyclic hydrocarbon having the number of carbon atoms designated (i.e. $C_1$-$C_6$ means one to six carbons). Examples include: methyl, ethyl, propyl, isopropyl, butyl, isobutyl, tert-butyl, pentyl, neopentyl, hexyl, cyclohexyl and cyclopropylmethyl. Most preferred is ($C_1$-$C_3$)alkyl, particularly ethyl, methyl and isopropyl.

The term "alkylene", by itself or as part of another substituent means, unless otherwise stated, a straight, branched or cyclic chain hydrocarbon having two substitution sites, e.g., methylene (—$CH_2$—), ethylene (—$CH_2CH_2$—), isopropylene (—$C(CH_3)$═CH—), etc.

The term "aryl", employed alone or in combination with other terms, means, unless otherwise stated, a carbocyclic structure, with or without saturation, containing one or more rings (typically one, two or three rings) wherein said rings may be attached together in a pendant manner, such as a biphenyl, or may be fused, such as naphthalene. Examples include phenyl, anthracyl, and naphthyl. The structure may be optionally substituted with one or more substituents, independently selected from halogen; ($C_1$-$C_6$)alkyl; ($C_1$-$C_6$) alkenyl; ($C_1$-$C_6$)alkoxy; OH; $NO_2$; C≡N; C(═O)O($C_1$-$C_3$) alkyl; ($C_2$-$C_6$)alkylene-$OR^2$; phosphonato; $NR^2{}_2$; NHC (═O)($C_1$-$C_6$)alkyl; sulfamyl; carbamyl; OC(═O)($C_1$-$C_3$) alkyl; O($C_2$-$C_6$)alkylene-N(($C_1$-$C_6$)alkyl)$_2$; and ($C_1$-$C_3$) perfluoroalkyl.

The term "arylloweralkyl" means a functional group wherein an aryl group is attached to a lower alkylene group, e.g., —CH$_2$CH$_2$-phenyl.

The term "alkoxy" employed alone or in combination with other terms means, unless otherwise stated, an alkyl group or an alkyl group containing a substituent such as a hydroxyl group, having the designated number of carbon atoms connected to the rest of the molecule via an oxygen atom, such as, for example, —OCH(OH)—, —OCH$_2$OH, methoxy (—OCH$_3$), ethoxy (—OCH$_2$CH$_3$), 1-propoxy (—OCH$_2$CH$_2$CH$_3$), 2-propoxy (isopropoxy), butoxy (—OCH$_2$CH$_2$CH$_2$CH$_3$), pentoxy (—OCH$_2$CH$_2$CH$_2$CH$_2$CH$_3$), and the higher homologs and isomers.

The term "acyl" means a functional group of the general formula —C(=O)—R, wherein —R is hydrogen, alkyl, amino or alkoxy. Examples include acetyl (—C(=O)CH$_3$), propionyl (—C(=O)CH$_2$CH$_3$), benzoyl (—C(=O)C$_6$H$_5$), phenylacetyl (C(=O)CH$_2$C$_6$H$_5$), carboethoxy (—CO$_2$CH$_2$CH$_3$), and dimethylcarbamoyl (C(=O)N(CH$_3$)$_2$).

The terms "halo" or "halogen" by themselves or as part of another substituent mean, unless otherwise stated, a fluorine, chlorine, bromine, or iodine atom.

The term "heterocycle" or "heterocyclyl" or "heterocyclic" by itself or as part of another substituent means, unless otherwise stated, a saturated or unsaturated, stable, mono or multicyclic ring system comprising carbon atoms and at least one heteroatom selected from the group comprising N, O, and S, and wherein the nitrogen and sulfur heteroatoms may be optionally oxidized, and the nitrogen atom may be optionally quaternized. Examples include pyridine, pyrrole, imidazole, benzimidazole, phthalein, pyridenyl, pyranyl, furanyl, thiazole, thiophene, oxazole, pyrazole, 3-pyrroline, pyrrolidene, pyrimidine, purine, quinoline, isoquinoline, carbazole, etc. Where substitution will result in a stable compounds, the structure may be optionally substituted with one or more substituents, independently selected from halogen; (C$_1$-C$_6$)alkyl; (C$_1$-C$_6$)alkenyl; (C$_1$-C$_6$)alkoxy; OH; NO$_2$; C≡N; C(=O)O(C$_1$-C$_3$)alkyl; (C$_2$-C$_6$)alkylene-OR$^2$; phosphonato; NR$^2$$_2$; NHC(=O)(C$_1$-C$_6$)alkyl; sulfamyl; carbamyl; OC(=O)(C$_1$-C$_3$)alkyl; O(C$_2$-C$_6$)alkylene-N((C$_1$-C$_6$)alkyl)$_2$; and (C$_1$-C$_3$)perfluoroalkyl.

The term "amphipathic lipid" means a lipid molecule having a polar end and a non-polar end.

A "complexing agent" is a compound capable of forming a water insoluble coordination complex with a metal, e.g. a salt of chromium, zirconium, etc., that is substantially insoluble in water and soluble in organic solvents.

"Aqueous media" means media comprising water or media comprising water containing at least one buffer or salt.

The terms "associated," or "associated with," as well as variations thereof, when used in reference to a composition of the invention, means that the referenced material, typically a therapeutic agent, is incorporated (or intercalated) into, or on the surface of, or within a lipid-based constituent comprising the composition of the present invention. Association may, however, refer to the situation wherein the referenced material, typically a therapeutic agent, is covalently attached to a lipid included in one of the various lipid-based constituents comprising the composition of the invention. The applicability of the appropriate definition will be appreciable from the context in which the terms is used.

The term "insulin" refers to natural or recombinant forms of insulin, synthetic insulin, and derivatives of the aforementioned insulins. Examples of insulin include, but are not limited to insulin lispro, insulin aspart, regular insulin, insulin glargine, insulin zinc, human insulin zinc extended, isophane insulin, human buffered regular insulin, insulin glulisine, recombinant human regular insulin, ultralente insulin, humulin, NPH insulin, Levemir, Novolog, and recombinant human insulin isophane. Also included are animal insulins, such as bovine or porcine insulin.

The terms "glargine" and "glargine insulin" both refer to a recombinant human insulin analog which differs from human insulin in that the amino acid asparagine at position A21 is replaced by glycine and two arginines are added to the C-terminus of the B-chain. Chemically, it is 21A-Gly-30Ba-L-Arg-30Bb-L-Arg-human insulin and has the empirical formula C$_{267}$H$_{404}$N$_{72}$O$_{78}$S$_6$ and a molecular weight of 6063.

The term "recombinant human insulin isophane" refers to a human insulin that has been treated with protamine.

The term "bioavailability" refers to a measurement of the rate and extent that a pharmaceutical agent, such as, but not limited to, insulin, reaches the systemic circulation and is available at its site of action.

As used herein, to "treat" means reducing the frequency with which symptoms of a disease, disorder, or adverse condition, and the like, are experienced by a patient.

As used herein, the term "pharmaceutically acceptable carrier" means a chemical composition with which the active ingredient may be combined and which, following the combination, can be used to administer the active ingredient to a subject.

The term "lipid" or "lipids" means an organic compound characterized by its preference for non-polar solvents. A lipid may or may not possess an alkyl tail. Lipids according to the present invention include, but are not limited to, the class of compounds known in the art as phospholipids, cholesterols, and dialkyl phosphates.

As used herein, "cholesterol" means the compound and all derivatives and analogs of the compound:

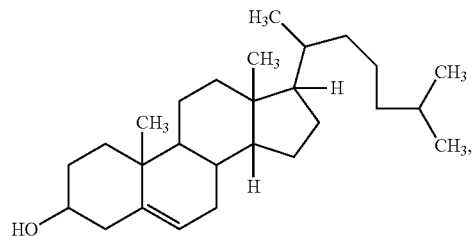 [SMILES: CC(C)CCCC(C)C1CCC2C3CC=C4CC(S)CCC4(C)C3CCC12C]

wherein said derivatives and analogs include, but are not limited to, thiocholesterol:

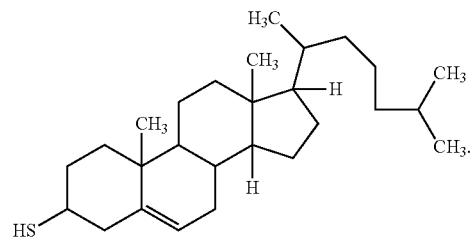

As used herein, "1,2-dipalmitoyl-sn-glycero-3-phospho-2-mercaptoethanol" means the compound having the formula:

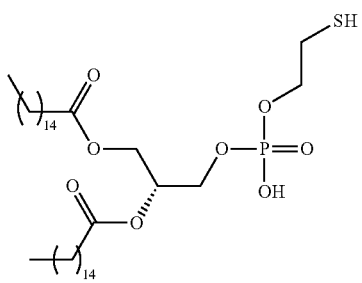

as well as salts thereof.

As used herein, "particle" comprises an agglomeration of multiple units of one or more lipids.

As used herein, "thyroxine" refers to the compound:

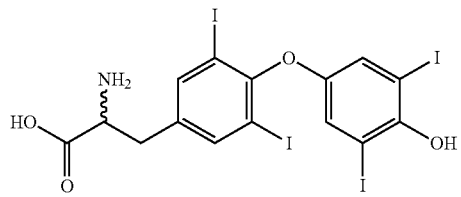 [SMILES: NC(Cc1cc(I)c(Oc2cc(I)c(O)c(I)c2)c(I)c1)C(=O)O]

wherein the amino group may be in either the "D" or "L" configuration.

As used herein, "co-administration" or "co-administering" as well as variations thereof, means administering a second therapeutic agent before, during, or after the administration of a first therapeutic agent. The first and second therapeutic agents may be the same or different.

As used herein, "interferon" refers to all forms of interferon, including, but not limited to, interferon-α, interferon-beta, interferon-gamma, as well as sub-units thereof.

Description

A composition of the present invention is comprised of various lipid-based constituents, at least one therapeutic or diagnostic agent, optionally at least one targeting molecule, and optionally, at least one RES masking agent. A composition of the present invention may further include gelatin as an active component. When present, the gelatin actively reversibly interacts with one or more of the various lipid-based constituents to stabilize the composition of the invention. The at least one therapeutic agent and/or diagnostic agent is associated with a lipid-based constituent comprising the composition of the invention.

The lipid-based constituents comprising a composition of the invention include, but are not limited to, dynamically sized liposomes, dynamically sized liposome fragments, and dynamically sized lipid particles. A lipid particle comprises at least one, but preferably more than one, molecule of a single lipid. A liposome or liposome fragment comprise at least two structurally unique lipid molecules.

Traditionally, liposome, liposome fragments, and lipid particles comprised of amphipathic materials have been limited to a lower size distribution of about 40 nanometers. This limit was believed to be a function of the collective sizes of the constituent lipids (phospholipids, cholesterols, dialkylphosphates, etc.) that constituted the membrane structure.

The lipid-based constituents of a composition of the invention, however, demonstrate heretofore unobserved dynamic sizing and size elasticity. Specifically, these structures exist in a dynamic equilibrium in aqueous media such that, on average, these structures fluctuate in size from about 6 nanometers to about 80 nanometers in diameter, but may reach sizes as large as 200 nanometers. At any given time, anywhere from about 5% to about 50% of the various lipid-based constituents exhibit an average diameter of about 20 nanometers or less. Due to the nearly constant fluctuations in sizes, the lipid-based constituents cannot be physically separated by traditional fractionating means to form discrete populations.

The composition of the invention may associate with one or more therapeutic agents or diagnostic agents. When these associations are non-covalent, and without wishing to be bound by any particular theory, it is believed that a given therapeutic agent is associated with a composition of the invention through various intramolecular forces. It is further believed that when a lipid-based constituent comprising the composition of the invention has a diameter of 20 nanometers or less, it is sufficiently small to pass through intracellular gaps and enable the transport of the associated therapeutic agent from the lumen of the gut into the portal blood flow. Another mechanism of action may, however, account for the observed activity.

Lipids

The lipids comprising the composition of the present invention are selected from the group consisting of 1,2-distearoyl-sn-glycero-3-phosphocholine, 1,2-dipalmitoyl-sn-glycero-3-phosphocholine, 1,2-dimyristoyl-sn-glycero-3-phosphocholine, cholesterol, cholesterol oleate, thiocholesterol, dihexadecyl phosphate, 1,2-distearoyl-sn-glycero-3-phosphate, 1,2-dipalmitoyl-sn-glycero-3-phosphate, 1,2-dimyristoyl-sn-glycero-3-phosphate, 1,2-distearoyl-sn-glycero-3-phosphoethanolamine, 1,2-dipalmitoyl-sn-glycero-3-phosphoethanolamine, 1,2-dimyristoyl-sn-glycero-3-phosphoethanolamine, 1,2-dipalmitoyl-sn-glycero-3-phospho-2-mercaptoethanol, 1,2-dipalmitoyl-sn-glycero-3-phosphoethanolamine-N-(succinyl), 1,2-dipalmitoyl-sn-glycero-3-[phospho-rac-(1-glycerol)] (sodium salt), triethylammonium 2,3-diacetoxypropyl 2-(5-(((3aS,6aR)-2-oxohexahydro-1H-thieno[3,4-d]imidazol-4-yl)pentanamido)ethyl phosphate, MPB-PE, MCC-PE, and derivatives thereof, including but not limited to salts. Representative structures are presented in Table 1.

TABLE 1

| Common Name | Chemical Name | Structure |
|---|---|---|
| 1,2-distearoyl-sn-glycero-3-phosphocholine | 2,3-bis(stearoyloxy)propyl 2-(trimethylammonio)ethyl phosphate | 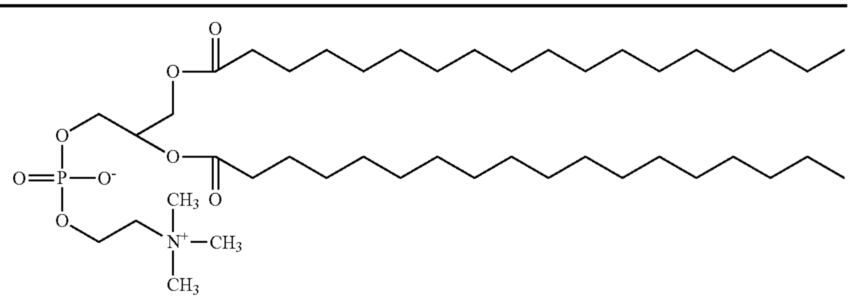 |

TABLE 1-continued

| Common Name | Chemical Name | Structure |
| --- | --- | --- |
| 1,2-dipalmitoyl-sn-glycero-3-phosphocholine | 2,3-bis(palmitoyloxy)propyl 2-(trimethylammonio) ethyl phosphate | 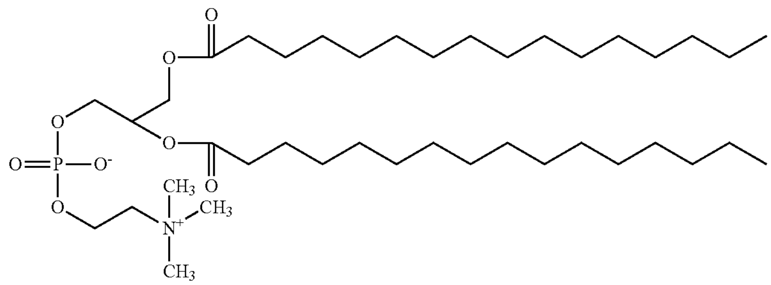 [SMILES: CCCCCCCCCCCCCCCC(=O)OCC(COP(=O)([O-])OCC[N+](C)(C)C)OC(=O)CCCCCCCCCCCCCCC] |
| 1,2-dimyristoyl-sn-glycero-3-phosphocholine | 2,3-bis (tetradecanoyloxy) propyl 2-(trimethylammonio) ethyl phosphate | 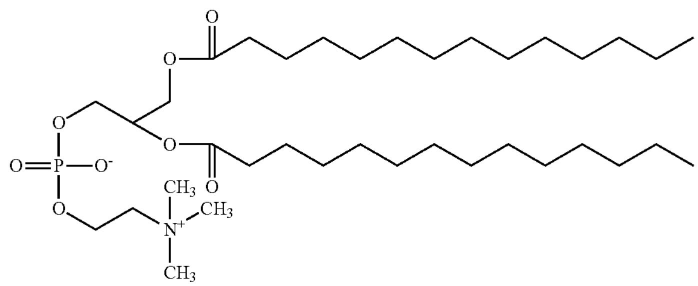 [SMILES: CCCCCCCCCCCCCC(=O)OCC(COP(=O)([O-])OCC[N+](C)(C)C)OC(=O)CCCCCCCCCCCCC] |
| Cholesterol | 10,13-dimethyl-17-(6-methylheptan-2-yl)-2,3,4,7,8,9,10,11,12,13,14,15,16,17-tetradecahydro-1H-cyclopenta[a]phenanthren-3-ol | 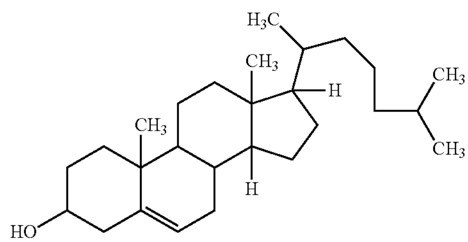 [SMILES: CC(C)CCCC(C)C1CCC2C3CC=C4CC(O)CCC4(C)C3CCC12C] |
| MPB-PE (Na+ salt) | 1,2-Dipalmitoyl-sn-glycero-3-phosphoethanolamine-N-[4-(p-maleimido)phenylbutyrate] | 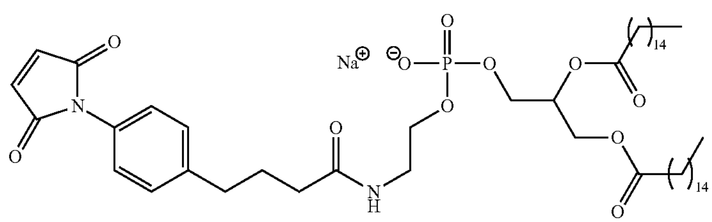 |
| MCC-PE (Na+ salt) | 1,2-Dipalmitoyl-sn-glycero-3-phosphoethanolamine-N-[4-(p-maleimidomethyl)cyclohexane-carboxamide] | 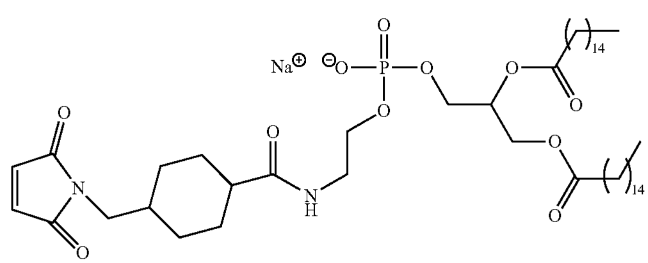 |

By way of non-limiting examples, the lipid-based constituents comprising the composition of the invention may be formed from about 40 to about 65 mol % 1,2 distearoyl-sn-glycero-3-phosphocholine; from about 10 to about 50 mol % dihexadecyl phosphate; from about 15 to about 35 mol % cholesterol, and optionally up to about 15 mol %, preferably less than about 5 mol %, and most preferably about 1 mol % of a targeting agent. The amount of targeting agent necessary to target a given composition will be dictated by the size and structure of the therapeutic agent. It is within the skill level of the ordinary skill artisan, based on the disclosure herein, to select and prepare the composition of the invention containing the appropriate amount of targeting agent.

In a preferred embodiment, the lipid-based constituents comprising the composition of the invention are formed from approximately 62 mole percent 1,2 distearoyl-sn-glycero-3-phosphocholine, approximately 22 mole percent dihexadecyl phosphate, and approximately 16 mole percent cholesterol. In certain variations of this embodiment, at least about 25% of the cholesterol may be thiocholesterol. In a further variation, at least about 50% of the cholesterol may be thiocholesterol. In yet another variation, at least about 75% of the cholesterol may be thiocholesterol. In a further variation, all of the cholesterol may be thiocholesterol.

In another embodiment, the lipid-based constituents comprising the composition of the invention are formed from approximately 61 mole percent 1,2 distearoyl-sn-glycero-3-phosphocholine, approximately 22 mole percent dihexadecyl phosphate, approximately 16 mole percent cholesterol, and about 1 mole percent of at least one targeting agent. Up to an additional 1 mole percent of targeting agent may be added to this embodiment.

In a variation of this embodiment, at least about 25% of the cholesterol may be thiocholesterol. In a further variation, at least about 50% of the cholesterol may be thiocholesterol. In another variation, at least about 75% of the cholesterol may be thiocholesterol. In a further variation, all of the cholesterol may be thiocholesterol.

The lipid-based constituents comprising the composition of the invention may also be formed from 40 to 75 mole % 1,2 dipalmitoyl-sn-glycero-3-phosphocholine; from 5 to 50 mole % dihexadecyl phosphate; from 5 to 15 mole % cholesterol; from 1 to 6 mole % MPB-PE, MCC-PE, or 1,2-distearoyl-sn-glycero-3-phosphoethanolamine; and, optionally, up to about 2 mole %, but preferably not more than 1 mole percent of a targeting agent.

In a specific embodiment, the lipid-based constituents comprising the composition of the invention may be formed from approximately 68 mole % 1,2 dipalmitoyl-sn-glycero-3-phosphocholine, approximately 19 mole % dihexadecyl phosphate, approximately 10 mole % cholesterol, and approximately 3 mole % MPB-PE, MCC-PE, or 1,2-distearoyl-sn-glycero-3-phosphoethanolamine. In certain variations of this embodiment, at least about 25% of the cholesterol may be thiocholesterol. In a further variation, at least about 50% of the cholesterol may be thiocholesterol. In another variation, at least about 75% of the cholesterol may be thiocholesterol. In a further variation, all of the cholesterol may be thiocholesterol.

When any of the cholesterol in any variation of this embodiment is thiocholesterol, and either MPB-PE or MCC-PE is present, MPB-PE or MCC-PE will have been reacted with an appropriate nucleophile prior to being exposed to thiocholesterol.

In each of the above described embodiments, up to about 10% of the 1,2 dipalmitoyl-sn-glycero-3-phosphocholine may be replaced with 1,2-distearoyl-sn-glycero-3-phosphoethanolamine or 1,2-dipalmitoyl-sn-glycero-3-phospho-2-mercaptoethanol.

Each of the above described embodiments further includes at least one associated therapeutic agent or diagnostic agent. In certain embodiments, the therapeutic agent may be non-covalently associated with the composition. In alternative embodiments, the associated therapeutic agent may be covalently linked to a lipid incorporated into a lipid-based constituent comprising the composition of the invention. The process of covalently linking a therapeutic agent to a lipid is described elsewhere herein.

When therapeutic agents are attached via covalent linkages, it is preferred that therapeutic agents are linked to no more than about 10 mole % of the lipids comprising the composition of the invention. Even more preferably, therapeutic agents are linked to no more than about 5 mole % of the lipids comprising the composition of the invention. Most preferably, therapeutic agents are linked to no more than about 2 mole % of the lipids comprising the composition of the invention. Although the above described quantities are preferred, a person of ordinary skill in the art will be able to attenuate or titrate the amount of therapeutic agent present in or on a given composition in order to affect the amount of therapeutic agent delivered to a patient in need thereof.

Any of the above described embodiments may further optionally include one or more RES masking agents. Typically, the one or more RES masking agents are covalently attached, either directly or indirectly, to one or more of the lipids comprising the composition of the invention as is described elsewhere herein. They may, however, be non-covalently associated with a composition of the invention.

When covalently attached, RES masking agents are linked to no more than about 10 mole % of the lipids comprising the composition of the invention. Even more preferably, RES masking agents are linked to no more than about 5 mole % of the lipids comprising the composition of the invention. Most preferably, RES masking agents are linked to no more than about 2 mole % of the lipids comprising the composition of the invention.

When one or more RES masking agents are associated with a composition of the invention non-covalently, any of the above described embodiments may include up to about 10 mole % or greater of one or more RES masking agents.

Although it is preferred that a composition of the invention contain about 18 mole % up to about 22 mole % dihexadecyl phosphate, a composition of the invention may contain up to 30 mole %, even up to 40 mole %, and even as much as 50 mole % dihexadecyl phosphate, inclusive of any incremental amounts of dihexadecyl phosphate therein. This increase in the amount of dihexadecyl phosphate requires a concomitant reduction in the quantity of one or more other lipids in the composition by a total amount equivalent to the quantity of dihexadecyl phosphate added in excess of 18 or 22 mole %.

Preparation

Generally, the composition of the present invention is formed when appropriate lipids and other ingredients (such as a targeting molecule) are homogenized in an aqueous media via microfluidization or other process involving cavitation.

In an embodiment of the invention, the lipids and other ingredients may be homogenized in 18 mM phosphate buffer at a pH of about 6.0 to a pH of about 8.0. Lipid concentration in the phosphate buffer may range from about 10 to about 200 mg/ml and any and all whole and partial integers therebetween. In one embodiment, the lipid concentration is about 30 to about 150 mg/ml. In more preferred embodiment, the lipid concentration is about 15 to about 50 mg/ml. In a most preferred embodiment, the lipid concentration is about 28-30 mg/ml.

Homogenization of the aqueous media, lipids and other ingredients may be accomplished via treatment in a device suitable for homogenization. Examples of suitable devices include, but are not limited to, a Polytron® System PT 6100, an M-110-EH microfluidizer, an ultrasonic sonicator, a high pressure membrane filtration apparatus, and a homogenizer extruder.

In instances where a microfluidizer is used, the microfluidizer is preferably operated at a temperature that is greater than the highest transition temperature of the various lipids and most preferably at a temperature greater than about 75° C. The elevated temperature allows any acyl and alkyl chains present in the lipids to move fluidly as well as conform to and associate with neighboring hydrocarbon moieties. These non-covalent associations directly result in the formation of a constituent of a composition of the present invention.

Figure 9:
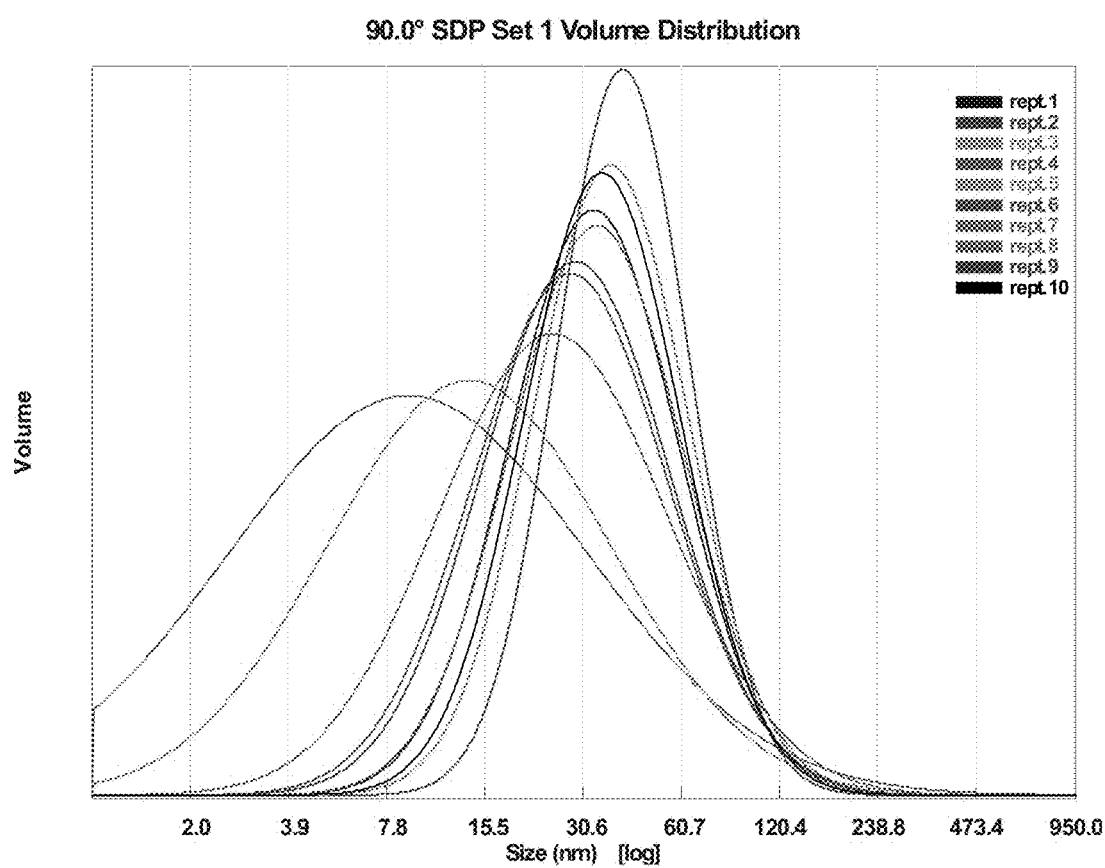
FIG. 9 is a graph of the size distribution of the constituent members of a composition of the invention.

For the microfluidization process, up to about five independent passes are required at 9000 psig in order to prepare compositions having lipid-based constituents sized from about 6 to about 200 nanometers, with the optimal size range being about 6 to about 80 nanometers, and the average size in this range being about 50 to about 60 nanometers. A significant percentage of the lipid-based constituents, are approximately 20 nanometers. Average sizing is measured by a Coulter N-4 Plus Sub-Micron Particle Size Analyzer. After microfluidization, the resulting constituents may be sterile filtered through a 0.8 micron to 0.2 micron gang Supor™ membrane at 50 to 70° C., preferably at about 60° C. FIG. 9 represents repeated size analyses on the same sample as it remained stationary in the Coulter N-4 Plus Sub Micron Particle Size Analyzer. This data demonstrates the dynamic sizing and fluid nature of the lipid-based constituents formed from the lipids comprising the invention.

During the process of sub-micron particle formation, hydrogen bonding, ionic bonding, van der Waal's interactions, dipolar interactions, ion-dipole interactions, hydrophobic associations, and thermodynamic considerations dictate the manner in which the lipids assemble. While not wishing to be bound by any one particular theory, it is believed that the interaction of all of these forces, to varying extents, under the conditions noted above, lead to a dynamically sized composition of the present invention.

Incorporation of a Targeting Agent

In certain embodiments, a composition of the present invention may optionally comprise a targeting agent. Targeting agents alter the composition's bio-distribution and further enhances the efficacy of an associated therapeutic agent. A composition of the present invention may incorporate one or more targeting agents that act to target the composition, and associated therapeutic, to a specific cellular or extracellular receptor. For example, a targeting agent may be used to target insulin associated with a composition of the invention to hepatocytes in order to control postprandial glycogen storage.

In one embodiment, a targeting agent facilitates delivery of a therapeutic agent to the liver and encompasses a class of molecules referred to as "hepatocyte target molecule" (HTM). HTM examples include, but are not limited to, biotin-DHPE, biotin-X-DHPE, and metal derived targeting agents such as poly[Cr-bis(N-2,6-diisopropylphenylcarbamoylmethyl iminodiacetic acid)]. Metal-derived targeting agents and biotin derived targeting agents are discussed below and are fully described in U.S. Pat. Nos. 7,169,410 and 4,603,044; PCT application PCT/US06/19119; and U.S. patent application Ser. Nos. 11/384,728, and 11/384,659. Additional examples of biotin-derived targeting agents are disclosed in Table 2.

When the targeting agent comprises biotin, iminobiotin, carboxybiotin, biocytin, or iminobiocytin, the biotin, iminobiotin, carboxybiotin, biocytin, or iminobiocytin molecules may be bound via an amide bond to the nitrogen of a phospholipid molecule such as 1,2-dipalmitoyl-sn-glycero-3-phosphoethanolamine. The compounds may likewise be bound to a molecule such as cholesterol through an ester linkage. In the case of biocytin and iminobiocytin, the compounds may be bound to benzoyl thioacetyl triglycine via an amide bond between the terminal nitrogen of iminiobiocytin and the terminal carbonyl of benzoyl thioacetyl triglycine. Alternative bond connectivities to those described above are possible and considered to be within the scope of the present invention.

TABLE 2

| # | Name |
|---|------|
| 1 | N-hydroxysuccinimide (NHS) biotin 2,5-dioxopyrrolidin-1-yl-5-((3aS,6aR)-2-oxohexahydro-1H-thieno[3,4-d]imidazol-4-yl) pentanoate |
| 2 | sulfo-NHS-biotin sodium 2,5-dioxo-3-(trioxidanylthio)pyrrolidin-1-yl 5-((3aS,6aR)-2-oxohexahydro-1H-thieno[3,4-d]imidazol-4-yl) pentanoate |
| 3 | N-hydroxysuccinimide long chain biotin 2,5-dioxopyrrolidin-1-yl-6-(5-((3aS,6aR)-2-oxohexahydro-1H-thieno[3,4-d]imidazol-4-yl) pentanamido)hexanoate |
| 4 | sulfo-N-hydroxysuccinimide long chain biotin sodium 2,5-dioxo-3-(trioxidanylthio)pyrrolidin-1-yl 6-(5-((3aS,6aR)-2-oxohexahydro-1H-thieno[3,4-d]imidazol-4-yl)pentanamido) hexanoate |

TABLE 2-continued

| | | |
|---|---|---|
| 5 | D-biotin 5-((3aS,6aR)-2-oxohexahydro-1H-thieno[3,4-d]imidazol-4-yl)pentanoic acid | |
| 6 | Biocytin 2-amino-6-(5-((3aS,6aR)-2-oxohexahydro-1H-thieno[3,4-d]imidazol-4-yl)pentanamido)hexanoic acid | |
| 7 | sulfo-N-hydroxysuccinimide-S-S-biotin sodium 2,5-dioxo-3-(trioxidanylthio)pyrrolidin-1-yl 3-((2-(4-((3aS,6aR)-2-oxohexahydro-1H-thieno[3,4-d]imidazol-4-yl)butylamino)ethyl)disulfanyl)propanoate | |
| 8 | biotin-BMCC 4-((2,5-dioxo-2,5-dihydro-1H-pyrrol-1-yl)methyl)-N-(4-(5-((3aS,6aR)-2-oxohexahydro-1H-thieno[3,4-d]imidazol-4-yl)pentanamido)butyl)cyclohexanecarboxamide | |

TABLE 2-continued

| | | |
|---|---|---|
| 9 | biotin-HPDP | 5-((3aS,6aR)-2-oxohexahydro-1H-thieno[3,4-d]imidazol-4-yl)-N-(6-(3-(pyridin-2-yldisulfanyl)propanamido)hexyl)pentanamide |
| 10 | iodoacetyl-LC-biotin | N-(6-(2-iodoacetamido)hexyl)-5-((3aS,6aR)-2-oxohexahydro-1H-thieno[3,4-d]imidazol-4-yl)pentanamide |
| 11 | biotin-hydrazide | 5-((3aS,6aR)-2-oxohexahydro-1H-thieno[3,4-d]imidazol-4-yl)pentanehydrazide |
| 12 | biotin-LC-hydrazide | N-(6-hydrazinyl-6-oxohexyl)-5-((3aS,6aR)-2-oxohexahydro-1H-thieno[3,4-d]imidazol-4-yl)pentanamide |

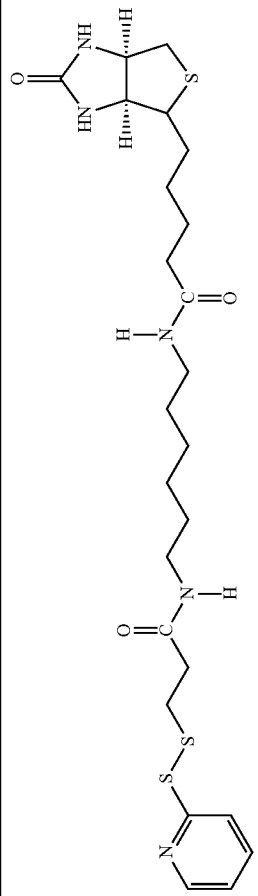
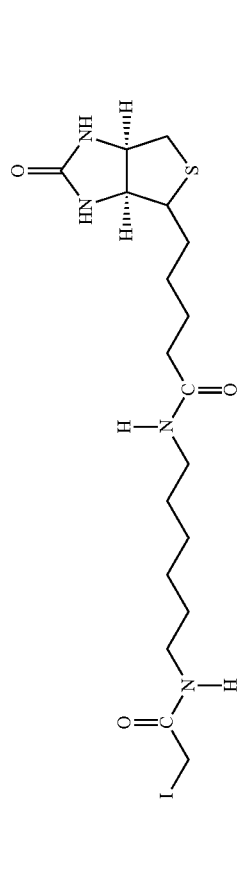
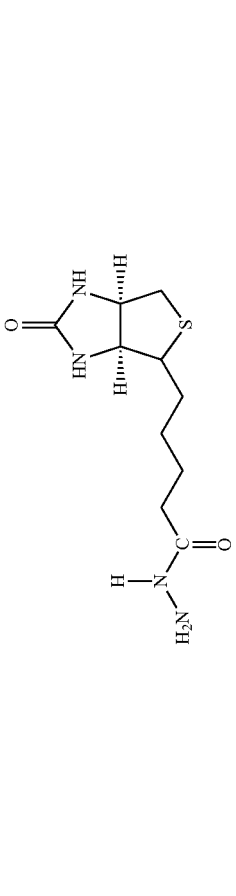
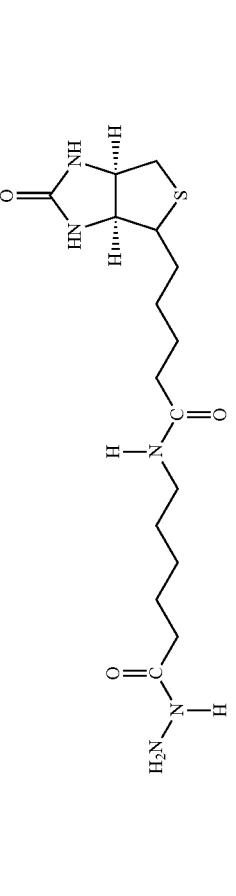

TABLE 2-continued

| | | |
|---|---|---|
| 13 | biocytin hydrazide | N-(5-amino-6-hydrazinyl-6-oxohexyl)-5-((3aS,6aR)-2-oxohexahydro-1H-thieno[3,4-d]imidazol-4-yl)pentanamide |
| 14 | biotin cadaverine | N-(5-aminopentyl)-5-((3aS,6aR)-2-oxohexahydro-1H-thieno[3,4-d]imidazol-4-yl)pentanamide |
| 15 | Carboxybiotin | (3aS,6aR)-4-(4-carboxybutyl)-2-oxohexahydro-1H-thieno[3,4-d]imidazole-1-carboxylic acid |
| 16 | Photobiotin | N-(3-((3-(4-azido-2-nitrophenyl)amino)propyl)(methyl)amino)propyl)-5-((3aS,6aR)-2-oxohexahydro-1H-thieno[3,4-d]imidazol-4-yl)pentanamide |

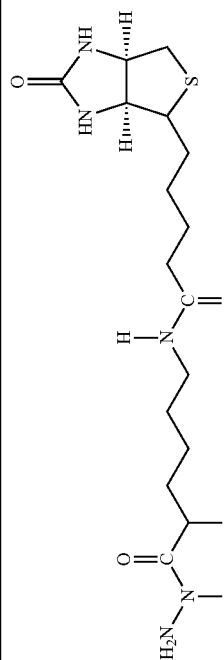
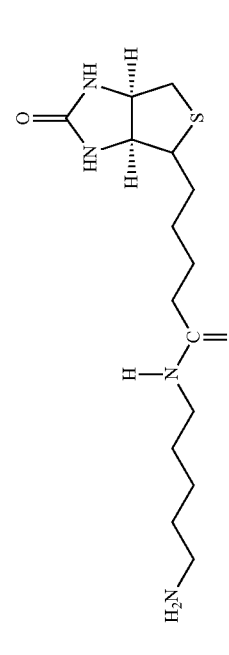
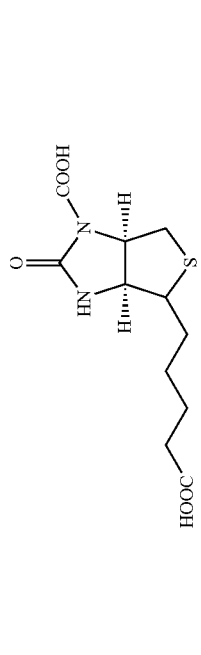
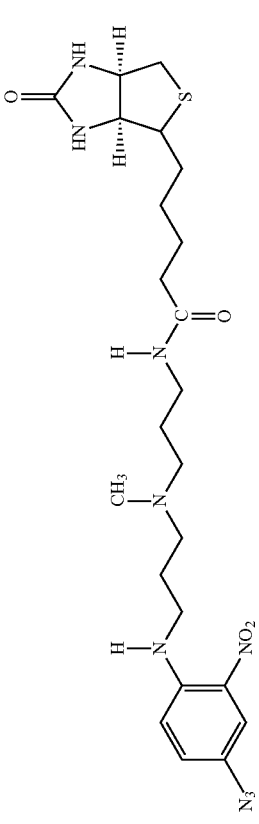

TABLE 2-continued

| | | |
|---|---|---|
| 17 | p-aminobenzoyl biocytin trifluoroacetate 2-(4-aminobenzamido)-6-(5-((3aS,6aR)-2-oxohexahydro-1H-thieno[3,4-d]imidazol-4-yl)pentanamido)hexanoic acid 2,2,2-trifluoroacetate | [structure] |
| 18 | p-diazobenzoyl biocytin 4-(1-carboxy-5-(5-((3aS,6aR)-2-oxohexahydro-1H-thieno[3,4-d]imidazol-4-yl)pentanamido)pentyl carbamoyl)benzenediazonium chloride | [structure] |
| 19 | biotin DHPE G⁺ = Li⁺, Na⁺, K⁺, (Et₃NH)⁺ 2,3-diacetoxypropyl 2-(5-((3aS,6aR)-2-oxohexahydro-1H-thieno[3,4-d]imidazol-4-yl)pentanamido)ethyl phosphate | [structure] |
| 20 | biotin-X-DHPE G⁺ = Li⁺, Na⁺, K⁺, (Et₃NH)⁺ 2,3-diacetoxypropyl 2-(6-(5-((3aS,6aR)-2-oxohexahydro-1H-thieno[3,4-d]imidazol-4-yl)pentanamido)hexanamido)ethyl phosphate | [structure] |

TABLE 2-continued

| 21 | 12-((biotinyl)amino)dodecanoic acid 12-(5-((3aS,6aR)-2-oxohexahydro-1H-thieno[3,4-d]imidazol-4-yl)pentanamido)dodecanoic acid |
| --- | --- |
| 22 | 12-((biotinyl)amino)dodecanoic acid succinimidyl ester 2,5-dioxopyrrolidin-1-yl 12-(5-((3aS,6aR)-2-oxohexahydro-1H-thieno[3,4-d]imidazol-4-yl)pentanamido)dodecanoate |
| 23 | S-biotinyl homocysteine 4-mercapto-2-(5-((3aS,6aR)-2-oxohexahydro-1H-thieno[3,4-d]imidazol-4-yl)pentanamido)butanoic acid |
| 24 | biocytin-X 2-amino-6-(6-(5-((3aS,6aR)-2-oxohexahydro-1H-thieno[3,4-d]imidazol-4-yl)pentanamido)hexanamido)hexanoic acid |

TABLE 2-continued

| 25 | biocytin x-hydrazide N-(5-amino-6-hydrazinyl-6-oxohexyl)-6-(5-((3aS,6aR)-2-oxohexahydro-1H-thieno[3,4-d]imidazol-4-yl)pentanamido)hexanamide |
| 26 | Biotinethylenediamine N-(2-aminoethyl)-5-((3aS,6aR)-2-oxohexahydro-1H-thieno[3,4-d]imidazol-4-yl)pentanamide |
| 27 | biotin-X 6-(5-((3aS,6aR)-2-oxohexahydro-1H-thieno[3,4-d]imidazol-4-yl)pentanamido)hexanoic acid |
| 28 | biotin-X-ethylenediamine N-(2-aminoethyl)-6-(5-((3aS,6aR)-2-oxohexahydro-1H-thieno[3,4-d]imidazol-4-yl)pentanamido)hexanamide |

TABLE 2-continued

| | | |
|---|---|---|
| 29 | biotin-XX hydrazide | N-(6-hydrazinyl-6-oxohexyl)-6-(5-((3aS,6aR)-2-oxohexahydro-1H-thieno[3,4-d]imidazol-4-yl)pentanamido)hexanamide |
| 30 | biotin-XX-SE | 2,5-dioxopyrrolidin-1-yl 6-(6-(5-((3aS,6aR)-2-oxohexahydro-1H-thieno[3,4-d]imidazol-4-yl)pentanamido)hexanamido)hexanoate |
| 31 | biotin-XX.SSE | sodium 2,5-dioxo-1-(6-(6-(5-((3aS,6aR)-2-oxohexahydro-1H-thieno[3,4-d]imidazol-4-yl)pentanamido)hexanamido)hexanoyloxy)pyrrolidine-3-sulfonate |
| 32 | biotin-X-cadaverine | 5-(6-(5-((3aS,6aR)-2-oxohexahydro-1H-thieno[3,4-d]imidazol-4-yl)pentanamido)hexanamido)pentan-1-aminium 2,2,2-trifluoroacetate |

TABLE 2-continued

| 33 | α-(t-BOC)biocytin | 2-(tert-butoxycarbonylamino)-6-(5-((3aS,6aR)-2-oxohexahydro-1H-thieno[3,4-d]imidazol-4-yl)pentanamido)hexanoic acid |
| 34 | N-(biotinyl)-N'-(iodoacetyl)ethylenediamine | N-(2-(2-iodoacetamido)ethyl)-5-((3aS,6aR)-2-oxohexahydro-1H-thieno[3,4-d]imidazol-4-yl)pentanamide |
| 35 | DNP-X-biocytin-X-SE | 2,5-dioxopyrrolidin-1-yl 2-(6-(6-(2,4-dinitrophenylamino)hexanamido)-6-(6-(5-((3aS,6aR)-2-oxohexahydro-1H-thieno[3,4-d]imidazol-4-yl)pentanamido)hexanamido)hexanoate |
| 36 | biotin-X-hydrazide | N-(6-hydrazinyl-6-oxohexyl)-5-((3aS,6aR)-2-oxohexahydro-1H-thieno[3,4-d]imidazol-4-yl)pentanamide |

TABLE 2-continued

| | |
|---|---|
| 37 norbiotinamine hydrochloride 4-((3aS,6aR)-2-oxohexahydro-1H-thieno[3,4-d]imidazol-4-yl)butan-1-aminium chloride | 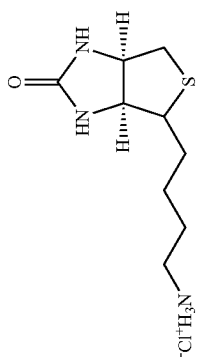 |
| 38 3-(N-maleimidylpropionyl) biocytin 2-(3-(2,5-dioxo-2,5-dihydro-1H-pyrrol-1-yl)propanamido)-6-(5-((3aS,6aR)-2-oxohexahydro-1H-thieno[3,4-d]imidazol-4-yl)pentanamido)hexanoic acid | 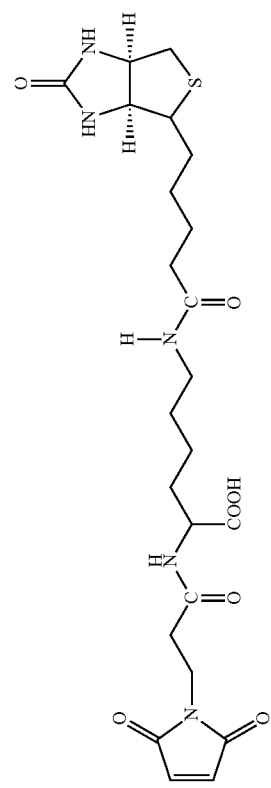 |
| 39 ARP; N'-(2-(aminooxy)acetyl)-5-((3aS,6aR)-2-oxohexahydro-1H-thieno[3,4-d]imidazol-4-yl)pentanehydrazide | 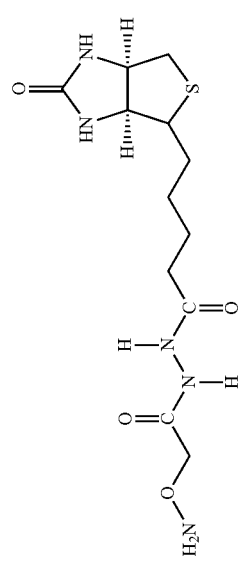 |
| 40 biotin-1-sulfoxide 5-((3aS,6aR)-2-oxohexahydro-1H-thieno[3,4-d]imidazol-4-yl)pentanoic acid sulfoxide | 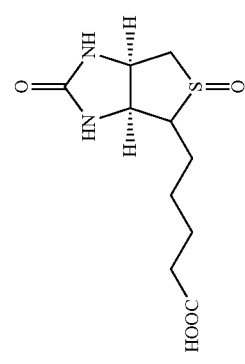 |

TABLE 2-continued

| | | |
|---|---|---|
| 41 | biotin methyl ester | methyl 5-((3aS,6aR)-2-oxohexahydro-1H-thieno[3,4-d]imidazol-4-yl)pentanoate |
| 42 | biotin-maleimide | 6-(2,5-dioxo-2,5-dihydro-1H-pyrrol-1-yl)-N'-(5-((3aS,6aR)-2-oxohexahydro-1H-thieno[3,4-d]imidazol-4-yl)pentanoyl)hexanehydrazide |
| 43 | Biotin-poly(ethyleneglycol) amine | aminomethyl polyethylene 5-((3aS,6aR)-2-oxohexahydro-1H-thieno[3,4-d]imidazol-4-yl)pentanoate |
| 44 | (+) biotin 4-amidobenzoic acid sodium salt | sodium 4-(5-((3aS,6aR)-2-oxohexahydro-1H-thieno[3,4-d]imidazol-4-yl)pentanamido)benzoate |

TABLE 2-continued

| | | |
|---|---|---|
| 45 | Biotin 2-N-acetylamino-2-deoxy-β-D-glucopyranoside ((2R,5S)-3-acetamido-4,5-dihydroxy-6-(hydroxymethyl)-2,3,4,5,6-pentamethyltetrahydro-2H-pyran-2-yl)methyl 5-((3aS,6aR)-2-oxohexahydro-1H-thieno[3,4-d]imidazol-4-yl) pentanoate | 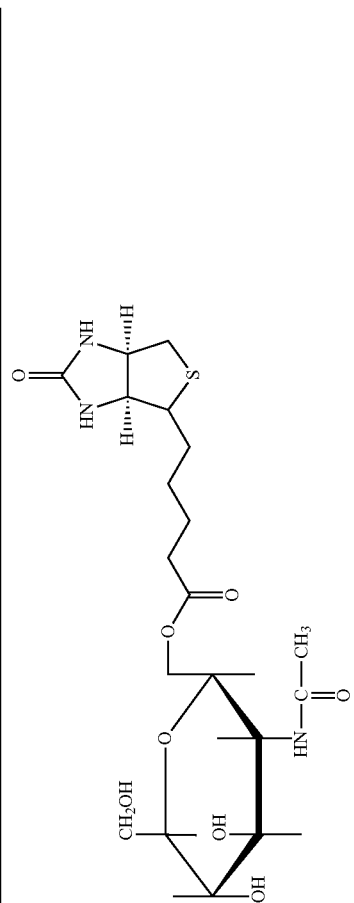 |
| 46 | Biotin-α-D-N-acetylneuraminide (2S,5R)-5-acetamido-4-hydroxy-3,3,4,5,6-pentamethyl-2-((3aS,6aR)-2-oxohexahydro-1H-thieno[3,4-d]imidazol-4-yl)pentanoyloxy)methyl)-6-(1,2,3-trihydroxypropyl)tetrahydro-2H-pyran-2-carboxylic acid | 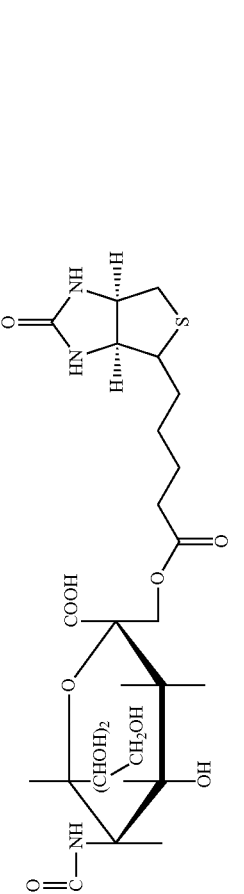 |
| 47 | Biotin-α-L-fucoside ((2R,5S)-3,4,5-trihydroxy-6,6-hexamethyltetrahydro-2H-pyran-2-yl)methyl 5-((3aS,6aR)-2-oxohexahydro-1H-thieno[3,4-d]imidazol-4-yl)pentanoate | 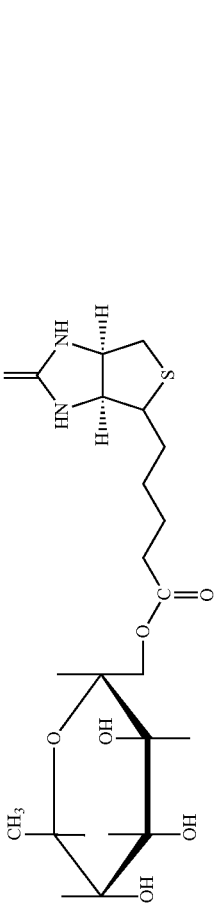 |

TABLE 2-continued
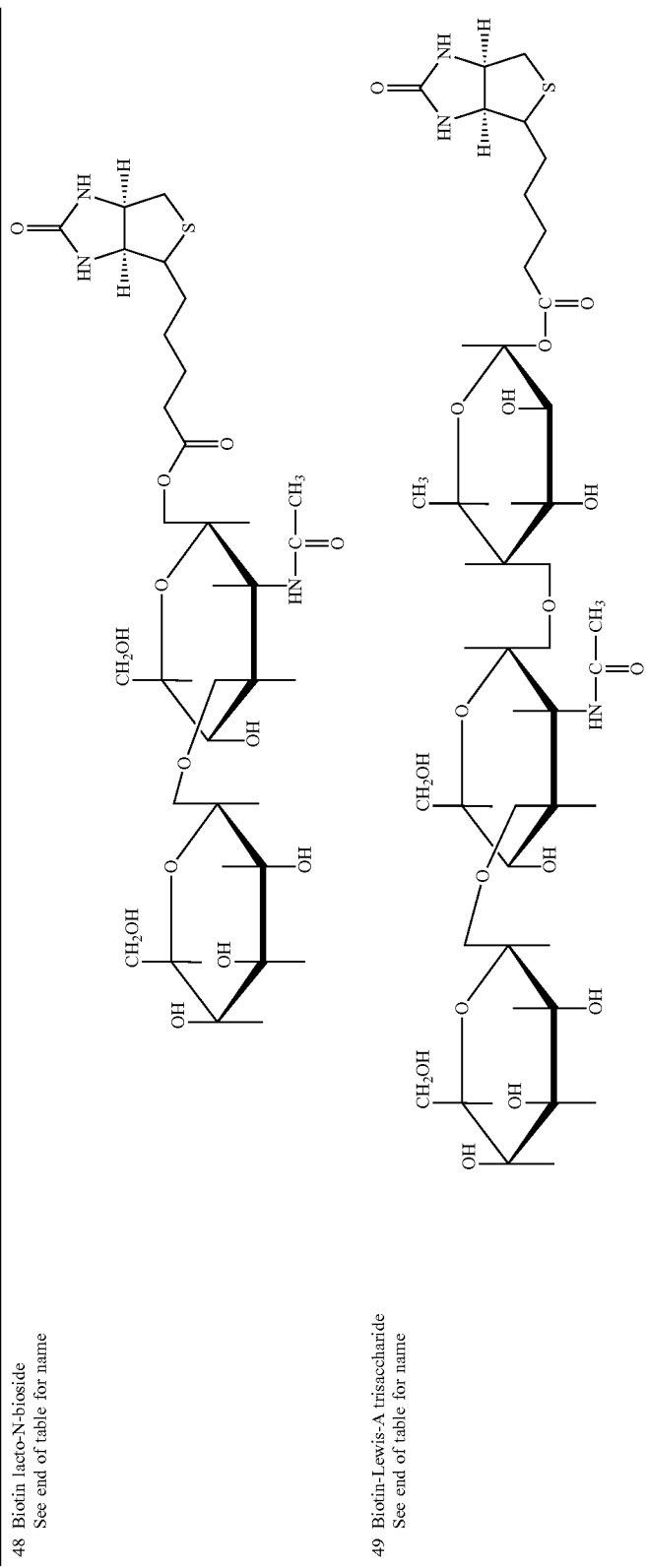
48 Biotin lacto-N-bioside
See end of table for name
49 Biotin-Lewis-A trisaccharide
See end of table for name TABLE 2-continued
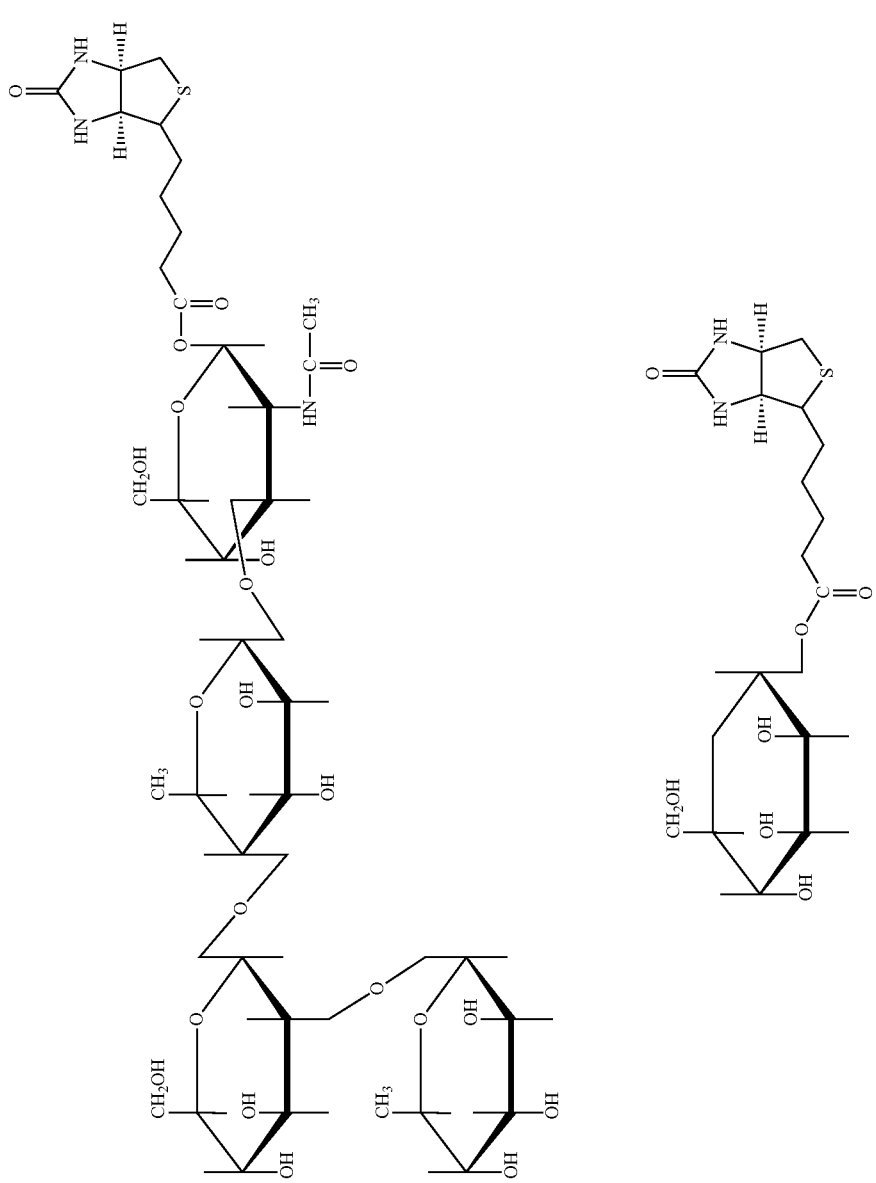
50 Biotin-Lewis-Y tetrasaccharide
See end of table for name
51 Biotin-α-D-mannopyranoside
(((1R,4R)-2,3,4-trihydroxy-5-
(hydroxymethyl)-1,2,3,4,5-
pentamethyl)cyclohexyl)methyl
5-((3aS,6aR)-2-oxohexahydro-
1H-thieno[3,4-d]imidazol-4-yl)
pentanoate TABLE 2-continued

| | |
|---|---|
| 52 | biotin 6-O-phospho-α-D-mannopyranoside ((2R,5S)-3,4,5-trihydroxy-2,3,4,5,6-pentamethyl-6-(phosphonooxymethyl)tetrahydro-2H-pyran-2-yl)methyl 5-((3aS,6aR)-2-oxohexahydro-1H-thieno[3,4-d]imidazol-4-yl)pentanoate |

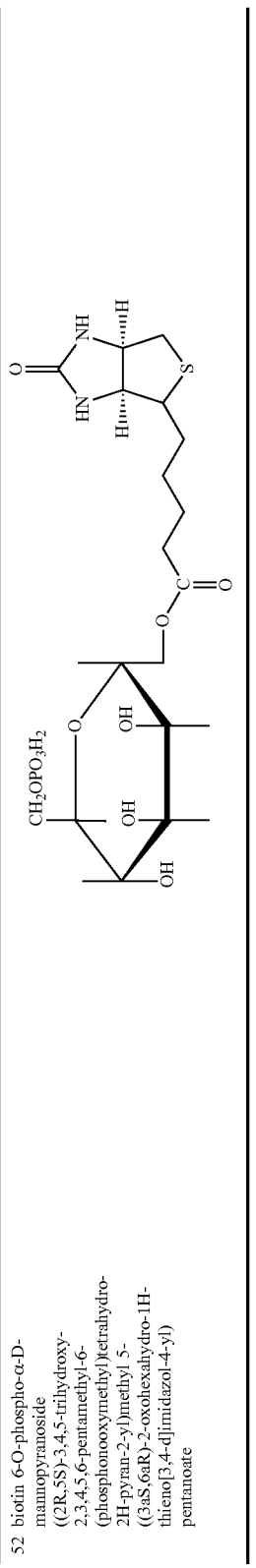

Names of Compounds 48-50:
48. ((2R,5S)-3-hydroxy-5-hydroxy-6-(hydroxymethyl)-2,3,4,6-tetramethyl-4-((((2S,5R)-3,4,5-trihydroxy-6-(hydroxymethyl)-2,3,4,5,6-pentamethyltetrahydro-2H-pyran-2-yl)methoxy)methyl) tetrahydro-2H-pyran-2-yl)methyl 5-((3aS,6aR)-2-oxohexahydro-1H-thieno[3,4-d]imidazol-4-yl)pentanoate ((2R,5S)-3-acetamido-5-hydroxy-6-(hydroxymethyl)-2,3,4,6-tetramethyl-4-((((2S,5R)-3,4,5-trihydroxy-6-(hydroxymethyl)tetrahydro-2H-pyran-2-yl)methoxy)methyl)tetrahydro-1H-thieno[3,4-d]imidazol-4-yl)pentanoate
49. (2R,3R,5S)-5-((((2S,3S,5S)-3-acetamido-5-hydroxy-6-(hydroxymethyl)-2,4,6-trimethyl-4-((((2S,5R)-3,4,5-trihydroxy-6-(hydroxymethyl)-2,3,4,5,6-pentamethyltetrahydro-2H-pyran-2-yl)methoxy)methyl) tetrahydro-2H-pyran-2-yl)methoxy)methyl)-3,4-dihydroxy-2,4,5,6,6-pentamethyl 5-((3aS,6aR)-2-oxohexahydro-1H-thieno[3,4-d]imidazol-4-yl)pentanoate
50. (2S,5S)-5-((((2R,5S)-5-((((2S,5S)-4,5-dihydroxy-6-(hydroxymethyl)-2,3,4,5,6-pentamethyl)-3-((((2S,5S)-3,4,5-trihydroxy-6-(hydroxymethyl)tetrahydro-2H-pyran-2-yl)methoxy)methyl) tetrahydro-2H-pyran-2-yl)methoxy)methyl)-3,4-dihydroxy-2,3,4,5,6,6-hexamethyltetrahydro-2H-pyran-2-yl)methoxy)-5-hydroxy-6-(hydroxymethyl)tetrahydro-2H-pyran-2-yl 5-((3aS,6aR)-2-oxohexahydro-1H-thieno[3,4-d]imidazol-4-yl)pentanoate Structures of iminobiotin compounds are not shown in Table 2. However, the iminobiotin structures are analogs of the biotin structure where the biotin group is replaced by an iminobiotin group. An example is shown below.

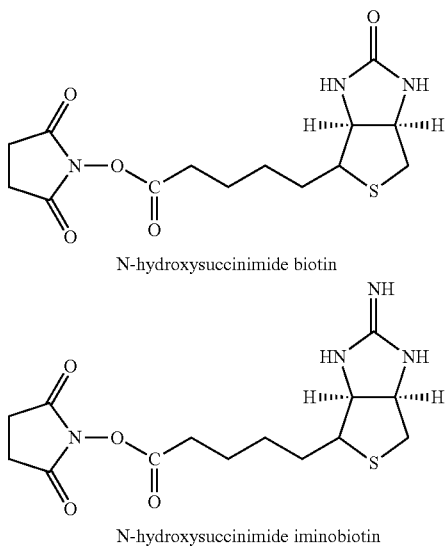

N-hydroxysuccinimide biotin

N-hydroxysuccinimide iminobiotin

In an embodiment of the invention, metal derived targeting agents may be polymeric or monomeric. Polymeric metal derived targeting agents are fully described in U.S. Pat. No. 7,169,410. Monomeric metal derived targeting agents are described in U.S. Pat. No. 4,603,044. Whether polymeric or monomeric, the compounds generally comprise a metal (typically purchased as an inorganic salt) that may be selected from the transition and inner transition metals or neighbors of the transition metals. The transition and inner transition metals from which the metal is selected include: Sc (scandium), Y (yttrium), La (lanthanum), Ac (actinium), the actinide series; Ti (titanium), Zr (zirconium), Hf (hafnium), V (vanadium), Nb (niobium), Ta (tantalum), Cr (chromium), Mo (molybdenum), W (tungsten), Mn (manganese), Tc (technetium), Re (rhenium), Fe (iron), Co (cobalt), Ni (nickel), Ru (ruthenium), Rh (rhodium), Pd (palladium), Os (osmium), Ir (iridium), and Pt (platinum). The neighbors of the transition metals from which the metal may be selected are: Cu (copper), Ag (silver), Au (gold), Zn (zinc), Cd (cadmium), Hg (mercury), Al (aluminum), Ga (gallium), In (indium), Tl (thallium), Ge (germanium), Sn (tin), Pb (lead), Sb (antimony) and Bi (bismuth), and Po (polonium). Preferably, the metal is chromium.

Non-limiting examples of useful salts include chromium chloride (III) hexahydrate; chromium (III) fluoride tetrahydrate; chromium (III) bromide hexahydrate; zirconium (IV) citrate ammonium complex; zirconium (IV) chloride; zirconium (IV) fluoride hydrate; zirconium (IV) iodide; molybdenum (III) bromide; molybdenum (III) chloride; molybdenum (IV) sulfide; iron (III) hydrate; iron (III) phosphate tetrahydrate, iron (III) sulfate pentahydrate, and the like.

In addition to a metal, the metal derived targeting agent comprises one or more complexing agents. A complexing agent is a compound capable of forming a water insoluble coordination complex with the preferred metal. There are several families of suitable complexing agents.

A complexing agent may be selected from the family of iminodiacetic acids of formula (1) wherein $R_1$ is loweralkyl, aryl, arylloweralkyl, or a heterocyclic substituent.

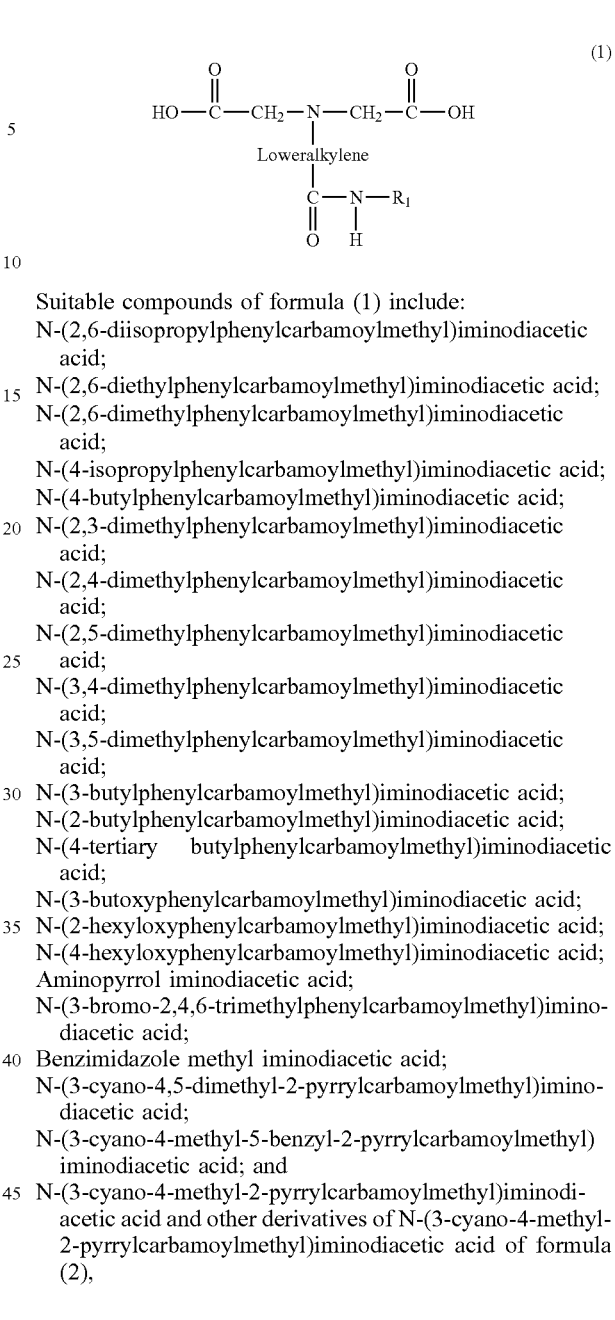

Suitable compounds of formula (1) include:
N-(2,6-diisopropylphenylcarbamoylmethyl)iminodiacetic acid;
N-(2,6-diethylphenylcarbamoylmethyl)iminodiacetic acid;
N-(2,6-dimethylphenylcarbamoylmethyl)iminodiacetic acid;
N-(4-isopropylphenylcarbamoylmethyl)iminodiacetic acid;
N-(4-butylphenylcarbamoylmethyl)iminodiacetic acid;
N-(2,3-dimethylphenylcarbamoylmethyl)iminodiacetic acid;
N-(2,4-dimethylphenylcarbamoylmethyl)iminodiacetic acid;
N-(2,5-dimethylphenylcarbamoylmethyl)iminodiacetic acid;
N-(3,4-dimethylphenylcarbamoylmethyl)iminodiacetic acid;
N-(3,5-dimethylphenylcarbamoylmethyl)iminodiacetic acid;
N-(3-butylphenylcarbamoylmethyl)iminodiacetic acid;
N-(2-butylphenylcarbamoylmethyl)iminodiacetic acid;
N-(4-tertiary butylphenylcarbamoylmethyl)iminodiacetic acid;
N-(3-butoxyphenylcarbamoylmethyl)iminodiacetic acid;
N-(2-hexyloxyphenylcarbamoylmethyl)iminodiacetic acid;
N-(4-hexyloxyphenylcarbamoylmethyl)iminodiacetic acid;
Aminopyrrol iminodiacetic acid;
N-(3-bromo-2,4,6-trimethylphenylcarbamoylmethyl)iminodiacetic acid;
Benzimidazole methyl iminodiacetic acid;
N-(3-cyano-4,5-dimethyl-2-pyrrylcarbamoylmethyl)iminodiacetic acid;
N-(3-cyano-4-methyl-5-benzyl-2-pyrrylcarbamoylmethyl) iminodiacetic acid; and
N-(3-cyano-4-methyl-2-pyrrylcarbamoylmethyl)iminodiacetic acid and other derivatives of N-(3-cyano-4-methyl-2-pyrrylcarbamoylmethyl)iminodiacetic acid of formula (2),

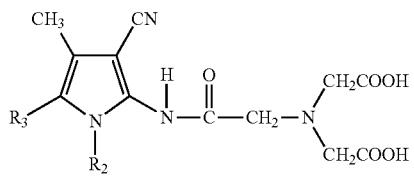

wherein $R_2$ and $R_3$ are the following:

| $R_2$ | $R_3$ |
|---|---|
| H | iso-$C_4H_9$ |
| H | $CH_2CH_2SCH_3$ |
| H | $CH_2C_6H_4$-p-OH |
| $CH_3$ | $CH_3$ |
| $CH_3$ | iso-$C_4H_9$ |

(2)

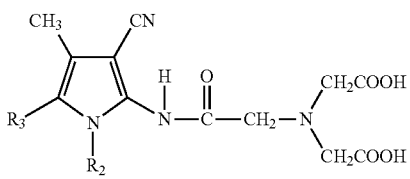

| wherein $R_2$ and $R_3$ are the following: | |
|---|---|
| $R_2$ | $R_3$ |
| $CH_3$ | $CH_2CH_2SCH_3$ |
| $CH_3$ | $C_6H_5$ |
| $CH_3$ | $CH_2C_6H_5$ |
| $CH_3$ | $CH_2C_6H_4\text{-}p\text{-}OCH_3$ |

Alternatively, the complexing agent may be selected from the family of imino diacid derivatives of formula (3), wherein $R_4$, $R_5$, and $R_6$ are independently selected at each occurrence and may be hydrogen, loweralkyl, aryl, arylloweralkyl, alkoxyloweralkyl, and heterocyclic.

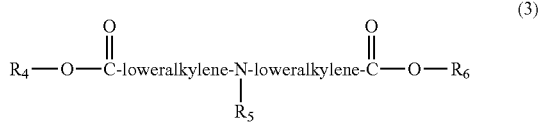
(3)

Suitable compounds of formula (3) include: N'-(2-acetylnaphthyl)iminodiacetic acid (NAIDA); N'-(2-naphthylmethyl)iminodiacetic acid (NMIDA); iminodicarboxymethyl-2-naphthylketone phthalein complexone; 3 (3: 7a: 12a: trihydroxy-24-norchol anyl-23-iminodiacetic acid; benzimidazole methyl iminodiacetic acid; and N-(5,pregnene-3-p-ol-2-oyl carbamoylmethyl)iminodiacetic acid.

The complexing agent may also be selected from the family of amino acids of formula (4),

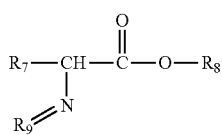
(4)

where $R_7$ is an amino acid side chain; wherein $R_8$ may be loweralkyl, aryl, and arylloweralkyl; and wherein $R_9$ is pyridoxylidene.

Suitable amino acids of the formula (4) are aliphatic amino acids, including, but not limited to: glycine, alanine, valine, leucine, isoleucine; hydroxyamino acids, including serine, and threonine; dicarboxylic amino acids and their amides, including aspartic acid, asparagine, glutamic acid, glutamine; amino acids having basic functions, including lysine, hydroxylysine, histidine, arginine; aromatic amino acids, including phenylalanine, tyrosine, tryptophan, thyroxine; and sulfur-containing amino acids, including cystine and methionine.

The complexing agent may also be selected from amino acid derivatives including, but not limited to (3-alanine-y-amino) butyric acid, O-diazoacetylserine (azaserine), homoserine, ornithine, citrulline, penicillamine and members of the pyridoxylidene class of compounds. Pyridoxylidene compounds include, but are not limited to: pyridoxylidene glutamate; pyridoxylidene isoleucine; pyridoxylidene phenylalanine; pyridoxylidene tryptophan; pyridoxylidene-5-methyl tryptophan; pyridoxylidene-5-hydroxytryptamine; and pyridoxylidene-5-butyltryptamine.

The complexing agent may likewise be selected from the family of diamines of formula (6):

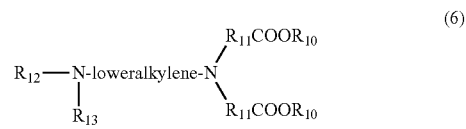
(6)

wherein $R_{10}$ is hydrogen, loweralkyl, or aryl; $R_{11}$ is loweralkylene or arylloweralky; $R_{12}$ and $R_{13}$ are independently selected at each occurrence and may be hydrogen, loweralkyl, alkyl, aryl, arylloweralkyl, acylheterocyclic, toluene, sulfonyl or tosylate.

Examples of suitable diamines of formula (6) include, but are not limited to, ethylenediamine-N, N diacetic acid; ethylenediamine-N,N-bis(-2-hydroxy-5-bromophenyl)acetate; N'-acetylethylenediamine-N,N diacetic acid; N'-benzoyl ethylenediamine-N,N diacetic acid; N'-(p-toluenesulfonyl)ethylenediamine-N, N diacetic acid; N'-(p-t-butylbenzoyl) ethylenediamine-N, N diacetic acid; N'-(benzenesulfonyl)ethylenediamine-N, N diacetic acid; N'-(p-chlorobenzenesulfonyl)ethylenediamine-N, N diacetic acid; N'-(p-ethylbenzenesulfonyl ethylenediamine-N,N diacetic acid; N'-acyl and N'-sulfonyl ethylenediamine-N, N diacetic acid; N'-(p-n-propylbenzenesulfonyl)ethylenediamine-N, N diacetic acid; N'-(naphthalene-2-sulfonyl)ethylenediamine-N, N diacetic acid; and N'-(2,5-dimethylbenzenesulfonyl) ethylenediamine-N, N diacetic acid.

Other, non-limiting examples of complexing compounds or agents include penicillamine; p-mercaptoisobutyric acid; dihydrothioctic acid; 6-mercaptopurine; kethoxal-bis(thiosemicarbazone); Hepatobiliary Amine Complexes, 1-hydrazinophthalazine (hydralazine); sulfonyl urea; Hepatobiliary Amino Acid Schiff Base Complexes; pyridoxylidene glutamate; pyridoxylidene isoleucine; pyridoxylidene phenylalanine; pyridoxylidene tryptophan; pyridoxylidene 5-methyl tryptophan; pyridoxylidene-5-hydroxytryptamine; pyridoxylidene-5-butyltryptamine; tetracycline; 7-carboxy-p-hydroxyquinoline; phenolphthalein; eosin I bluish; eosin I yellowish; verograffin; 3-hydroxyl-4-formyl-pyridene glutamic acid; Azo substituted iminodiacetic acid; hepatobiliary dye complexes, such as rose bengal; congo red; bromosulfophthalein; bromophenol blue; toluidine blue; and indocyanine green; hepatobiliary contrast agents, such as iodipamide; and ioglycamic acid; bile salts, such as bilirubin; cholgycyliodohistamine; and thyroxine; hepatobiliary thio complexes, such as penicillamine; p-mercaptoisobutyric acid; dihydrothiocytic acid; 6-mercaptopurine; and kethoxal-bis(thiosemicarbazone); hepatobiliary amine complexes, such as 1-hydrazinophthalazine (hydralazine); and sulfonyl urea; hepatobiliary amino acid Schiff Base complexes, including pyridoxylidene-5-hydroxytryptamine; and pyridoxylidene-5-butyltryptamine; hepatobiliary protein complexes, such as protamine; ferritin; and asialo-orosomucoid; and asialo complexes, such as lactosaminated albumin; immunoglobulins, G, IgG; and hemoglobin.

Non-Covalent Association of Therapeutic and Diagnostic Agents

As noted previously, in certain embodiments, one or more therapeutic agents may be associated with the composition of the present invention. Examples of therapeutic agents include, but are not limited to, insulin, interferon, rituximab, trastuzumab, uricase, tissue plasminogen activator, thymoglobin, various vaccines, heparin, heparin analogs, antithrombin III, filgrastin, pramilitide acetate, exanatide, epifibatide, antivenins, IgG, IgM, blood clotting Factors VII, VIII, IX, Kallikrein, Kininogen, Hageman Factor (XII), plasma thromboplastin antecedent Factor (XI), tissue factor, Stuart Factor (X), accelerin (V), prothrombin (II), and fibrin stabilizing Factor (XIII); HGH, GLP-1, erythropoietin, parathyroid hormone, serotonin, D- or L-thyroxine, calcitonin, monoclonal antibodies, as well as other therapeutic agents that may include, but are not limited to:

12AP1/E5 - Viventia Biotech
1964 - Aventis
20K growth hormone - AMUR
28P6/E6 - Viventia Biotech
3-Hydroxyphthaloyl-beta-lactoglobulin
4-IBB ligand gene therapy
64-Cu MAb conjugate TETA-1A3 - Mallinckrodt Institute of Radiology
64-Cu MAb conjugate TETA-cT84.66
64-Cu Trastuzumab TETA conjugate - Genentech
A 200 - Amgen
A10255 - Eli Lilly
A1PDX - Hedral Therapeutics
A6 - Angstrom
aaAT-III - Genzyme
Abciximab - Centocor
ABI.001 - Atlantic BioPharmaceuticals
ABT-828 - Abbott
Accutin
Actinohivin
activin - Biotech Australia, Human Therapeutics, Curis
AD 439 - Tanox
AD 519 - Tanox
Adalimumab - Cambridge Antibody Tech.
Adenocarcinoma vaccine - Biomira - NIS
Adenosine deanimase Enzond
Adenosine A2B receptor antagonists - Adenosine Therapeutics
ADP-001 Axis Genetics
AF 13948 Affymax
Afelimomab - Knoll
AFP-SCAN - Immunomedics
AG 2195 - Corixa
agalsidase alfa - Transkaryotic Therapies
agalsidase beta - Genzyme
AGENT - Antisoma
AI 300 - AutoImmune
AI-101 - Teva
AI-102 - Teva
AI-201 AutoImmune
AI-301 AutoImmune
AIDS vaccine - ANRS, CIBG, Hesed Biomed, Hollis-Eden, Rome, United Biomedical, American Home Products, Maxygen
airway receptor ligand - IC Innovations
AJvW 2 - Ajinomoto
AK 30 NGF Alkermes
Albuferon - Human Genome Sciences
albumin - Biogen, DSM Anti-Infectives, Genzyme Transgenics, PPL Therapeutics, TranXenoGen, Welfide Corp.
aldesleukin - Chiron
alefacept - Biogen
Alemtuzumab
Allergy therapy - ALK-Abello/Maxygen, ALK-Abello/RP Scherer
allergy vaccines - Allergy Therapeutics
Alnidofibatide - Aventis Pasteur
Alnorine - SRC VB VECTO
ALP 242 - Gruenentha
Alpha antitrypsin Arriva/Hyland Immuno/ProMetic/Protease Sciences
Alpha-1 antitrypsin - Cutter, Bayer, PPL Therapeutics, Profile, ZymoGenetics, Arriva
Alpha-1 protease inhibitor - Genzyme Transgenics, Welfide Corp.
Alpha-galactose fusion protein - Immunomedics
Alpha-galactosidase A - Research Corporation Technologies, Genzyme
Alpha-glucosidase Genzyme, Novazyme
Alpha-lactalbumin
Alpha-L-iduronidase - Transkaryotic Therapies, BioMarin
alteplase - Genentech
alvircept sudotox - NIH
ALX1-11 - sNPS Pharmaceuticals
Alzheimer's disease gene therapy
AM-133 - AMRAD
Amb a 1 immunostim conj. - Dynavax -continued AMD 3100 - AnorMED - NIS
AMD 3465 - AnorMED - NIS
AMD 3465 - AnorMED - NIS
AMD Fab - Genentech
Amediplase - Menarini, Novartis
AMD Fab - Genentech
Amediplase - Menarini, Novartis
AM-F9
Amoebiasis vaccine
Amphiregulin - Octagene
anakinra - Amgen
analgesic - Nobex
ancestim - Amgen
AnergiX.RA - Corixa, Organon
Angiocidin - InKine
angiogenesis inhibitors - ILEX
AngioMab - Antisoma
Angiopoietins Regeneron/Procter & Gamble
angiostatin - EntreMed
Angiostatin/endostatin gene therapy - Genetix Pharmaceuticals
angiotensin-II, topical - Maret
Anthrax - EluSys Therapeutics/US Army Medical Research Institute
Anthrax vaccine
Anti platelet-derived growth factor D human monoclonal antibodies - CuraGen
Anti-17-1A MAb 3622W94 - GlaxoSmithKline
Anti-2C4 MAb - Genentech
anti-4-1BB monoclonal antibodies - Bristol-Myers Squibb
Anti-Adhesion Platform Tech. - Cytovax
Anti-adipocyte MAb - Cambridge Antibody Tech./ObeSys
antiallergics - Maxygen
antiallergy vaccine - Acambis
Anti-alpha-4-integrin MAb
Anti-alphavβ3 integrin MAb - Applied Molecular Evolution
Anti-angiogenesis monoclonal antibodies - KS Biomedix/Schering AG
Anti-B4 MAb-DC1 conjugate - ImmunoGen
Anti-B7 antibody PRIMATIZED - IDEC
Anti-B7-1 MAb 16-10A1
Anti-B7-1 MAb 1G10
Anti-B7-2 MAb GL-1
Anti-B7-2-gelonin immunotoxin
Antibacterials/antifungals - Diversa/IntraBiotics
Anti-beta-amyloid monoclonal antibodies - Cambridge Antibody Tech., Wyeth-Ayerst
Anti-BLyS antibodies - Cambridge Antibody Tech../Human Genome Sciences
Antibody-drug conjugates - Seattle Genetics/Eos
Anti-C5 MAb BB5-1 - Alexion
Anti-C5 MAb N19-8 - Alexion
Anti-C8 MAb
anticancer cytokines - BioPulse
anticancer matrix - Telios Integra
Anticancer monoclonal antibodies - ARIUS, Immunex
anticancer peptides - Maxygen, Micrologix
Anticancer prodrug Tech. - Alexion Antibody Technologies
Anticancer Troy-Bodies - Affite - Affitech
anticancer vaccine - NIH
anticancers - Epimmune
Anti-CCR5/CXCR4 sheep MAb - KS Biomedix Holdings
Anti-CD11a MAb KBA
Anti-CD11a MAb M17
Anti-CD11a MAb TA-3
Anti-CD11a MAb WT.1
Anti-CD11b MAb - Pharmacia
Anti-CD11b MAb LM2
Anti-CD154 MAb - Biogen
Anti-CD16-anti-CD30 MAb - Biotest
Anti-CD18 MAb - Pharmacia
Anti-CD19 MAb B43
Anti-CD19 MAb - liposomal sodium butyrate conjugate
Anti-CD147
Anti-CD19 MAb-saporin conjugate
Anti-CD19-dsFv-PE38-immunotoxin
Anti-CD2 MAb 12-15
Anti-CD2 MAb B-E2 Diaclone
Anti-CD2 MAb OX34
Anti-CD2 MAb OX54
Anti-CD2 MAb OX55
Anti-CD2 MAb RM2-1
Anti-CD2 MAb RM2-2
Anti-CD2 MAb RM2-4
Anti-CD20 MAb BCA B20

-continued

Anti-CD20-anti-Fc alpha RI bispecific MAb - Medarex, Tenovus
Anti-CD22 MAb-saporin-6 comple
Anti-CD3 immunotoxi
Anti-CD3 MAb 145-2C11 - Pharming
Anti-CD3 MAb CD4IgG conjugate - Genentech
Anti-CD3 MAb humanised - Protein Design, RW Johnson
Anti-CD3 MAb WT32
Anti-CD3 MAb-ricin-chain-A conjugate
Anti-CD3 MAb-xanthirie-oxidase conjugate
Anti-CD30 MAb BerH2 - Medac
Anti-CD30 MAb-saporin conjugate
Anti-CD30-scFv-ETA'-immunotoxin
Anti-CD38 MAb AT13/5
Anti-CD38 MAb-saporin conjugate
Anti-CD3-anti-CD19 bispecific MAb
Anti-CD3-anti-EGFR MAb
Anti-CD3-anti-interleukin-2-receptor MAb
Anti-CD3-anti-MOv18 MAb - Centocor
Anti-CD3-anti-SCLC bispecific MAb
Anti-CD4 idiotype vaccine
Anti-CD4 MAb Centocor, IDEC Pharmaceuticals, Xenova Group
Anti-CD4 MAb 16H5
Anti-CD4 MAb 4162W94 GlaxoSmithKline
Anti-CD4 MAb B-F5 - Diaclone
Anti-CD4 MAb GK1-5
Anti-CD4 MAb KT6
Anti-CD4 MAb OX38
Anti-CD4 MAb PAP conjugate - Bristol-Myers Squibb
Anti-CD4 MAb RIB 5-2
Anti-CD4 MAb W3/25
Anti-CD4 MAb YTA 3.1.2
Anti-CD4 MAb YTS 177-9
Anti-CD40 ligand MAb 5c8 - Biogen
Anti-CD40 MAb
Anti-CD40 MAb 5D12 - Tanox
Anti-CD44 MAb A3D8
Anti-CD44 MAb GKWA3
Anti-CD44 MAb IM7
Anti-CD44 MAb KM81
Anti-CD44 variant monoclonal antibodies - Corixa/Hebrew University
Anti-CD45 MAb BC8-I-131
Anti-CD45RB MAb
Anti-CD48 MAb HuLy-m3
Anti-CD48 MAb WM-63
Anti-CD5 MAb - Becton Dickinson
Anti-CD5 MAb OX19
Anti-CD6 MAb
Anti-CD7 MAb-PAP conjugate
Anti-CD7 MAb-ricin-chain-A conjugate
Anti-CD8 MAb Amerimmune, Cytodyn, Becton Dickinson
Anti-CD8 MAb 2-43
Anti-CD8 MAb OX8
Anti-CD80 MAb P16C10 IDEC
Anti-CD80 MAb P7C10 - ID Vaccine
Anti-CD8-idarubicin conjugate
Anti-CEA MAb CE-25
Anti-CEA MAb MN 14 - Immunomedics
Anti-CEA MAb MN14-PE40 conjugate - Immunomedics
Anti-CEA MAb T84.66-interleukin-2 conjugate
Anti-CEA sheep MAb - KS Biomedix Holdings
Anti-cell surface monoclonal antibodies - Cambridge Antibody Tech./Pharmacia
Anti-c-erbB2-anti-CD3 bifunctional MAb - Otsuka
Anti-CMV MAb - Scotgen
Anti-complement
Anti-CTLA-4 MAb
Anti-EGFR catalytic antibody - Hesed Biomed
anti-EGFR immunotoxin - IVAX
Anti-EGFR MAb - Abgenix
Anti-EGFR MAb 528
Anti-EGFR MAb KSB 107 - KS Biomedix
Anti-EGFR MAb-DM1 conjugate - ImmunoGen
Anti-EGFR MAb-LA1
Anti-EGFR sheep MAb - KS Biomedix
Anti-FAP MAb F19-I-131
Anti-Fas IgM MAb CH11
Anti-Fas MAb Jo2
Anti-Fas MAb RK-8
Anti-Flt-1 monoclonal antibodies - ImClone
Anti-fungal peptides - State University of New York -continued antifungal tripeptides - BTG
Anti-ganglioside GD2 antibody-interleukin-2 fusion protein - Lexigen
Anti-GM2 MAb - Kyowa
Anti-GM-CSF receptor monoclonal antibodies - AMRAD
Anti-gp130 MAb - Tosoh
Anti-HCA monoclonal antibodies - AltaRex/Epigen
Anti-hCG antibodies - Abgenix/AVI BioPharma
Anti-heparanase human monoclonal antibodies - Oxford Glycosciences/Medarex
Anti-hepatitis C virus human monoclonal antibodies - XTL Biopharmaceuticals
Anti-HER-2 antibody gene therapy
Anti-herpes antibody - Epicyte
Anti-HIV antibody - Epicyte
anti-HIV catalytic antibody - Hesed Biomed
anti-HIV fusion protein - Idun
anti-HIV proteins - Cangene
Anti-HM1-24 MAb - Chugai
Anti-hR3 MAb
Anti-Human-Carcinoma-Antigen MAb - Epicyte
Anti-ICAM-1 MAb Boehringer Ingelheim
Anti-ICAM-1 1A-29 - Pharmacia
Anti-ICAM-1 MAb HA58
Anti-ICAM-1 MAb YN1/1.7.4
Anti-ICAM-3 MAb ICM3 - ICOS
Anti-idiotype breast cancer vaccine 11D10
Anti-idiotype breast cancer vaccine ACA14C5
Anti-idiotype cancer vaccine - ImClone Systems/Merck KGaA ImClone, Viventia Biotech
Anti-idiotype cancer vaccine 1A7 - Titan
Anti-idiotype cancer vaccine 3H1 - Titan
Anti-idiotype cancer vaccine TriAb - Titan
Anti-idiotype Chlamydia trachomatis vaccine
Anti-idiotype colorectal cancer vaccine - Novartis
Anti-idiotype colorectal cancer vaccine - Onyvax
Anti-idiotype melanoma vaccine - IDEC Pharmaceuticals
Anti-idiotype ovarian cancer vaccine ACA 125
Anti-idiotype ovarian cancer vaccine AR54 - AltaRex
Anti-idiotype ovarian cancer vaccine CA-125 - AltaRex, Biomira
Anti-IgE catalytic antibody - Hesed Biomed
Anti-IgE MAb E26 - Genentech
Anti-IGF-1 MAb
anti-inflammatory - GeneMax
anti-inflammatory peptide - BTG
anti-integrin peptides - Burnha
Anti-interferon-alpha-receptor MAb 64G12 - Pharma Pacific Management
Anti-interferon-gamma MAb - Protein Design Labs
Anti-interferon-gamma polyclonal antibody - Advanced Biotherapy
Anti-interleukin-10 MAb
Anti-interleukin-12 MAb
Anti-interleukin-1-beta polyclonal antibody - R&D Systems
Anti-interleukin-2 receptor MAb 2A3
Anti-interleukin-2 receptor MAb 33B3-1 - Immunotech
Anti-interleukin-2 receptor MAb ART-18
Anti-interleukin-2 receptor MAb LO-Tact-1
Anti-interleukin-2 receptor MAb Mikbeta1
Anti-interleukin-2 receptor MAb NDS61
Anti-interleukin-4 MAb 11B11
Anti-interleukin-5 MAb - Wallace Laboratories
Anti-interleukin-6 MAb - Centocor, Diaclone, Pharmadigm
Anti-interleukin-8 MAb - Abgenix
Anti-interleukin-8 MAb - Xenotech
Anti-JL1 MAb
Anti-Klebsiella sheep MAb - KS Biomedix Holdings
Anti-Laminin receptor MAb-liposomal doxorubicin conjugate
Anti-LCG MAb - Cytoclonal
Anti-lipopolysaccharide MAb - VitaResc
Anti-L-selectin monoclonal antibodies - Protein Design Labs, Abgenix, Stanford University
Anti-MBL monoclonal antibodies - Alexion/Brigham and Women's Hospital
Anti-MHC monoclonal antibodies
Anti-MIF antibody humanised - IDEC, Cytokine PharmaSciences
Anti-MRSA/VRSA sheep MAb - KS Biomedix Holdings
Anti-mu MAb - Novartis
Anti-MUC-1 MAb
Anti-MUC 18
Anti-Nogo-A MAb IN1
Anti-nuclear autoantibodies - Procyon
Anti-ovarian cancer monoclonal antibodies - Dompe
Anti-p185 monoclonal antibodies
Anti-p43 MAb
Antiparasitic vaccines
Anti-PDGF/bFGF sheep MAb - KS Biomedix Anti-properdin monoclonal antibodies - Abgenix/Gliatech
Anti-PSMA (prostrate specific membrane antigen)
Anti-PSMA MAb J591 - BZL Biologics
Anti-Rev MAb gene therapy
Anti-RSV antibodies - Epicyte, Intracell
Anti-RSV monoclonal antibodies - Medarex/MedImmune, Applied Molecular Evolution/MedImmune
Anti-RSV MAb, inhalation - Alkermes/MedImmune
Anti-RT gene therapy
Antisense K-ras RNA gene therapy
Anti-SF-25 MAb
Anti-sperm antibody - Epicyte
Anti-Tac(Fv)-PE38 conjugate
Anti-TAPA/CD81 MAb AMP1
Anti-tat gene therapy
Anti-TCR-alphabeta MAb H57-597
Anti-TCR-alphabeta MAb R73
Anti-tenascin MAb BC-4-I-131
Anti-TGF-beta human monoclonal antibodies - Cambridge Antibody Tech., Genzyme
Anti-TGF-beta MAb 2G7 - Genentech
Antithrombin III - Genzyme Transgenics, Aventis, Bayer, Behringwerke, CSL, Myriad
Anti-Thy1 MAb
Anti-Thy1.1 MAb
Anti-tissue factor/factor VIIA sheep MAb - KS Biomedix
Anti-TNF monoclonal antibodies - Centocor, Chiron, Peptech, Pharacia, Serono
Anti-TNF sheep MAb - KS Biomedix Holdings
Anti-TNFalpha MAb - Genzyme
Anti-TNFalpha MAb B-C7 - Diaclone
Anti-tooth decay MAb - Planet BioTech.
Anti-TRAIL receptor-1 MAb - Takeda
Antitumour RNases - NIH
Anti-VCAM MAb 2A2 - Alexion
Anti-VCAM MAb 3F4 - Alexion
Anti-VCAM-1 MAb
Anti-VEC MAb - ImClone
Anti-VEGF MAb - Genentech
Anti-VEGF MAb 2C3
Anti-VEGF sheep MAb - KS Biomedix Holdings
Anti-VLA-4 MAb HP1/2 - Biogen
Anti-VLA-4 MAb PS/2
Anti-VLA-4 MAb R1-2
Anti-VLA-4 MAb TA-2
Anti-VAP-1 human MAb
Anti-VRE sheep MAb - KS Biomedix Holdings
ANUP - TranXenoGen
ANUP-1 - Pharis
AOP-RANTES - Senetek
Apan-CH - Praecis Pharmaceuticals
APC-8024 - Demegen
ApoA-1 - Milano, Pharmacia
Apogen - Alexion
apolipoprotein A1 - Avanir
Apolipoprotein E - Bio-Tech. General
Applaggin - Biogen
aprotinin - ProdiGene
APT-070C - AdProTech
AR 177 - Aronex Pharmaceuticals
AR 209 - Aronex Pharmaceuticals, Antigenics
AR545C
ARGENT gene delivery systems - ARIAD
Arresten
ART-123 Asahi Kasei
arylsulfatase B - BioMarin
Arylsulfatase B, Recombinant human - BioMarin
AS 1051 - Ajinomoto
ASI-BCL - Intracell
Asparaginase - Merck
ATL-101 - Alizyme
Atrial natriuretic peptide - Pharis
Aurintricarboxylic acid-high molecular weight
Autoimmune disorders - GPC Biotech/MorphoSys
Autoimmune disorders and transplant rejection - Bristol-Myers Squibb/Genzyme Tra
Autoimmune disorders/cancer - Abgenix/Chiron, CuraGen
Autotaxin
Avicidin - NeoRx
axogenesis factor-1 - Boston Life Sciences
Axokine - Regeneron
B cell lymphoma vaccine - Biomira
B7-1 gene therapy BABS proteins - Chiron
BAM-002 - Novelos Therapeutics
Basiliximab (anti CD25 MAb) - Novartis
Bay-16-9996 - Bayer
Bay-39-9437 - Bayer
Bay-50-4798 - Bayer
BB-10153 - British Biotech
BBT-001 - Bolder BioTech.
BBT-002 - Bolder BioTech.
BBT-003 - Bolder BioTech.
BBT-004 - Bolder BioTech.
BBT-005 - Bolder BioTech.
BBT-006 - Bolder BioTech.
BBT-007 - Bolder BioTech.
BCH-2763 - Shire
BCSF - Millenium Biologix
BDNF - Regeneron - Amgen
Becaplermin - Johnson & Johnson, Chiron
Bectumomab - Immunomedics
Beriplast - Aventis
Beta-adrenergic receptor gene therapy - University of Arkansas
bFGF - Scios
BI 51013 - Behringwerke AG
BIBH 1 - Boehringer Ingelheim
BIM-23190 - Beaufour-Ipsen
birch pollen immunotherapy - Pharmacia
bispecific fusion proteins - NIH
Bispecific MAb 2B1 - Chiron
Bitistatin
BIWA 4 - Boehringer Ingelheim
blood substitute - Northfield, Baxter Intl.
BLP-25 - Biomira
BLS-0597 - Boston Life Sciences
BLyS - Human Genome Sciences
BLyS radiolabelled - Human Genome Sciences
BM 06021 - Boehringer Mannheim
BM-202 - BioMarin
BM-301 - BioMarin
BM-301 - BioMarin
BM-302 - BioMarin
BMP 2 - Genetics Institute/Medtronic-Sofamor Danek, Genetics Institute/Collagenesis, Genetics Institute/Yamanouch
BMP 2 gene therapy
BMP 52 - Aventis Pasteur, Biopharm
BMP-2 - Genetics Institute
BMS 182248 - Bristol-Myers Squibb
BMS 202448 - Bristol-Myers Squibb
bone growth factors - IsoTis
BPC-15 - Pfizer
brain natriuretic peptide
Breast cancer - Oxford GlycoSciences/Medarex
Breast cancer vaccine - Therion Biologics, Oregon
BSSL - PPL Therapeutics
BST-2001 - BioStratum
BST-3002 - BioStratum
BTI 322
butyrylcholinesterase - Shire
C 6822 - COR Therapeutics
C1 esterase inhibitor - Pharming
C3d adjuvant AdProTech
CAB-2.1 - Millennium
calcitonin - Inhale Therapeutics Systems, Aventis, Genetronics, TranXenoGen, Unigene, Rhone Poulenc Rohrer
calcitonin - oral - Nobex, Emisphere, Pharmaceutical Discovery
Calcitonin gene-related peptide - Asahi Kasei - Unigene
calcitonin, human - Suntory
calcitonin, nasal - Novartis, Unigene
calcitonin, Panoderm - Elan
calcitonin, Peptitrol - Shire
calcitonin, salmon - Therapicon
calin - Biopharm
Calphobindin I
calphobindin I - Kowa
calreticulin - NYU
Campath-1G
Campath-1M
cancer therapy - Cangene
cancer vaccine - Aixlie, Aventis Pasteur, Center of Molecular Immunology, YM BioSciences, Cytos, Genzyme, Transgenics, GlobeImmune, Igeneon, ImClone, Virogenetics, InterCell, Iomai, Jenner Biotherapies, Memorial Sloan-Kettering Cancer Center, Sydney
Kimmel Cancer Center, Novavax, Protein Sciences, Argonex, SIGA
Cancer vaccine ALVAC-CEA B7.1 - Aventis Pasteur/Therion Biologics
Cancer vaccine CEA-TRICOM - Aventis Pasteur/Therion Biologics
Cancer vaccine gene therapy - Cantab Pharmaceuticals
Cancer vaccine HER-2/neu - Corixa
Cancer vaccine THERATOPE - Biomira
cancer vaccine, PolyMASC - Valentis
Candida vaccine - Corixa, Inhibitex
Canstatin - ILEX
CAP-18 - Panorama
Cardiovascular gene therapy - Collateral Therapeutics
carperitide - Suntory
Casocidin-1 - Pharis
CAT 152 - Cambridge Antibody Tech.
CAT 192 - Cambridge Antibody Tech.
CAT 213 - Cambridge Antibody Tech.
Catalase - Enzon
Cat-PAD - Circassia
CB 0006 - Celltech
CCK(27-32) - Akzo Nobel
CCR2-64I - NIH
CD, Procept - Paligent
CD154 gene therapy
CD39 - Immunex
CD39-L2 - Hyseq
CD39-L4 - Hyseq
CD4 fusion toxin - Senetek
CD4 IgG - Genentech
CD4 receptor antagonists - Pharmacopeia/Progenics
CD4 soluble - Progenics
CD4, soluble - Genzyme Transgenics
CD40 ligand - Immunex
CD4-ricin chain A - Genentech
CD59 gene therapy - Alexion
CD8 TIL cell therapy - Aventis Pasteur
CD8, soluble - Avidex
CD95 ligand - Roche
CDP 571 - Celltech
CDP 850 - Celltech
CDP-860 (PEG-PDGF MAb) - Celltech
CDP 870 - Celltech
CDS-1 - Ernest Orlando
Cedelizumab - Ortho-McNeil
Cetermin - Insmed
CETP vaccine - Avant
Cetrorelix
Cetuximab
CGH 400 - Novartis
CGP 42934 - Novartis
CGP 51901 - Tanox
CGRP - Unigene
CGS 27913 - Novartis
CGS 32359 - Novartis
Chagas disease vaccine - Corixa
chemokines - Immune Response
CHH 380 - Novartis
chitinase - Genzyme, ICOS
Chlamydia pneumoniae vaccine - Antex Biologics
Chlamydia trachomatis vaccine - Antex Biologics
Chlamydia vaccine - GlaxoSmithKline
Cholera vaccine CVD 103-HgR - Swiss Serum and Vaccine Institute Berne
Cholera vaccine CVD 112 - Swiss Serum and Vaccine Institute Berne
Cholera vaccine inactivated oral - SBL Vaccin
Chrysalin - Chrysalis BioTech.
CI-782 - Hitachi Kase
Ciliary neurotrophic factor - Fidia, Roche
CIM project - Active Biotech
CL 329753 - Wyeth-Ayerst
CL22, Cobra - ML Laboratories
Cleneliximab IDEC
Clostridium difficile antibodies - Epicyte
clotting factors - Octagene
CMB 401 - Celltech
CNTF - Sigma-Tau
Cocaine abuse vaccine - Cantab, ImmuLogic, Scripps
coccidiomycosis vaccine - Arizo
collagen - Type I - Pharming
Collagen formation inhibitors - FibroGen Collagen/hydroxyapatite/bone growth factor - Aventis Pasteur, Biopharm, Orquest
collagenase - BioSpecifics
Colorectal cancer vaccine - Wistar Institute
Component B, Recombinant - Serono
Connective tissue growth factor inhibitors - FibroGen/Taisho
Contortrostatin
contraceptive vaccine - Zonagen
Contraceptive vaccine Hcg
Contraceptive vaccine male reversible - IMMUCON
Contraceptive vaccine zona pellucida - Zonagen
Copper-64 labelled MAb TETA-1A3 - NCI
Coralyne
Corsevin M
C-peptide analogues - Schwarz
CPI-1500 - Consensus
CRF - Neurobiological Tech.
cRGDfV pentapeptide
CRL 1095 - CytRx
CRL 1336 - CytRx
CRL 1605 - CytRx
CS-560 - Sankyo
CSF - ZymoGenetics
CSF-G - Hangzhou, Dong-A, Hanmi
CSF-GM - Cangene, Hunan, LG Chem
CSF-M - Zarix
CT 1579 - Merck Frosst
CT 1786 - Merck Frosst
CT-112^ - BTG
CTB-134L - Xenova
CTC-111 - Kaketsuken
CTGF - FibroGen
CTLA4-Ig - Bristol-Myers Squibb
CTLA4-Ig gene therapy
CTP-37 - AVI BioPharma
C-type natriuretic peptide - Suntory
CVS 995 - Corvas Intl.
CY 397 - Nikko Kyodo
CY 1747 - Epimmune
CY 1748 - Epimmune
Cyanovirin-N
Cystic fibrosis therapy - CBR/IVAX
CYT 351
cytokine Traps - Regeneron
cytokines - Enzon, Cytoclonal
Cytomegalovirus glycoprotein vaccine - Chiron, Aquila Biopharmaceuticals, Aventis Pasteur, Virogenetics
Cytomegalovirus vaccine live - Aventis Pasteur
Cytosine deaminase gene therapy - GlaxoSmithKline
DA-3003 - Dong A
DAB389interleukin-6 - Senetek
DAB389interleukin-7
Daclizumab (anti-IL2R MAb) - Protein Design Labs
DAMP^ - Incyte Genomics
Daniplestim - Pharmacia
darbepoetin alfa - Amgen
DBI-3019 - Diabetogen
DCC - Genzyme
DDF - Hyseq
decorin - Integra, Telios
defensins - Large Scale Biology
DEGR-VIIa
Deimmunised antibody 3B6/22 AGEN
Deimmunised anti-cancer antibodies - Biovation/Viragen
Dendroamide A
Dengue vaccine - Bavarian Nordic, Merck
denileukin diftitox - Ligand
DES-1101 - Desmos
desirudin - Novartis
desmopressin - Unigene
Desmoteplase - Merck, Schering AG
Destabilase
Diabetes gene therapy - DeveloGen, Pfizer
Diabetes therapy - Crucell
Diabetes type 1 vaccine - Diamyd Therapeutics
DiaCIM - YM BioSciences
dialytic oligopeptides - Research Corp
Diamyd - Diamyd Therapeutics
DiaPep227 - Pepgen
DiavaX - Corixa Digoxin MAb - Glaxo
Diphtheria tetanus pertussis-hepatitis B vaccine - GlaxoSmithKline
DIR therapy - Solis Therapeutics
DNase - Genentech
Dornase alfa - Genentech
Dornase alfa, inhalation - Genentech
Doxorubicin-anti-CEA MAb conjugate - Immunomedics
DP-107 - Trimeris
drotrecogin alfa - Eli Lilly
DTctGMCSF
DTP-polio vaccine - Aventis Pasteur
DU 257-KM231 antibody conjugate - Kyowa
dural graft matrix - Integra
Duteplase - Baxter Intl.
DWP-401 - Daewoong
DWP-404 - Daewoong
DWP-408 - Daewoong
Dx 88 (Epi-KAL2) Dyax
Dx 890 (elastin inhibitors) - Dyax
*E coli* O157 vaccine - NIH
E21-R - BresaGen
Eastern equine encephalitis virus vaccine
Echicetin
Echinhibin 1
Echistatin - Merck
Echitamine
Ecromeximab - Kyowa Hakko
EC-SOD - PPL Therapeutics
Eculizumab (5G1.1) - Alexion
EDF - Ajinomoto
EDN derivative - NIH
EDNA - NIH
Edobacomab XOMA
Edrecolomab - Centocor
EF 5077
Efalizumab - Genentech
EGF fusion toxin - Seragen, Ligand
EGF-P64k vaccine - Center of Molecular Immunology
EL 246 - LigoCyte
elastase inhibitor - Synergen
elcatonin - Therapicon
EMD 72000 - Merck KGaA
Emdogain - BIORA
emfilermin - AMRAD
Emoctakin - Novartis
enamel matrix protein - BIORA
Endo III - NYU
endostatin - EntreMed, Pharis
Enhancins - Micrologix
Enlimomab - Isis Pharm.
Enoxaparin sodium - Pharmuka
enzyme linked antibody nutrient depletion therapy - KS Biomedix Holdings
Eosinophil-derived neutralizing agent
EP-51216 - Asta Medica
EP-51389 - Asta Medica
EPH family ligands - Regeneron
Epidermal growth factor - Hitachi Kasei, Johnson & Johnson
Epidermal growth factor fusion toxin - Senetek
Epidermal growth factor-genistein
EPI-HNE-4 - Dyax
EPI-KAL2 - Dyax
Epoetin-alfa - Amgen, Dragon Pharmaceuticals, Nanjing Huaxin
Epratuzumab - Immunomedics
Epstein-Barr virus vaccine - Aviron/SmithKline Beecham, Bioresearch
Eptacog alfa - Novo Nordisk
Eptifibatide - COR Therapeutics
erb-38
Erlizumab - Genentech
erythropoietin - Alkermes, ProLease, Dong-A, Elanex, Genetics Institute, LG Chem, Protein Sciences, Serono, Snow Brand, SRC VB VECTOR, Transkaryotic Therapies
Erythropoietin Beta - Hoffman La Roche
Erythropoietin/Epoetin alfa - Chugai
*Escherichia coli* vaccine - North American Vaccine, SBL Vaccin, Swiss Serum and Vaccine Institute Berne
etanercept - Immunex
examorelin - Mediolanum
Exendin 4 - Amylin
exonuclease VII
F 105 - Centocor -continued F-992 - Fornix
Factor IX - Alpha Therapeutics, Welfide Corp., CSL, enetics Institute/AHP, Pharmacia, PPL Therapeutics
Factor IX gene therapy - Cell Genesys
Factor VII - Novo Nordisk, Bayer, Baxter Intl.
Factor VIIa - PPL Therapeutics, ZymoGenetics
Factor VIII - Bayer Genentech, Beaufour-Ipsen, CLB, Inex, Octagen, Pharmacia, Pharming
Factor VIII - PEGylated - Bayer
Factor VIII fragments - Pharmacia
Factor VIII gene therapy - Targeted Genetics
Factor VIII sucrose formulation - Bayer, Genentech
Factor VIII-2 - Bayer
Factor VIII-3 - Bayer
Factor Xa inhibitors - Merck, Novo Nordisk, Mochida
Factor XIII - ZymoGenetics
Factors VIII and IX gene therapy - Genetics Institute/Targeted Genetics
Famoxin - Genset
Fas (delta) TM protein - LXR BioTech.
Fas TR - Human Genome Sciences
Felvizumab - Scotgen
FFR-VIIa - Novo Nordisk
FG-001 - F-Gene
FG-002 - F-Gene
FG-004 - F-Gene
FG-005 - F-Gene
FGF + fibrin - Repair
Fibrimage - Bio-Tech. General
fibrin-binding peptides - ISIS Innovation
fibrinogen - PPL Therapeutics, Pharming
fibroblast growth factor - Chiron, NYU, Ramot, ZymoGenetics
fibrolase conjugate - Schering AG
Filgrastim - Amgen
filgrastim - PDA modified - Xencor
FLT-3 ligand - Immunex
FN18 CRM
follistatin - Biotech Australia, Human Therapeutics
follitropin alfa - Alkermes, ProLease, PowderJect, Serono, Akzo Nobel
Follitropin Beta - Bayer, Organon
FP 59
FSH - Ferring
FSH + LH - Ferring
F-spondin - CeNeS
fusion protein delivery system - UAB Research Foundation
fusion toxins - Boston Life Sciences
G 5598 - Genentech
GA-II Transkaryotic Therapies
Gamma-interferon analogues - SRC VB VECTOR
Ganirelix - Roche
gastric lipase - Meristem
Gavilimomab
G-CSF - Amgen, SRC VB VECTOR
GDF-1 - CeNeS
GDF-5 - Biopharm
GDNF (glial derived neurotrophic factor) - Amgen
gelsolin - Biogen
Gemtuzumab ozogamicin - Celltech
Gene-activated epoetin-alfa - Aventis Pharma - Transkaryotic Therapies
Glanzmann thrombasthenia gene therapy
Glatiramer acetate - Yeda
glial growth factor 2 - CeNeS
GLP-1 - Amylin, Suntory, TheraTech, Watson
GLP-1 peptide analogues - Zealand Pharaceuticals
glucagon - Eli Lilly, ZymoGenetics
Glucagon-like peptide-1 7-36 amide - Suntory
Glucogen-like peptide - Amylin
Glucocerebrosidase - Genzyme
glutamate decarboxylase - Genzyme Transgenics
Glycoprotein S3 - Kureha
GM-CSF - Immunex
GM-CSF tumour vaccine - PowderJect
GnRH immunotherapeutic - Protherics
Goserelin (LhRH antagonist) - AstraZeneca
gp75 antigen - ImClone
gp96 - Antigenics
GPI 0100 - Galenica
GR 4991W93 - GlaxoSmithKline
Granulocyte colony-stimulating factor - Dong-A
Granulocyte colony-stimulating factor conjugate
grass allergy therapy - Dynavax -continued GRF1-44 ICN
Growth Factor - Chiron, Atrigel, Atrix, Innogenetics, ZymoGenetics, Novo
growth factor peptides - Biotherapeutics
growth hormone - LG Chem
growth hormone, Recombinant human - Serono
GT 4086 - Gliatech
GW 353430 - GlaxoSmithKline
GW-278884 - GlaxoSmithKline
H 11 - Viventia Biotech
H5N1 influenza A virus vaccine - Protein Sciences
haemoglobin - Biopure
haemoglobin 3011, Recombinant - Baxter Healthcare
haemoglobin crosfumaril - Baxter Intl.
haemoglobin stabilized - Ajinomoto
haemoglobin, recombinant - Apex
HAF - Immune Response
Hantavirus vaccine
HB 19
HBNF - Regeneron
HCC-1 - Pharis
hCG - Milkhaus
hCG vaccine - Zonagen
HE-317 - Hollis-Eden Pharmaceuticals
Heat shock protein cancer and influenza vaccines - StressGen
Helicobacter pylori vaccine - Acambis, AstraZeneca/CSL, Chiron, Provalis
Helistat-G - GalaGen
Hemolink - Hemosol
hepapoietin - Snow Brand
heparanase - InSight
heparinase I - Ibex
heparinase III - Ibex
Hepatitis A vaccine - American Biogenetic Sciences
Hepatitis A vaccine inactivated
Hepatitis A vaccine Nothav - Chiron
Hepatitis A-hepatitis B vaccine - GlaxoSmithKline
hepatitis B therapy - Tripep
Hepatitis B vaccine - Amgen, Chiron SpA, Meiji Milk, NIS, Prodeva, PowderJect, Rhein Biotech
Hepatitis B vaccine recombinant - Evans Vaccines, Epitec Combiotech, Genentech, MedImmune, Merck Sharp & Dohme, Rhein Biotech, Shantha Biotechnics, Vector, Yeda
Hepatitis B vaccine recombinant TGP 943 - Takeda
Hepatitis C vaccine - Bavarian Nordic, Chiron, Innogenetics Acambis
Hepatitis D vaccine - Chiron Vaccines
Hepatitis E vaccine recombinant - Genelabs/GlaxoSmithKline, Novavax
hepatocyte growth factor - Panorama, Sosei
hepatocyte growth factor kringle fragments - EntreMed
Her-2/Neu peptides - Corixa
Herpes simplex glycoprotein DNA vaccine - Merck, Wyeth-Lederle Vaccines-Malvern, Genentech, GlaxoSmithKline, Chiron, Takeda
Herpes simplex vaccine - Cantab Pharmaceuticals, CEL-SCI, Henderson Morley
Herpes simplex vaccine live - ImClone Systems/Wyeth-Lederle, Aventis Pasteur
HGF derivatives - Dompe
hIAPP vaccine - Crucell
Hib-hepatitis B vaccine - Aventis Pasteur
HIC 1
HIP - Altachem
Hirudins - Biopharma, Cangene, Dongkook, Japan Energy Corporation, Pharmacia Corporation, SIR International, Sanofi-Synthelabo, Sotragene, Rhein Biotech
HIV edible vaccine - ProdiGene
HIV gp120 vaccine - Chiron, Ajiomoto, GlaxoSmithKline, ID Vaccine, Progenics, VaxGen
HIV gp120 vaccine gene therapy
HIV gp160 DNA vaccine - PowderJect, Aventis Pasteur, Oncogen, Hyland Immuno, Protein Sciences
HIV gp41 vaccine - Panacos
HIV HGP-30W vaccine - CEL-SCI
HIV immune globulin - Abbott, Chiron
HIV peptides - American Home Products
HIV vaccine - Applied bioTech., Axis Genetics, Biogen, Bristol-Myers Squibb, Genentech, Korea Green Cross, NIS, Oncogen, Protein Sciences Corporation, Terumo, Tonen Corporation, Wyeth-Ayerst, Wyeth-Lederle Vaccines-Malvern, Advanced BioScience Laboratories, Bavarian Nordic, Bavarian Nordic/Statens Serum Institute, GeneCure, Immune Response, Progenics, Therion Biologics, United Biomedical, Chiron
HIV vaccine vCP1433 - Aventis Pasteur
HIV vaccine vCP1452 - Aventis Pasteur
HIV vaccine vCP205 - Aventis Pasteur
HL-9 - American BioScience
HM-9239 - Cytran
HML-103 - Hemosol
HML-104 - Hemosol -continued HML-105 - Hemosol
HML-109 - Hemosol
HML-110 - Hemosol
HML-121 - Hemosol
hNLP - Pharis
Hookworm vaccine
host-vector vaccines - Henogen
HPM 1 - Chugai
HPV vaccine - MediGene
HSA - Meristem
HSF - StressGen
HSP carriers - Weizmann, Yeda, Peptor
HSPPC-70 - Antigenics
HSPPC-96, pathogen-derived - Antigenics
HSV 863 - Novartis
HTLV-I DNA vaccine
HTLV-I vaccine
HTLV-II vaccine - Access
HU 901 - Tanox
Hu23F2G - ICOS
HuHMFG1
HumaLYM - Intracell
Human krebs statika - Yamanouchi
human monoclonal antibodies - Abgenix/Biogen, Abgenix/Corixa, Abgenix/Immunex, Abgenix/Lexicon, Abgenix/Pfizer, Athersys/Medarex, Biogen/MorphoSys, CAT/Searle, Centocor/Medarex, Corixa/Kirin Brewery, Corixa/Medarex, Eos BioTech./Medarex, Eos/Xenerex, Exelixis/Protein Design Labs, ImmunoGen/Raven, Medarex/B.Twelve, MorphoSys/ImmunoGen, XTL Biopharmaceuticals/Dyax
Human monoclonal antibodies - Medarex/Northwest Biotherapeutics, Medarex/Seattle Genetics
human netrin-1 - Exelixis
human papillomavirus antibodies - Epicyte
Human papillomavirus vaccine - Biotech Australia, IDEC, StressGen
Human papillomavirus vaccine MEDI 501 - MedImmune/GlaxoSmithKline
Human papillomavirus vaccine MEDI 503/MEDI 504 - MedImmune/GlaxoSmithKline
Human papillomavirus vaccine TA-CIN - Cantab Pharmaceuticals
Human papillomavirus vaccine TA-HPV - Cantab Pharmaceuticals
Human papillomavirus vaccine TH-GW - Cantab/GlaxoSmithKline
human polyclonal antibodies - Biosite/Eos BioTech./Medarex
human type II anti factor VIII monoclonal antibodies - ThromboGenics
humanised anti glycoprotein Ib murine monoclonal antibodies - ThromboGenics
HumaRAD - Intracell
HuMax EGFR - Genmab
HuMax-CD4 - Medarex
HUMax-IL15 - Genmab
HYB 190 - Hybridon
HYB 676 - Hybridon
I-125 MAb A33 - Celltech
Ibritumomab tiuxetan - IDEC
IBT-9401 - Ibex
IBT-9402 - Ibex
IC 14 - ICOS
Idarubicin anti-Ly-2.1
IDEC 114 - IDEC
IDEC 131 - IDEC
IDEC 152 - IDEC
IDM 1 - IDM
IDPS - Hollis-Eden Pharmaceuticals
iduronate-2-sulfatase - Transkaryotic Therapies
IGF/IBP-2-13 - Pharis
IGN-101 - Igeneon
IK HIR02 - Iketon
IL-11 - Genetics Institute/AHP
IL-13-PE38 - NeoPharm
IL-17 receptor - Immunex
IL-18BP - Yeda
IL-1Hy1 - Hyseq
IL-1β - Celltech
IL-1β adjuvant - Celltech
IL-2 - Chiron
IL-2 + IL-12 - Hoffman LaRoche
IL-6/sIL-6R fusion - Hadasit
IL-6R derivative - Tosoh
IL-7-Dap 389 fusion toxin - Ligand
IM-862 - Cytran
IMC-1C11 - ImClone
imiglucerase - Genzyme
Immune globulin intravenous (human) - Hoffman LaRoche
immune privilege factor - Proneuron Immunocal - Immunotec
Immunogene therapy - Briana Bio-Tech
Immunoliposomal 5-fluorodeoxyuridine-dipalmitate
immunosuppressant vaccine - Aixlie
immunotoxin - Antisoma, NIH
ImmuRAIT-Re-188 - Immunomedics
imreg-1 - Imreg
infertility - Johnson & Johnson, E-TRANS
Infliximab - Centocor
Influenza virus vaccine - Aventis Pasteur, Protein Sciences
inhibin - Biotech Australia, Human Therapeutics
Inhibitory G protein gene therapy
INKP-2001 - InKine
Inolimomab - Diaclone
insulin - Autoimmune, Altea, Biobras, BioSante, Bio-Tech. General, Chong Kun Dang, Emisphere, Flamel, Provalis, Rhein Biotech, TranXenoGen
insulin (bovine) - Novartis
insulin analogue - Eli Lilly
Insulin Aspart - Novo Nordisk
insulin detemir - Novo Nordisk
insulin glargine - Aventis
insulin inhaled - Inhale Therapeutics Systems, Alkermes
insulin oral - Inovax
insulin, AeroDose - AeroGen
insulin, AERx - Aradigm
insulin, BEODAS - Elan
insulin, Biphasix - Helix
insulin, buccal - Generex
insulin, I2R - Flemington
insulin, intranasal - Bentley
insulin, oral - Nobex, Unigene
insulin, Orasome - Endorex
insulin, ProMaxx - Epic
insulin, Quadrant - Elan
insulin, recombinant - Aventis
insulin, Spiros - Elan
insulin, Transfersome - IDEA
insulin, Zymo, recombinant - Novo Nordisk
insulinotropin - Scios
Insulysin gene therapy
integrin antagonists - Merck
interferon (Alpha2) - SRC VB VECTOR, Viragen, Dong-A, Hoffman La-Roche, Genentech
interferon - BioMedicines, Human Genome Sciences
interferon (Alfa-n3) - Interferon Sciences Intl.
interferon (Alpha), Biphasix - Helix
interferon (Alpha) - Amgen, BioNative, Novartis, Genzyme Transgenics, Hayashibara, Inhale Therapeutics Systems, Medusa, Flamel, Dong-A, GeneTrol, Nastech, Shantha, Wassermann, LG Chem, Sumitomo, Aventis, Behring EGIS, Pepgen, Servier, Rhein Biotech
interferon (Alpha2A)
interferon (Alpha2B) - Enzon, Schering-Plough, Biogen, IDEA
interferon (Alpha-N1) - GlaxoSmithKline
interferon (beta) - Rentschler, GeneTrol, Meristem, Rhein Biotech, Toray, Yeda, Daiichi, Mochida
interferon (Beta1A) - Serono, Biogen
interferon (beta1A), inhale - Biogen
interferon (β1b) - Chiron
interferon (tau) - Pepgen
Interferon alfacon-1 - Amgen
Interferon alpha-2a vaccine
Interferon Beta 1b - Schering/Chiron, InterMune
Interferon Gamma - Boehringer Ingelheim, Sheffield, Rentschler, Hayashibara
interferon receptor, Type I - Serono
interferon(Gamma1B) - Genentech
Interferon-alpha-2b + ribavirin - Biogen, ICN
Interferon-alpha-2b gene therapy - Schering-Plough
Interferon-con1 gene therapy
interleukin-1 antagonists - Dompe
Interleukin-1 receptor antagonist - Abbott Bioresearch, Pharmacia
Interleukin-1 receptor type I - Immunex
interleukin-1 receptor Type II - Immunex
Interleukin-1 trap - Regeneron
Interleukin-1-alpha - Immunex/Roche
interleukin-2 - SRC VB VECTOR, Ajinomoto, Biomira, Chiron
IL-2/diphtheria toxin - Ligand
Interleukin-3 - Cangene
Interleukin-4 - Immunology Ventures, Sanofi Winthrop, Schering-Plough, Immunex/Sanofi Winthrop, Bayer, Ono
interleukin-4 + TNF-Alpha - NIH
interleukin-4 agonist - Bayer interleukin-4 fusion toxin - Ligand
Interleukin-4 receptor - Immunex, Immun
Interleukin-6 - Ajinomoto, Cangene, Yeda, Genetics Institute, Novartis
interleukin-6 fusion protein
interleukin-6 fusion toxin - Ligand, Serono
interleukin-7 - IC Innovations
interleukin-7 receptor - Immunex
interleukin-8 antagonists - Kyowa Hakko/Millennium/Pfizer
interleukin-9 antagonists - Genaera
Interleukin-10 - DNAX, Schering-Plough
Interleukin-10 gene therapy
interleukin-12 - Genetics Institute, Hoffman La-Roche
interleukin-13 - Sanofi
interleukin-13 antagonists - AMRAD
Interleukin-13-PE38QQR
interleukin-15 - Immunex
interleukin-16 - Research Corp
interleukin-18 - GlaxoSmithKline
Interleukin-18 binding protein - Serono
Ior-P3 - Center of Molecular Immunology
IP-10 - NIH
IPF - Metabolex
IR-501 - Immune Response
ISIS 9125 - Isis Pharmaceuticals
ISURF No. 1554 - Millennium
ISURF No. 1866 - Iowa State Univer.
ITF-1697 Italfarmaco
IxC 162 - Ixion
J 695 - Cambridge Antibody Tech., Genetics Inst., Knoll
Jagged + FGF - Repair
JKC-362 - Phoenix Pharmaceuticals
JTP-2942 - Japan Tobacce
Juman monoclonal antibodies - Medarex/Raven
K02 - Axys Pharmaceuticals
Keliximab - IDEC
Keyhole limpet haemocyanin
KGF - Amgen
KM 871 - Kyowa
KPI 135 - Scios
KPI-022 - Scios
Kringle 5
KSB 304
KSB-201 - KS Biomedix
L 696418 - Merck
L 703801 - Merck
L1 - Acorda
L-761191 - Merck
lactoferrin - Meristem, Pharming, Agennix
lactoferrin cardio - Pharming
LAG-3 - Serono
LAIT - GEMMA
LAK cell cytotoxin - Arizona
lamellarins - PharmaMar/University of Malaga
laminin A peptides - NIH
lanoteplase - Genetics Institute
laronidase - BioMarin
Lassa fever vaccine
LCAT - NIH
LDP 01 - Millennium
LDP 02 - Millennium
Lecithinized superoxide dismutase - Seikagaku
LeIF adjuvant - Corixa
leishmaniasis vaccine - Corixa
lenercept - Hoffman La-Roche
Lenograstim - Aventis, Chugai
lepirudin - Aventis
leptin - Amgen, IC Innovations
Leptin gene therapy - Chiron Corporation
leptin, 2nd-generation - Amgen
leridistim - Pharmacia
leuprolide, ProMaxx - Epic
leuprorelin, oral - Unigene
LeuTech - Papatin
LEX 032 - SuperGen
LiDEPT - Novartis
Lintuzumab (anti-CD33 MAb) - Protein Design Labs
lipase - Altus Biologics
lipid A vaccine - EntreMed
lipid-linked anchor Tech. - ICRT, ID Biomedical liposome-CD4 Tech. - Sheffield
Listeria monocytogenes vaccine
LMB 1
LMB 7
LMB 9 - Battelle Memorial Institute, NIH
LM-CD45 Cantab Pharmaceuticals
lovastatin - Merck
LSA-3
LT-β receptor - Biogen
lung cancer vaccine - Corixa
lusupultide - Scios
L-Vax - AVAX
LY 355455 - Eli Lilly
LY 366405 - Eli Lilly
LY-355101 - Eli Lilly
Lyme disease DNA vaccine - Vical/Aventis Pasteur
Lyme disease vaccine - Aquila Biopharmaceuticals, Aventis, Pasteur, Symbicom, GlaxoSmithKline, Hyland Immuno, MedImmune
Lymphocytic choriomeningitis virus vaccine
lymphoma vaccine - Biomira, Genitope
LYP18
lys plasminogen, recombinant
Lysosomal storage disease gene therapy - Avigen
lysostaphin - Nutrition 21
M 23 - Gruenenthal
M1 monoclonal antibodies - Acorda Therapeutics
MA 16N7C2 - Corvas Intl.
malaria vaccine - GlaxoSmithKline, AdProTech, Antigenics, Apovia, Aventis Pasteur, Axis Genetics, Behringwerke, CDCP, Chiron Vaccines, Genzyme Transgenics, Hawaii, MedImmune, NIH, NYU, Oxxon, Roche/Saramane, Biotech Australia, Rx Tech
Malaria vaccine CDC/NIIMALVAC-1
malaria vaccine, multicomponent
mammaglobin - Corixa
mammastatin - Biotherapeutics
mannan-binding lectin - Natimmu
mannan-MUC1 - Psiron
MAP 30
Marinovir - Phytera
MARstem - Maret
MB-015 - Mochida
MBP - ImmuLogic
MCI-028 - Mitsubishi-Tokyo
MCIF - Human Genome Sciences
MDC - Advanced BioScience - Akzo Nobel, ICOS
MDX 11 - Medarex
MDX 210 - Medarex
MDX 22 - Medarex
MDX 22
MDX 240 - Medarex
MDX 33
MDX 44 - Medarex
MDX 447 - Medarex
MDX H210 - Medarex
MDX RA - Houston BioTech., Medarex
ME-104 - Pharmexa
Measles vaccine
Mecasermin - Cephalon/Chiron, Chiron
MEDI 488 - MedImmune
MEDI 500
MEDI 507 - BioTransplant
melanin concentrating hormone - Neurocrine Biosciences
melanocortins - OMRF
Melanoma monoclonal antibodies - Viragen
melanoma vaccine - GlaxoSmithKline, Akzo Nobel, Avant, Aventis Pasteur, Bavarian Nordic, Biovector, CancerVax, Genzyme Molecular Oncology, Humbolt, ImClone Systems, Memorial, NYU, Oxxon
Melanoma vaccine Magevac - Therion
memory enhancers - Scios
meningococcal B vaccine - Chiron
meningococcal vaccine - CAMR
Meningococcal vaccine group B conjugate - North American Vaccine
Meningococcal vaccine group B recombinant - BioChem Vaccines, Microscience
Meningococcal vaccine group Y conjugate - North American Vaccine
Meningococcal vaccine groups A B and C conjugate - North American Vaccine
Mepolizumab - GlaxoSmithKline
Metastatin - EntreMed, Takeda
Met-CkB7 - Human Genome Sciences
met-enkephalin - TNI
METH-1 - Human Genome Sciences methioninase - AntiCancer
Methionine lyase gene therapy - AntiCancer
Met-RANTES - Genexa Biomedical, Serono
Metreleptin
Microtubule inhibitor MAb Immunogen/Abgenix
MGDF - Kirin
MGV - Progenics
micrin - Endocrine
microplasmin - ThromboGenics
MIF - Genetics Institute
migration inhibitory factor - NIH
Mim CD4.1 - Xycte Therapies
mirostipen - Human Genome Sciences
Mitumomab (BEC-2) - ImClone Systems, Merck KGaA
MK 852 - Merck
MLN 1202 (Anti-CCR2 monoclonal antibody) - Millenium Pharmaceuticals
Mobenakin - NIS
molgramostim - Genetics Institute, Novartis
monoclonal antibodies - Abgenix/Celltech, lmmusol/Medarex, Viragen/Roslin Institute, Cambridge Antibody Tech./Elan
MAb 108
MAb 10D5 - MAb 14.18-interleukin-2 immunocytokine - Lexigen
MAb 14G2a
MAb 15A10 MAb 170 - Biomira
MAb 177Lu CC49 MAb 17F9
MAb 1D7
MAb 1F7 - Immune Network
MAb 1H10-doxorubicin conjugate
MAb 26-2F
MAb 2A11
MAb 2E1 - RW Johnson
MAb 2F5
MAb 31.1 - International BioImmune Systems
MAb 32 - Cambridge Antibody Tech., Peptech
MAb 323A3 - Centocor
MAb 3C5
MAb 3F12
MAb 3F8
MAb 42/6
MAb 425 - Merck KGaA
MAb 447-52D - Merck Sharp & Dohme
MAb 45-2D9- - haematoporphyrin conjugate
MAb 4B4
MAb 4E3-CPA conjugate - BCM Oncologia
MAb 4E3-daunorubicin conjugate
MAb 50-6
MAb 50-61A - Institut Pasteur
MAb 5A8 - Biogen
MAb 791T/36-methotrexate conjugate
MAb 7c11.e8
MAb 7E11 C5-selenocystamine conjugate
MAb 93KA9 - Novartis
MAb A5B7-cisplatin conjugate - Biodynamics Research, Pharmacia
MAb A5B7-I-131
MAb A7
MAb A717 - Exocell
MAb A7 - zinostatin conjugate
MAb ABX-RB2 - Abgenix
MAb ACA 11
MAb AFP-I-131 - Immunomedics
MAb AP1
MAb AZ1
MAb B3 - LysPE40 conjugate
MAb B4 - United Biomedical
MAb B43 Genistein-conjugate
MAb B43.13-Tc-99m Biomira
MAb B43-PAP conjugate
MAb B4G7-gelonin conjugate
MAb BCM 43-daunorubicin conjugate - BCM Oncologia
MAb BIS-1
MAb BMS 181170 - Bristol-Myers Squibb
MAb BR55-2
MAb BW494
MAb C242-DM1 conjugate - ImmunoGen
MAb C242-PE conjugate
MAb c30-6
MAb CA208-cytorhodin-S conjugate - Hoechst Japan
MAb CC49 - Enzon
MAb ch14.1

-continued

MAb CH14.18-GM-CSF fusion protein - Lexigen
MAb chCE7
MAb CI-137 - AMRAD
MAb cisplatin conjugate
MAb CLB-CD19
MAb CLB-CD19v
MAb CLL-1 - Peregrine
MAb CLL-1-GM-CSF conjugate
MAb CLL-1-IL-2 conjugate - Peregrine
MAb CLN IgG - doxorubicin conjugates
MAb conjugates - Tanox
MAb D612
MAb Dal B02
MAb DC101 - ImClone
MAb EA 1
MAb EC708 - Biovation
MAb EP-5C7 - Protein Design Labs
MAb ERIC-1 - ICRT
MAb F105 gene therapy
MAb FC 2.15
MAb G250 - Centocor
MAb GA6
MAb GA733
MAb Gliomab-H - Viventia Biotech
MAb HB2-saporin conjugate
MAb HD 37
MAb HD37-ricin chain-A conjugate
MAb HNK20 - Acambis
MAb huN901-DM1 conjugate - ImmunoGen
MAb I-131 CC49 - Corixa
MAb ICO25
MAb ICR12-CPG2 conjugate
MAb ICR-62
MAb IRac-ricin A conjugate
MAb K1
MAb KS1-4-methotrexate conjugate
MAb L6 - Bristol-Myers Squibb, Oncogen
MAb LiCO 16-88
MAb LL2-I-131 - Immunomedics
MAb LL2-Y-90
MAb LS2D617 - Hybritech
MAb LYM-1-gelonin conjugate
MAb LYM-1-I-131
MAb LYM-1-Y-90
MAb LYM-2 - Peregrine
MAb M195
MAb M195-bismuth 213 conjugate - Protein Design Labs
MAb M195-gelonin conjugate
MAb M195-I-131
MAb M195-Y-90
MAb MA 33H1 - Sanofi
MAb MAD11
MAb MGb2
MAb MINT5
MAb MK2-23
MAb MOC31 ETA(252-613) conjugate
MAb MOC-31-In-111
MAb MOC-31-PE conjugate
MAb MR6
MAb MRK-16 - Aventis Pasteur
MAb MS11G6
MAb MX-DTPA BrE-3
MAb MY9
MAb Nd2 - Tosoh
MAb NG-1 - Hygeia
MAb NM01 - Nissin Food
MAb OC 125
MAb OC 125-CMA conjugate
MAb OKI-1 - Ortho-McNeil
MAb OX52 - Bioproducts for Science
MAb PMA5
MAb PR1
MAb Prost 30
MAb R-24
MAb R-24 α Human GD3 - Celltech
MAb RFB4-ricin chain A conjugate
MAb RFT5-ricin chain A conjugate
MAb SC 1
MAb SM-3 ICRT MAb SMART 1D10 - Protein Design Labs
MAb SMART ABL 364 - Novartis
MAb SN6f
MAb SN6f-deglycosylated ricin A chain conjugate
MAb SN6j
MAb SN7-ricin chain A conjugate
MAb T101-Y-90 conjugate - Hybritech
MAb T-88 - Chiron
MAb TB94 - Cancer ImmunoBiology
MAb TEC 11
MAb TES-23 - Chugai
MAb TM31 - Avant
MAb TNT-1 - Cambridge Antibody Tech., Peregrine
MAb TNT-3
MAb TNT-3 - IL2 fusion protein
MAb TP3-At-211
MAb TP3-PAP conjugate
MAb UJ13A - ICRT
MAb UN3
MAb ZME-018-gelonin conjugate
MAb-BC2 - GlaxoSmithKline
MAb-DM1 conjugate - ImmunoGen
MAb-ricin-chain-A conjugate - XOMA
MAb-temoporfin conjugates
Monopharm C - Viventia Biotech
monteplase - Eisai
montirelin hydrate - Gruenenthal
moroctocog alfa - Genetics Institute
Moroctocog-alfa - Pharmacia
MP 4
MP-121 - Biopharm
MP-52 - Biopharm
MRA - Chugai
MS 28168 - Mitsui Chemicals, Nihon Schering
MSH fusion toxin - Ligand
MSI-99 - Genaera
MT 201 - Micromet
Muc-1 vaccine - Corixa
Mucosal tolerance - Aberdeen
mullerian inhibiting subst
muplestim - Genetics Institute, Novartis, DSM Anti-Infectives
murine MAb - KS Biomedix
Mutant somatropin - JCR Pharmaceutical
MV 833 - Toagosei
Mycoplasma pulmonis vaccine
Mycoprex - XOMA
myeloperoxidase - Henogen
myostatin - Genetics Institute
Nacolomab tafenatox - Pharmacia
Nagrecor - Scios
nagrestipen - British Biotech
NAP-5 - Corvas Intl.
NAPc2 - Corvas Intl.
nartograstim - Kyowa
Natalizumab - Protein Design Labs
Nateplase - NIH, Nihon Schering
nateplase - Schering AG
NBI-3001 - Neurocrine Biosci.
NBI-5788 - Neurocrine Biosci.
NBI-6024 - Neurocrine Biosci.
Nef inhibitors - BRI
Neisseria gonorrhoea vaccine - Antex Biologics
Neomycin B-arginine conjugate
Nerelimomab - Chiron
Nerve growth factor - Amgen - Chiron, Genentech
Nerve growth factor gene therapy
nesiritide citrate - Scios
neuregulin-2 - CeNeS
neurocan - NYU
neuronal delivery system - CAMR
Neurophil inhibitory Factor - Corvas
Neuroprotective vaccine - University of Auckland
neurotrophic chimaeras - Regeneron
neurotrophic factor - NsGene, CereMedix
NeuroVax - Immune Response
neurturin - Genentech
neutral endopeptidase - Genentech
NGF enhancers - NeuroSearch
NHL vaccine - Large Scale Biology NIP45 - Boston Life Sciences
NKI-B20
NM 01 - Nissin Food
NMI-139 - NitroMed
NMMP - Genetics Institute
NN-2211 - Novo Nordisk
Noggin - Regeneron
Nonacog alfa
Norelin - Biostar
Norwalk virus vaccine
NRLU 10 - NeoRx
NRLU 10 PE - NeoRx
NT-3 - Regeneron
NT-4/5 - Genentech
NU 3056
NU 3076
NX 1838 - Gilead Sciences
NY ESO-1/CAG-3 antigen - NIH
NYVAC-7 - Aventis Pasteur
NZ-1002 - Novazyme
obesity therapy - Nobex
OC 10426 - Ontogen
OC 144093 - Ontogen
OCIF - Sankyo
Oct-43 - Otsuka
Odulimomab - Immunotech
OK PSA - liposomal
OKT3-gamma-1-ala-ala
OM 991
OM 992
Omalizumab - Genentech
oncoimmunin-L - NIH
Oncolysin B - ImmunoGen
Oncolysin CD6 - ImmunoGen
Oncolysin M - ImmunoGen
Oncolysin S - ImmunoGen
Oncophage - Antigenics
Oncostatin M - Bristol-Myers Squibb
OncoVax-CL - Jenner Biotherapies
OncoVax-P - Jenner Biotherapies
onercept - Yeda
onychomycosis vaccine - Boehringer Ingelheim
opebecan - XOMA
opioids - Arizona
Oprelvekin - Genetics Institute
Oregovomab - AltaRex
Org-33408 b - Akzo Nobel
Orolip DP - EpiCept
Oryzacystatin
OSA peptides - GenSci Regeneration
osteoblast-cadherin GF - Pharis
Osteocalcin-thymidine kinase gene therapy
osteogenic protein - Curis
osteopontin - OraPharma
osteoporosis peptides - Integra, Telios
osteoprotegerin - Amgen, SnowBrand
otitis media vaccines - Antex Biologics
ovarian cancer - University of Alabama
OX40-IgG fusion protein - Cantab, Xenova
P 246 - Diatide
P 30 - Alfacell
p1025 - Active Biotech
P-113^ - Demegen
P-16 peptide - Transition Therapeutics
p43 - Ramot
P-50 peptide - Transition Therapeutics
p53 + RAS vaccine - NIH, NCI
PACAP(1-27) analogue
paediatric vaccines - Chiron
Pafase - ICOS
PAGE-4 plasmid DNA - IDEC
PAI-2 - Biotech Australia, Human Therapeutics
Palifermin (keratinocyte growth factor) - Amgen
Palivizumab - MedImmune
PAM 4 - Merck
pamiteplase - Yamanouchi
pancreatin, Minitabs - Eurand
Pangen - Fournier
Pantarin - Selective Genetics Parainfluenza virus vaccine - Pharmacia, Pierre Fabre
paraoxanase - Esperion
parathyroid hormone - Abiogen, Korea Green Cross
Parathyroid hormone (1-34) - Chugai/Suntory
Parkinson's disease gene therapy - Cell Genesys/Ceregene
Parvovirus vaccine - MedImmune
PCP-Scan - Immunomedics
PDGF - Chiron
PDGF cocktail - Theratechnologies
peanut allergy therapy - Dynavax
PEG anti-ICAM MAb - Boehringer Ingelheim
PEG asparaginase - Enzon
PEG glucocerebrosidase
PEG hirudin - Knoll
PEG interferon-alpha-2a - Roche
PEG interferon-alpha-2b + ribavirin - Biogen, Enzon, ICN Pharmaceuticals, Schering-Plough
PEG MAb A5B7
Pegacaristim - Amgen - Kirin Brewery - ZymoGenetics
Pegaldesleukin - Research Corp
pegaspargase - Enzon
pegfilgrastim - Amgen
PEG-interferon Alpha - Viragen
PEG-interferon Alpha 2A - Hoffman LaRoche
PEG-interferon Alpha 2B - Schering-Plough
PEG-r-hirudin - Abbott
PEG-rHuMGDF - Amgen
PEG-uricase - Mountain View
Pegvisomant - Genentech
PEGylated proteins, PolyMASC - Valentis
PEGylated recombinant native human leptin - Roche
Pemtumomab
Penetratin - Cyclacel
Pepscan - Antisoma
peptide G - Peptech, ICRT
peptide vaccine - NIH, NCI
Pexelizumab
pexiganan acetate - Genaera
Pharmaprojects No. 3179 - NYU
Pharmaprojects No. 3390 - Ernest Orlando
Pharmaprojects No. 3417 - Sumitomo
Pharmaprojects No. 3777 - Acambis
Pharmaprojects No. 4209 - XOMA
Pharmaprojects No. 4349 - Baxter Intl.
Pharmaprojects No. 4651
Pharmaprojects No. 4915 - Avanir
Pharmaprojects No. 5156 - Rhizogenics
Pharmaprojects No. 5200 - Pfizer
Pharmaprojects No. 5215 - Origene
Pharmaprojects No. 5216 - Origene
Pharmaprojects No. 5218 - Origene
Pharmaprojects No. 5267 - ML Laboratories
Pharmaprojects No. 5373 - MorphoSys
Pharmaprojects No. 5493 - Metabolex
Pharmaprojects No. 5707 - Genentech
Pharmaprojects No. 5728 - Autogen
Pharmaprojects No. 5733 - BioMarin
Pharmaprojects No. 5757 - NIH
Pharmaprojects No. 5765 - Gryphon
Pharmaprojects No. 5830 - AntiCancer
Pharmaprojects No. 5839 - Dyax
Pharmaprojects No. 5849 - Johnson & Johnson
Pharmaprojects No. 5860 - Mitsubishi-Tokyo
Pharmaprojects No. 5869 - Oxford GlycoSciences
Pharmaprojects No. 5883 - Asahi Brewery
Pharmaprojects No. 5947 - StressGen
Pharmaprojects No. 5961 - Theratechnologies
Pharmaprojects No. 5962 - NIH
Pharmaprojects No. 5966 - NIH
Pharmaprojects No. 5994 - Pharming
Pharmaprojects No. 5995 - Pharming
Pharmaprojects No. 6023 - IMMUCON
Pharmaprojects No. 6063 - Cytoclonal
Pharmaprojects No. 6073 - SIDDCO
Pharmaprojects No. 6115 - Genzyme
Pharmaprojects No. 6227 - NIH
Pharmaprojects No. 6230 - NIH
Pharmaprojects No. 6236 - NIH
Pharmaprojects No. 6243 - NIH Pharmaprojects No. 6244 - NIH
Pharmaprojects No. 6281 - Senetek
Pharmaprojects No. 6365 - NIH
Pharmaprojects No. 6368 - NIH
Pharmaprojects No. 6373 - NIH
Pharmaprojects No. 6408 - Pan Pacific
Pharmaprojects No. 6410 - Athersys
Pharmaprojects No. 6421 - Oxford GlycoSciences
Pharmaprojects No. 6522 - Maxygen
Pharmaprojects No. 6523 - Pharis
Pharmaprojects No. 6538 - Maxygen
Pharmaprojects No. 6554 - APALEXO
Pharmaprojects No. 6560 - Ardana
Pharmaprojects No. 6562 - Bayer
Pharmaprojects No. 6569 - Eos
Phenoxazine
Phenylase - Ibex
Pigment epithelium derived factor
plasminogen activator inhibitor-1, recombinant - DuPont Pharmaceuticals
Plasminogen activators - Abbott Laboratories, American Home Products, Boehringer Mannheim, Chiron Corporation, DuPont Pharmaceuticals, Eli Lilly, Shionogi, Genentech, Genetics Institute, GlaxoSmithKline, Hemispherx Biopharma, Merck & Co, Novartis, Pharmacia Corporation, Wakamoto, Yeda
plasminogen-related peptides - Bio-Tech. General/MGH
platelet factor 4 - RepliGen
Platelet-derived growth factor - Amgen - ZymoGenetics
Plusonermin - Hayashibara
PMD-2850 - Protherics
Pneumococcal vaccine - Antex Biologics, Aventis Pasteur
Pneumococcal vaccine intranasal - BioChem Vaccines/Biovector
PR1A3
PR-39
pralmorelin - Kaken
Pretarget-Lymphoma - NeoRx
Priliximab - Centocor
PRO 140 - Progenics
PRO 2000 - Procept
PRO 367 - Progenics
PRO 542 - Progenics
pro-Apo A-I - Esperion
prolactin - Genzyme
Prosaptide TX14(A) - Bio-Tech. General
prostate cancer antbodies - Immunex, UroCor
prostate cancer antibody therapy - Genentech/UroGenesys, Genotherapeutics
prostate cancer immunotherapeutics - The PSMA Development Company
prostate cancer vaccine - Aventis Pasteur, Zonagen, Corixa, Dendreon, Jenner Biotherapies, Therion Biologics
prostate-specific antigen - EntreMed
protein A - RepliGen
protein adhesives - Enzon
protein C - Baxter Intl., PPL Therapeutics, ZymoGenetics
protein C activator - Gilead Sciences
protein kinase R antags - NIH
protirelin - Takeda
protocadherin 2 - Caprion
Pro-urokinase - Abbott, Bristol-Myers Squibb, Dainippon, Tosoh - Welfide
P-selectin glycoprotein ligand-1 - Genetics Institute
pseudomonal infections - InterMune
Pseudomonas vaccine - Cytovax
PSGL-Ig - American Home Products
PSP-94 - Procyon
PTH 1-34 - Nobex
Quilimmune-M - Antigenics
R 744 - Roche
R 101933
R 125224 - Sankyo
RA therapy - Cardion
Rabies vaccine recombinant - Aventis Pasteur, BioChem Vaccines, Kaketsuken Pharmaceuticals
RadioTheraCIM - YM BioSciences
Ramot project No. 1315 - Ramot
Ramot project No. K-734A - Ramot
Ramot project No. K-734B - Ramot
Ranibizumab (Anti-VEGF fragment) - Genentech
RANK - Immunex
ranpirnase - Alfacell
ranpirnase-anti-CD22 MAb - Alfacell
RANTES inhibitor - Milan
RAPID drug delivery systems - ARIAD -continued rasburicase - Sanofi
rBPI-21, topical - XOMA
RC 529 - Corixa
rCFTR - Genzyme Transgenics
RD 62198
rDnase - Genentech
RDP-58 - SangStat
RecepTox-Fce - Keryx
RecepTox-GnRH - Keryx, MTR Technologies
RecepTox-MBP - Keryx, MTR Technologies
recFSH - Akzo Nobel, Organon
REGA 3G12
Regavirumab - Teijin
relaxin - Connetics Corp
Renal cancer vaccine - Macropharm
repifermin - Human Genome Sciences
Respiratory syncytial virus PFP-2 vaccine - Wyeth-Lederle
Respiratory syncytial virus vaccine - GlaxoSmithKline, Pharmacia, Pierre Fabre
Respiratory syncytial virus vaccine inactivated
Respiratory syncytial virus-parainfluenza virus vaccine - Aventis Pasteur, Pharmacia
Reteplase - Boehringer Mannheim, Hoffman LaRoche
Retropep - Retroscreen,
RFB4 (dsFv) PE38
RFI 641 - American Home Products
RFTS - UAB Research Foundation
RG 12986 - Aventis Pasteur
RG 83852 - Aventis Pasteur
RG-1059 - RepliGen
rGCR - NIH
rGLP-1 - Restoragen
rGRF - Restoragen
rh Insulin - Eli Lilly
RHAMM targeting peptides - Cangene
rHb1.1 - Baxter Intl.
rhCC10 - Claragen
rhCG - Serono
Rheumatoid arthritis gene therapy
Rheumatoid arthritis vaccine - Veterans Affairs Medical Center
rhLH - Serono
Ribozyme gene therapy - Genset
Rickettsial vaccine recombinant
RIGScan CR - Neoprobe
RIP-3 - Rigel
Rituximab - Genentech
RK-0202 - RxKinetix
RLT peptide - Esperion
rM/NEI - IVAX
rmCRP - Immtech
RN-1001 - Renovo
RN-3 - Renovo
RNAse conjugate - Immunomedics
RO 631908 - Roche
Rotavirus vaccine - Merck
RP 431 - DuPont Pharmaceuticals
RP-128 - Resolution
RPE65 gene therap
RPR 110173 - Aventis Pasteur
RPR 115135 - Aventis Pasteur
RPR 116258A - Aventis Pasteur
rPSGL-Ig - American Home Products
r-SPC surfactant - Byk Gulden
RSV antibody - Medimmune
Ruplizumab - Biogen
rV-HER-2/neu - Therion Biologics
SA 1042 - Sankyo
sacrosidase - Orphan Medical
Sant 7
Sargramostim - Immunex
saruplase - Gruenenthal
Satumomab - Cytogen
SB 1 - COR Therapeutics
SB 207448 - GlaxoSmithKline
SB 208651 - GlaxoSmithKline
SB 240683 - GlaxoSmithKline
SB 249415 - GlaxoSmithKline
SB 249417 - GlaxoSmithKline
SB 6 - COR Therapeutics
SB RA 31012
SC 56929 - Pharmacia SCA binding proteins - Curis, Enzon
scFv(14E1)-ETA Berlex Laboratories, Schering AG,
ScFv(FRP5)-ETA
ScFv6C6-PE40
SCH 55700 - Celltech
Schistosomiasis vaccine - Glaxo Wellcome/Medeva, Brazil
SCPF - Advanced Tissue Sciences
scuPA-suPAR complex - Hadasit
SD-9427 - Pharmacia
SDF-1 - Ono
SDZ 215918 - Novartis
SDZ 280125 - Novartis
SDZ 89104 - Novartis
SDZ ABL 364 - Novartis
SDZ MMA 383 - Novartis
Secretin - Ferring, Repligen
serine protease inhibs - Pharis
sermorelin acetate - Serono
SERP-1 - Viron
sertenef - Dainippon
serum albumin, Recombinant human - Aventis Behring
serum-derived factor - Hadasit
Sevirumab - Novartis
SGN 14 - Seatle Genetics
SGN 15 - Seatle Genetics
SGN 17/19 - Seatle Genetics
SGN 30 - Seatle Genetics
SGN-10 - Seatle Genetics
SGN-11 - Seatle Genetics
SH 306 - DuPont Pharmaceuticals
Shanvac-B - Shantha
Shigella flexneri vaccine - Avant, Acambis, Novavax
Shigella sonnei vaccine
sICAM-1 - Boehringer Ingelheim
Silteplase - Genzyme
SIV vaccine - Endocon, Institut Pasteur
SK 896 - Sanwa Kagaku Kenkyusho
SK-827 - Sanwa Kagaku Kenkyusho
Skeletex - CellFactors
SKF 106160 - GlaxoSmithKline
S-nitroso-AR545C
SNTP - Active Biotech
somatomedin-1 GroPep, Mitsubishi-Tokyo, NIH
somatomedin-1 carrier protein - Insmed
somatostatin - Ferring
Somatotropin/Human Growth Hormone - Bio-Tech. General, Eli Lilly
somatropin - Bio-Tech. General, Alkermes, ProLease, Aventis Behring, Biovector, Cangene, Dong-A, Eli Lilly, Emisphere, Enact, Genentech, Genzyme Transgenics, Grandis/InfiMed, CSL, InfiMed, MacroMed, Novartis, Novo Nordisk, Pharmacia Serono, TranXenoGen
somatropin derivative - Schering AG
somatropin, AIR - Eli Lilly
Somatropin, inhaled - Eli Lilly/Alkermes
somatropin, Kabi - Pharmacia
somatropin, Orasome - Novo Nordisk
Sonermin - Dainippon Pharmaceutical
SP(V5.2)C - Supertek
SPf66
sphingomyelinase - Genzyme
SR 29001 - Sanofi
SR 41476 - Sanofi
SR-29001 - Sanofi
SS1(dsFV)-PE38 - NeoPharm
β2 microglobulin - Avidex
β2-microglobulin fusion proteins - NIH
β-amyloid peptides - CeNeS
β-defensin - Pharis
*Staphylococcus aureus* infections - Inhibitex/ZLB
*Staphylococcus aureus* vaccine conjugate - Nabi
*Staphylococcus* therapy - Tripep
Staphylokinase - Biovation, Prothera, Thrombogenetics
Streptococcal A vaccine - M6 Pharmaceuticals, North American Vaccine
Streptococcal B vaccine - Microscience
Streptococcal B vaccine recombinant - Biochem Vaccines
*Streptococcus pyogenes* vaccine
STRL-33 - NIH
Subalin - SRC VB VECTOR
SUIS - United Biomedical
SUIS-LHRH - United Biomedical
SUN-E3001 - Suntory -continued super high affinity monoclonal antibodies - YM BioSciences
Superoxide dismutase - Chiron, Enzon, Ube Industries, Bio-Tech, Yeda
superoxide dismutase-2 - OXIS
suppressin - UAB Research Foundation
SY-161-P5 - ThromboGenics
SY-162 - ThromboGenics
Systemic lupus erythematosus vaccine - MedClone/VivoRx
T cell receptor peptides - Xoma
T cell receptor peptide vaccine
T4N5 liposomes - AGI Dermatics
TACI, soluble - ZymoGenetics
targeted apoptosis - Antisoma
tasonermin - Boehringer Ingelheim
TASP
TASP-V
Tat peptide analogues - NIH
TBP I - Yeda
TBP II
TBV25H - NIH
Tc 99m ior cea1 - Center of Molecular Immunology
Tc 99m P 748 - Diatide
Tc 99m votumumab - Intracell
Tc-99m rh-Annexin V - Theseus Imaging
teceleukin - Biogen
tenecteplase - Genentech
Teriparatide - Armour Pharmaceuticals, Asahi Kasei, Eli Lilly
terlipressin - Ferring
testisin - AMRAD
Tetrafibricin - Roche
TFPI - EntreMed
tgD-IL-2 - Takeda
TGF-Alpha - ZymoGenetics
TGF-β- Kolon
TGF-β2 - Insmed
TGF-β3 - OSI
Thalassaemia gene therapy - Crucell
TheraCIM-h-R3 - Center of Molecular Immunology, YM BioSciences
Theradigm-HBV - Epimmune
Theradigm-HPV - Epimmune
Theradigm-malaria - Epimmune
Theradigm-melanoma - Epimmune
TheraFab - Antisoma
ThGRF 1-29 - Theratechnologies
ThGRF 1-44 - Theratechnologies
Thrombin receptor activating peptide - Abbott
thrombomodulin - Iowa, Novocastra
Thrombopoietin - Dragon Pharmaceuticals, Genentech
thrombopoietin, Pliva - Receptron
Thrombospondin
thrombostatin - Thromgen
thymalfasin - SciClone
thymocartin - Gedeon Richter
thymosin Alpha1 - NIH
thyroid stimulating hormone - Genzyme
tICAM-1 - Bayer
Tick anticoagulant peptide - Merck
TIF - Xoma
Tifacogin - Chiron, NIS, Pharmacia
Tissue factor - Genentech
Tissue factor pathway inhibitor
TJN-135 - Tsumura
TM 27 - Avant
TM 29 - Avant
TMC-151 - Tanabe Seiyaku
TNF tumour necrosis factor - Asahi Kasei
TNF Alpha - CytImmune
TNF antibody - Johnson & Johnson
TNF binding protein - Amgen
TNF degradation product - Oncotech
TNF receptor - Immunex
TNF receptor 1, soluble - Amgen
TNF Tumour necrosis factor-alpha - Asahi Kasei, Genetech, Mochida
TNF-Alpha inhibitor - Tripep
TNFR:Fc gene therapy - Targeted Genetics
TNF-SAM2
ToleriMab - Innogenetics
*Toxoplasma gondii* vaccine - GlaxoSmithKline
TP 9201 - Telios
TP10 - Avant TP20 - Avant
tPA - Centocor
trafermin - Scios
TRAIL/Apo2L - Immunex
TRAIL-R1 MAb - Cambridge Antibody Technologies
transferrin-binding proteins - CAMR
Transforming growth factor-beta-1 - Genentech
transport protein - Genesis
Trastuzumab - Genetech
TRH - Ferring
Triabin - Schering AG
Triconal
Triflavin
troponin I - Boston Life Sciences
TRP-2^ - NIH
trypsin inhibitor - Mochida
TSP-1 gene therapy
TT-232
TTS-CD2 - Active Biotech
Tuberculosis vaccine - Aventis Pasteur, Genesis
Tumor Targeted Superantigens - Active Biotech - Pharmacia
tumour vaccines - PhotoCure
tumour-activated prodrug antibody conjugates - Millennium/ImmunoGen
tumstatin - ILEX
Tuvirumab - Novartis
TV-4710 - Teva
TWEAK receptor - Immunex
TXU-PAP
TY-10721 - TOA Eiyo
Type I diabetes vaccine - Research Corp
Typhoid vaccine CVD 908
U 143677 - Pharmacia
U 81749 - Pharmacia
UA 1248 - Arizona
UGIF - Sheffield
UIC 2
UK 101
UK-279276 - Corvas Intl
urodilatin - Pharis
urofollitrophin - Serono
Urokinase - Abbott
uteroferrin - Pepgen
V 20 - GLYCODesign
V2 vasopressin receptor gene therapy
vaccines - Active Biotech
Varicella zoster glycoprotein vaccine - Research Corporation Technologies
Varicella zoster virus vaccine live - Cantab Pharmaceuticals
Vascular endothelial growth factor - Genentech, University of California
Vascular endothelial growth factors - R&D Systems
vascular targeting agents - Peregrine
vasopermeation enhancement agents - Peregrine
vasostatin - NIH
VCL - Bio-Tech. General
VEGF - Genentech, Scios
VEGF inhibitor - Chugai
VEGF-2 - Human Genome Sciences
VEGF-Trap - Regeneron
viscumin, recombinant - Madaus
Vitaxin
Vitrase - ISTA Pharmaceuticals
West Nile virus vaccine - Bavarian Nordic
WP 652
WT1 vaccine - Corixa
WX-293 - Wilex BioTech.
WX-360 - Wilex BioTech.
WX-UK1 - Wilex BioTech.
XMP-500 - XOMA
XomaZyme-791 - XOMA
XTL 001 - XTL Biopharmaceuticals
XTL 002 - XTL Biopharmaceuticals
yeast delivery system - GlobeImmune
*Yersinia pestis* vaccine
YIGSR-Stealth - Johnson & Johnson
Yissum Project No. D-0460 - Yissum
YM 207 - Yamanouchi
YM 337 - Protein Design Labs
Yttrium-90 labelled biotin
Yttrium-90-labeled anti-CEA MAb T84.66
ZD 0490 - AstraZeneca ziconotide - Elan
ZK 157138 - Berlex Laboratories
Zolimomab aritox
Zorcell - Immune Response
ZRXL peptides - Novartis In certain embodiments, a therapeutic agent such as insulin is associated with a composition of the invention. Association of insulin with the lipid-based constituents comprising a composition of the invention is achieved via combination of a low molarity solution of insulin with an aqueous suspension of the lipid-based constituents. In this embodiment, the number of lipid molecules involved in the assembly of the lipid-based constituents comprising the composition far surpasses the number of molecules of insulin. This high lipid to insulin ratio minimizes the molecular interactions between insulin and the lipids, insuring that the self-assembly and self-organization process of the lipid-based constituents are not disrupted. This high ratio also facilitates the formation of a stable insulin/composition construct.

Without wishing to be bound by a particular theory, it is believed that the quantity of therapeutic agent(s) associated with the composition of the present invention appears to be a function of loading time, lipid concentration, and buffer molarity. As the lipid concentration in aqueous media is increased, additional therapeutic agents associate with a composition of the present invention. The time required for loading the therapeutic agent may be anywhere from several hours to about one week.

The low concentration of therapeutic agent relative to the concentration of the composition is unique among lipid particle delivery systems. Typically, liposome or liposome-like delivery systems have employed a much larger quantity of therapeutic agent. The efficacy of this embodiment shows that it is possible to utilize less therapeutic agent while still obtaining a pharmacologically desirable result in the patient. This embodiment of the invention therefore provides an advantageous therapeutic option.

In other embodiments the addition of a higher concentration of therapeutic agent may be both desirable and advantageous. The composition of the present invention is capable of associating with, and tolerating, higher molarity solutions of any given therapeutic agent.

A diagrammatic example of insulin associated with a composition of the invention is depicted in FIG. 1.

Serotonin, like insulin, may also be delivered to the liver utilizing a composition including an HTM. Serotonin acts jointly with insulin at the level of the liver to activate hepatic glucose storage during a portal (oral) glucose load. In order to achieve the desired effect, serotonin must be delivered to the liver. Non-targeted serotonin, introduced via injection or oral delivery in pharmacologically acceptable doses cannot effectively induce the desired activity. Therefore, an embodiment of the invention includes a composition comprising an HTM with associated serotonin. This embodiment provides a highly desirable delivery mechanism for this important gluco-regulatory hormone. In an embodiment of the invention designed for the delivery of serotonin, the lipids comprising the composition are approximately 61 mole percent, 1,2-distearoyl-sn-glycero-3-phosphocholine, approximately 22 mole percent dihexadecyl phosphate, approximately 16 mole percent cholesterol and about 1 mole percent of a targeting agent.

Calcitonin is a hormone that regulates bone metabolism. Due to the high prevalence of diseases such as osteoporosis, an oral formulation of this hormone is highly desirable. Presently calcitonin is only deliverable via injection. In an embodiment of the invention designed for the delivery of calcitonin, the lipids selected to form the composition include approximately 62 mole percent, 1,2-distearoyl-sn-glycero-3-phosphocholine, approximately 22 mole percent dihexadecyl phosphate, and approximately 16 mole percent cholesterol.

GLP-1 is a peptide that acts at both the liver and pancreas. In the liver, GLP-1 acts to stimulate glycogen accumulation during a meal. However, prior art administration methods where GLP-1 is administered orally evidence poor bioavailability and reduced efficacy upon oral dosing. In an embodiment of the present invention, GLP-1 associates with a constituent of a composition of the invention form a constitutent/GLP-1 construct. The constituent/GLP-1 construct may further include a targeting agent. Preferably, the lipid components selected to form the constituents of the composition including GLP-1 include approximately 62 mole percent 1,2-distearoyl-sn-glycero-3-phosphocholine, approximately 22 mole percent dihexadecyl phosphate, and approximately 16 mole percent cholesterol.

Thyroxine, although orally bioaviable, is not selective when taken orally. In an embodiment of the invention, though, thyroxine may associate with the composition of the invention giving a constituent/thyroxine construct that may be specifically targeted to the liver, restricting thyroxine's action to that of lowering blood lipids and cholesterol. Preferably, the lipids selected to form the composition for associating thyroxine include approximately 62 mole percent, 1,2-distearoyl-sn-glycero-3-phosphocholine, approximately 22 mole percent dihexadecyl phosphate, approximately 16 mole percent cholesterol, and approximately 1 mole percent Biotin DHPE.

Blood clotting Factors VII, VIII, IX, and X act in either the contact activation (intrinsic), tissue factor (extrinsic), or common pathways for blood clotting. These proteins are not presently orally bioavailable for treatment of diseases such as hemophilia. In an embodiment of the present invention, blood clotting factors VII, VIII, IX, and X may associate with a composition of the invention. Preferably the lipids selected to form the composition for associating one of factors VII, VIII, IX, or X include approximately 62 mole percent, 1,2-distearoyl-sn-glycero-3-phosphocholine, approximately 22 mole percent dihexadecyl phosphate, approximately 16 mole percent cholesterol, and approximately 1 mole percent Biotin DHPE.

Although the invention has been described in terms of specific therapeutic agents and lipids noted above, any of the therapeutic agents described herein may associate with a composition of the invention, comprising any of the combination of lipids disclosed herein.

Covalent Association of Therapeutic and Diagnostic Agents

In embodiments of the invention, a therapeutic or diagnostic agent is covalently attached to a lipid. Examples of lipids to which the therapeutic agents may be attached include, for example, cholesterol, thiocholesterol, MPB-PE, MCC-PE, and 1,2-distearoyl-sn-glycero-3-phosphoethanolamine, and 1,2-dipalmitoyl-sn-glycero-3-phospho-2-mercaptoethanol. Examples of therapeutic agents that may be covalently bound to a lipid include, but are not limited to, poly-peptides and/or proteins, such as, but not limited to, GLP-1, insulin, calcitonin, interferon, uricase, tissue plasminogen activator, thymoglobin, various vaccines, heparin, heparin analogs, antithrombin III, filgrastin, pramilitide acetate, exenatide, epifibatide, and antivenins, blood clotting factors including, but not limited to, Factors VII, VIII, IX, Kallikrein, Kininogen, Hageman Factor (XII), plasma thromboplastin antecedent Factor (XI), tissue factor, Stuart Factor (X), accelerin (V), prothrombin (II), and fibrin stabilizing Factor (XIII); various small molecules, such as, for example, D or L thyroxine or serotonin, nucleic acids, DNA or RNA sequences, immunoglobulins, such as, but not limited to, IgG and IgM, and a variety of monoclonal antibodies, such as but not limited to, rituximab, trastuzumab, and glycolipids that act as therapeutic agents, and in addition, other larger proteins, such as, for example, human growth hormone ("HGH"), erythropoietin, and parathyroid hormone. Various other therapeutic agents have been described elsewhere herein. Each of these therapeutic agents may likewise covalently associate with a composition of the invention.

Examples of diagnostic agents that may be covalently bound to a lipid include diagnostic contrast agents such as, but not limited to, gold, TEMPO (2-diacyl-sn-glycerol-3-phospho-TEMPO-choline), $Fe^{+2}$ oxide, $Fe^{+3}$ oxide, and gadolinium. Other diagnostic agents include radioactive materials such as radioactive isotopes of common atoms including, but not limited to, $^{13}C$, $^{68}Ge$, $^{18}F$, and $^{125}I$. These contrast and radioactive agents may be covalently attached to a lipid or to the optionally present targeting agent. Alternatively, and where chemically appropriate, the diagnostic agent may be bound to a ligand such as DADO (2'-deoxyadenosine), which is itself covalently attached to a lipid or the optional targeting agent. Alternatively, diagnostic agents, such as those described above, may be covalently linked to an antibody or small molecule. These antibodies or small molecules may then associate with a composition of the invention for subsequent oral delivery.

In one embodiment, a therapeutic or diagnostic agent may be directly attached to a lipid. In this embodiment, a free carboxylate or aldehyde on a therapeutic agent is condensed with a lipid bearing an amine using known procedures. Alternatively, the carboxylate may form an ester with a lipid bearing a free alcohol using known esterification procedures. In an alternative embodiment, a free thiol on a therapeutic agent may form a disulfide linkage with a lipid also presenting a free thiol.

More typically, however, a therapeutic agent is attached to a given lipid via a linker. As an example, a therapeutic agent may be attached to a lipid as follows: (therapeutic agent)-N—C(O)(CH$_2$)$_n$S-lipid. In this embodiment, the linker is —C(O)(CH$_2$)$_n$S—. This linker is derived from reaction of a succinimidyl based linker precursor, succinimidyl-O—C(O) (CH$_2$)$_n$SR. Preferably, n is an integer between 1 and 10. Even more preferably, n is 1, 2, or 3. R is typically a protecting group such as —C(O)CH$_3$. Other appropriate thiol protecting groups may be found in *Green's Protective Groups in Organic Synthesis*, Wuts, et al, 4$^{th}$ edition, 2007.

Generally speaking, the linker precursor reacts with a nucleophilic amine, alcohol, or thiol present on the therapeutic agent, displacing N-hydroxysuccinimide, to form an amide, ester, or thioester. Preferably, the nucleophile is a primary amine. After the linker is bound to the therapeutic agent, the protecting group, R, is removed from the linker to reveal a thiol. Preferably, the protecting group is removed under conditions that do not perturb the now attached therapeutic agent. This thiol may then undergo a Michael reaction with a lipid such as MPB-PE or MCC-PE. Preferably, lipids MPB-PE and/or MCC-PE are already incorporated into a composition of the invention, however, the Michael reaction may take place pior to incorporating these lipids into a composition of the invention. The order of reactions will depend upon the therapeutic agent's ability to tolerate microfluidization, aqueous environments, and elevated temperatures. In the case of complex proteins which may denature at high temperatures, it is preferable to perform the Michael reaction after MPB-PE and/or MCC-PE have been incorporated into a composition of the invention.

Additional linker precursors that may be used include compounds according to formula I:

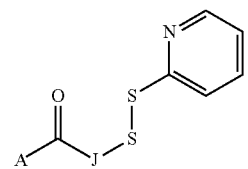

I wherein "A" corresponds to

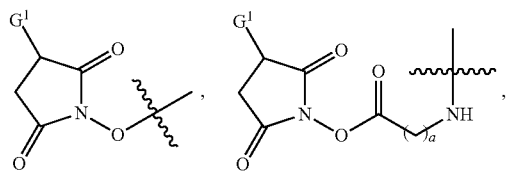

or NH$_2$NH—; "J" corresponds to (CH$_2$)$_a$ or

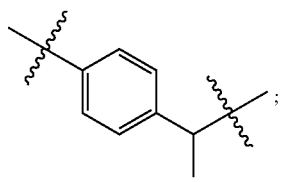 [SMILES: *c1ccc(C(*)C)cc1]

and G$^1$ is either H or SO$_3$Na. Subscript "a" is independently, at each occurrence, 1, 2, 3, 4, 5, 6, 7, or 8. Common examples of linker precursors according to formula I include, but are not limited to, N-succinimidyl-3-(2-pyridyldithio) proprionate ("SPDP"), Succinimidyl 6-(3-[2-pyridyldithio]-propionamido)hexanoate ("LC-SPDP"), Sulfosuccinimidyl 6-(3'-[2-pyridyldithio]-propionamido)hexanoate ("Sulfo-LC-SPDP"), 4-Succinimidyloxycarbonyl-methyl-a-[2-pyridyldithio]toluene ("SMPT"), 4-Sulfosuccinimidyl-6-methyl-a-(2-pyridyldithio)toluamido]hexanoate) ("Sulfo-LC-SMPT"), and 3-(2-pyridyldithio)propionyl hydrazide ("PDPH"), each of which are known and described in the literature.

When a compound of formula I is used (and "A" is not NH$_2$NH) a free nitrogen on a therapeutic agent reacts with the compound of formula I to form an amide bond by displacing N-hydroxysuccinimide or a related derivative. Subsequently, the disulfide bridge present in the linker precursor is reduced under mild conditions using tris(2-carboxyethyl)phosphine (TCEP) or other known reducing agents. The resulting free thiol can then react with a lipid such as MPB-PE or MCC-PE, either before or after the lipid is incorporated into a composition of the invention. Preferably, the resulting free thiol is reacted with the lipid after the lipid has been incorporated into a composition of the invention.

Alternatively, a compound of formula I may react with a nucleophile such as 1,2-distearoyl-sn-glycero-3-phosphethanolamine, or related derivative, to displace succinimide. The disulfide in the resulting product may then be reduced using TCEP or other mild reductant to provide a free thiol. The resulting thiol compound may then be oxidatively coupled to a free thiol in a therapeutic agent. Preferably, the resulting free thiol is reacted with the therapeutic agent after the lipid has been incorporated into a composition of the invention, however it need not be, depending upon the stability of the therapeutic agent.

When A is $NH_2NH-$, the nucleophilic nitrogen of the hydrazide reacts with a ketone, aldehyde, activated ester, a carboxylic acid, or leaving group on a therapeutic agent to form a therapeutic agent/linker conjugate. When reacting with an aldehyde or ketone, the reaction is typically a reductive amination, but may be a simple condensation without concomitant reduction, resulting in the formation of an enamine. When the hydrazide reacts with a carboxylic acid to form a hydrazone, the reaction is mediated by a crosslinking reagent, such as EDC, EDCI, or other crosslinking reagent now known or hereafter developed.

As above, the disulfide bridge is then reduced under mild conditions. The resulting free thiol can then react with a lipid such as MPB-PE or MCC-PE, either before or after the lipid is incorporated into a composition of the invention. Preferably, the resulting free thiol is reacted with the lipid after the lipid has been incorporated into the composition.

In another embodiment, the linker precursor may be a compound according to formula II

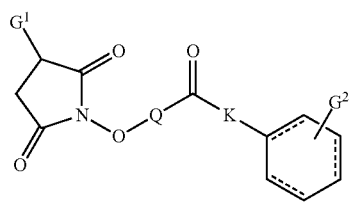

II wherein $G^1$ is either H or $SO_3Na$; $G^2$ is maleimidyl,

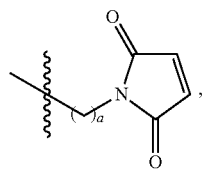

$-HNC(O)CH_2I$, $-CH_2NHC(O)(CH_2)_aNHC(O)CH_2I$, $-CH_2HNC(O)CH_2I$; "Q" is optional and, when present, is $-C(O)(CH_2)_aNH-$; "K" is optional, and when present, is $-(CH_2)_a-$; and "a," as used in formula II, "Q", or "K" is independently, at each occurrence 1, 2, 3, 4, 5, 6, 7, or 8. When "A" is not present, the oxygen of the N-hydroxysuccinimidyl group is bound directly to the carbon of the carbonyl adjacent to "A".

In formula II, the bond notation "═" indicates that the bond may be a single or a double bond. Preferably, when one bond according to the above described notation represents a double bond, all bonds according to that notation represent double bonds. Similarly, if any bond according to the above described notation represents a single bond, it is preferred that all bonds according to that notation represent a single bond.

Common examples of linker precursors according to formula II include, but are not limited to, Succinimidyl 4-[N-maleimidomethyl]cyclohexane-1-carboxylate ("SMCC"), Sulfosuccinimidyl 4-[N-maleimidomethyl]cyclohexane-1-carboxylate ("Sulfo-SMCC"), m-Maleimidobenzoyl-N-hydroxysuccinimide ester ("MBS"), m-Maleimidobenzoyl-N-hydroxysulfosuccinimide ester ("Sulfo-MBS"), N-Succinimidyl[4-iodoacetyl]aminobenzoate ("SIAB"), N-Sulfosuccinimidyl[4-iodoacetyl]aminobenzoate ("Sulfo-SIAB"), succinimidyl-4-(((iodoacetyl)amino)methyl)cyclohexane-1-carboxylate ("SIAC"), succinimidyl 4-[p-maleimidophenyl]butyrate ("SMPB"), sulfosuccinimidyl 4-[p-maleimidophenyl]butyrate ("Sulfo-SMPB"), and succinimidyl-6-((((4-(iodoacetyl)amino)methyl)cyclohexane-1-carbonyl)amino)-hexanoate ("SIACX"), each of which are known and described in the literature.

When a compound of formula II is used, a free nitrogen on a therapeutic agent reacts with the compound of formula II to form an amide bond by displacing N-hydroxysuccinimide or sulfo-N-hydroxysuccinimide. The resulting therapeutic agent/linker conjugate is then preferably reacted with a composition of the invention containing a lipid bearing a free thiol (such as, for example, thiocholesterol or 1,2-dipalmitoyl-sn-glycero-3-phospho-2-mercaptoethanol). The free thiol undergoes a Michael reaction into the double bond of a maleimide group, or displaces I$^-$ in a displacement reaction. Although it is preferred that the therapeutic agent/linker conjugate is reacted with a lipid presenting a free thiol that has already been incorporated into a composition of the invention, the therapeutic agent/linker conjugate may be reacted with a lipid presenting a free thiol prior to the lipid being incorporated into a composition of the invention.

In another embodiment, the linker precursor may be a compound according to formula III

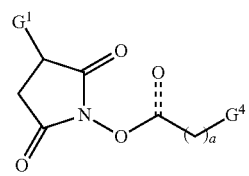

III wherein $G^1$ is either H or $SO_3Na$, $G^4$ is maleimidyl, $-HNC(O)CH_2I$, or $NHC(O)(CH_2)_aNHC(O)CH_2I$ and "a" is, independently at each occurrence, 1, 2, 3, 4, 5, 6, 7, or 8. A double dashed bond connected to an oxygen indicates that a given carbon is optionally a carbonyl. Thus, in formula III, the double dashed bond connected to the noted carbon indicates that the bond connectivity at that carbon is $-C(O)-$ or $-CH_2-$. Common examples of linker precursors according to formula III include, but are not limited to, N-[g-maleimidobutyryloxy]succinimide ester ("GMBS"), N-[g-maleimidobutyryloxy]sulfosuccinimide ester ("Sulfo-GMBS"), succinimidyl-6-((iodoacetyl)amino) hexanoate ("SIAX"), and succinimidyl-6-(6-(((iodoacetyl) amino)hexanoyl)amino)hexanoate ("SIAXX"), each of which are known and described in the literature.

When a compound of formula III is used, a free nitrogen on a therapeutic agent reacts with the compound of formula III to form an amide bond by displacing N-hydroxysuccinimide or sulfo-N-hydroxysuccinimide. The resulting therapeutic agent/linker conjugate is then preferably reacted with a composition of the invention containing a lipid bearing a free thiol (such as, for example, thiocholesterol or 1,2-dipalmitoyl-sn-glycero-3-phospho-2-mercaptoethanol). The free thiol undergoes a Michael reaction into the double bond of a maleimide group, or displaces I⁻ in a displacement reaction. Although it is preferred that the therapeutic agent/linker conjugate is reacted with a lipid presenting a free thiol that has already been incorporated into a composition of the invention, the therapeutic agent/linker conjugate may be reacted with a lipid presenting a free thiol prior to the lipid being incorporation into a composition of the invention.

In another embodiment, the linker precursor may be compounds according to formula IV

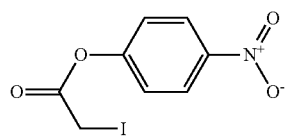

IV

When a compound of formula IV is used, a free nitrogen on a therapeutic agent reacts with the compound of formula IV to form an amide bond by displacing the p-nitrophenyl group. The resulting therapeutic agent/linker conjugate is then preferably reacted with a composition of the invention containing a lipid bearing a free thiol (such as, for example, thiocholesterol or 1,2-dipalmitoyl-sn-glycero-3-phospho-2-mercaptoethanol). The free thiol displaces I⁻ in a displacement reaction. Although it is preferred that the therapeutic agent/linker conjugate is reacted with a lipid presenting a free thiol that has already been incorporated into a composition of the invention, the therapeutic agent/linker conjugate may be reacted with a lipid presenting a free thiol prior to the lipid being incorporated into a composition of the invention.

In a further embodiment, the linker precursor is a compound of formula V.

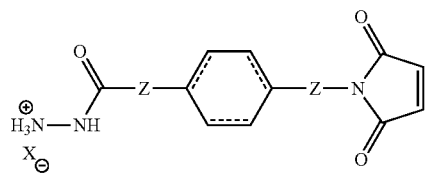

V

In formula V, "Z" is independently optional at each occurrence, and when present is $(CH_2)_a$. Subscript "a" is independently, at each occurrence, 1, 2, 3, 4, 5, 6, 7, or 8. Although structure V is shown as the salt, compounds of formula V may be either a salt or a free base. Examples of linker precursors according to formula V include, but are not limited to, 4-(4-N-Maleimidophenyl)butyric acid hydrazide hydrochloride ("MBPH") and 4-(N-maleimidophenyl)cyclohexane-1-carbonyl-hydrazide hydrochloride ("$M_2C_2H$"). In formula V, the bond notation "=" indicates that the bond may be a single or a double bond. Preferably, when one bond according to the above described notation represents a double bond, all bonds according to that notation represent double bonds. Similarly, if any bond according to the above described notation represents a single bond, it is preferred that all bonds according to that notation represent a single bond.

When a compound of formula V is used, the nucleophilic nitrogen of the hydrazide reacts with a ketone, aldehyde, activated ester, a carboxylic acid, or leaving group on a therapeutic agent to form a therapeutic agent/linker conjugate. When reacting with an aldehyde or ketone, the reaction is typically a reductive amination. The reaction may, however, be a simple condensation without concomitant reduction, resulting in the formation of an enamine. When the hydrazide is reacted with a carboxylic acid, the reaction is mediated by a crosslinking reagent, such as EDC (1-ethyl-3,3-dimethylaminopropylcarbodiimide), EDCI (1-(3-dimethylaminopropyl)-3-ethylcarboiimide), or other crosslinking reagent now known or hereafter developed.

The resulting therapeutic agent/linker conjugate is then preferably reacted with a composition of the invention containing a lipid bearing a free thiol (such as, for example, thiocholesterol or 1,2-dipalmitoyl-sn-glycero-3-phospho-2-mercaptoethanol). The free thiol undergoes a Michael reaction into the double bond of the maleimide portion of the conjugate. Although it is preferred that the therapeutic agent/linker conjugate is reacted with a lipid presenting a free thiol that has already been incorporated into a composition of the invention, the therapeutic agent/linker conjugate may be reacted with a lipid presenting a free thiol prior to the lipid being incorporated into a composition of the invention.

In a further embodiment, the linker precursor may be a compound according to formula VI:

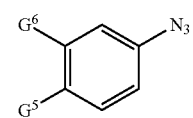

VI wherein $G^5$ is selected from the group consisting of —C(O)G⁷, —C(O)NHNH₂, —C(O)C(O)H, —C(O)NH(CH₂)ₐNH₂, —C(O)NH(CH₂)ₐNHC(O)CH₂I, —C(O)NH(CH₂)ₐC(O)G⁷, —NO₂, —(CH₂)ₐNHC(O)G⁷, —NH(CH₂)ₐC(O)G⁷, —(CH₂)ₐSSC(O)G⁷, —C(O)NH(CH₂)ₐSS(CH₂)ₐC(O)G⁷, —(CH₂)ₐC(O)G⁷, and —C(O)NH(CH₂)ₐNHC(O)(CH₂)ₐG⁹; "a" is independently at each occurrence 1, 2, 3, 4, 5, 6, 7, or 8; and $G^6$ is selected from the group consisting —OH, —NO₂, —H, and —C(O)G⁷. $G^7$ is

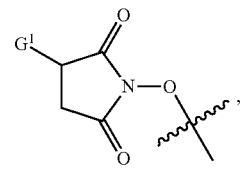

wherein $G^1$ is either H or —SO$_3$Na; provided that $G^6$ is —C(O)$G^7$ only when $G^5$ is —NO$_2$ and that $G^5$ is —NO$_2$ only when $G^6$ is —C(O)$G^7$. $G^9$ is

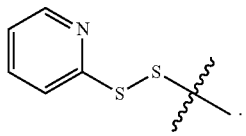 [SMILES: *SSc1ccccn1]

Examples of linkers according formula VI include, but are not limited to, N-Hydroxysuccinimidyl-4-azidosalicylic acid ("NHS-ASA"), N-hydroxysulfosuccinimidyl-4-azidosalicylic acid ("Sulfo-NHS-ASA"), sulfosuccinimidyl[4-azidosalicylamido]-hexanoate ("Sulfo-NHS-LC-ASA"), N-hydroxysuccinimidyl-4-azidobenzoate ("HSAB"), N-hydroxysulfosuccinimidyl-4-azidobenzoate ("Sulfo-HSAB"), N-5-azido-2-nitrobenzoyloxysuccinimide ("ANB-NOS"), N-succinimidyl-6-(4'-azido-2'-nitrophenylamino) hexanoate ("SANPAH"), N-sulfosuccinimidyl-6-(4'-azido-2'-nitrophenylamino) hexanoate ("Sulfo-SANPAH"), N-succinimidyl(4-azidophenyl)-1,3'-dithiopropionate ("SADP"), N-Sulfosuccinimidyl(4-azidophenyl)-1,3'-dithiopropionate ("Sulfo-SADP"), sulfosuccinimidyl-2-(p-azidosalicylamido)-ethyl-1,3'-dithiopropionate ("SASD"), 1-(p-azidosalicylamido)-4-(iodoacetamido)butane ("ASIB"), N-[4-(p-azidosalicylamido) butyl]-3"-(2"-pyridyldithio)propionamide ("APDP"), p-azidobenzoyl hydrazide ("ABH"), 4-[p-azidosalicylamido]butylamine ("ASBA"), p-azidophenyl glyoxal ("APG"), and sulfosuccinimidyl-4-(p-azidophenyl)butyrate ("Sulfo-SAPB"), each of which are known and described in the literature.

Linker precursors according to formula VI may be used in various ways. In an example of a first method of attachment wherein $G^5$ or $G^6$ is a group containing $G^7$, a free nitrogen on an therapeutic agent reacts with the linker precursor giving a therapeutic agent/linker conjugate by displacing N-hydroxysuccinimide or sulfo-N-hydroxysuccinimide. The resulting conjugate is then irradiated with UV light in the presence of a substantial excess of a lipid. The UV light induces nitrene formation. This nitrene subsequently reacts with the lipid in a non-selective manner to form a therapeutic agent/linker/lipid conjugate. This conjugate can then be incorporated into a composition of the invention.

In an alternative process, a therapeutic agent/linker conjugate may be irradiated with UV light in the presence of a composition of the invention. The UV light induces nitrene formation. This nitrene can then react with any lipid present in the composition.

In another embodiment, the linker precursor according to formula VI may be irradiated in the presence of a lipid or a composition of the invention prior to reaction with a therapeutic agent. This process results in the formation of a lipid/linker conjugate or a composition/linker conjugate. The lipid/linker conjugate is subsequently incorporated into a composition of the invention according to the procedures set forth elsewhere herein. The composition/linker conjugate may then be reacted with a therapeutic agent presenting a nucleophilic nitrogen according to the displacement chemistry described previously herein.

When $G^5$ in formula VI is a group containing a nucleophilic nitrogen, this nucleophilic nitrogen may react with a ketone, aldehyde, activated ester, a carboxylic acid, or leaving group on a therapeutic agent to form a therapeutic agent/linker conjugate. When reacting with an aldehyde or ketone, the reaction is typically a reductive amination. The reaction may, however, be a simple condensation without concomitant reduction, resulting in the formation of an enamine. When the nucleophilic nitrogen reacts with a carboxylic acid, the reaction is mediated by a crosslinking reagent, such as EDC, EDCI, or other crosslinking reagent now known or hereafter developed.

The resulting therapeutic agent/linker conjugate is then preferably irradiated with UV light in the presence of a substantial excess of a lipid, as described above, to form a therapeutic agent/linker/lipid conjugate. This conjugate can then be incorporated into a composition. In an alternative procedure, the therapeutic agent/linker conjugate may be irradiated in the presence of composition of the invention.

In yet another embodiment, the linker precursor of formula VI may be irradiated in the presence of a lipid or a composition of the invention prior to reaction with a therapeutic agent. This process results in the formation of a lipid/linker conjugate or a composition/linker conjugate. The lipid/linker conjugate is subsequently incorporated into a composition of the invention according to the procedures set forth elsewhere herein. The composition/linker conjugate may then be reacted with a therapeutic agent with a nucleophilic nitrogen according to the displacement chemistry described previously.

In an alternative embodiment, a linker precursor according to formula VI may be irradiated and reacted with a therapeutic agent to form a therapeutic agent/linker conjugate. When the conjugate contains a group according to $G^7$, the conjugate may then be reacted with a compound such as 1,2-distearoyl-sn-glycero-3-phosphoethanolamine, wherein the free nitrogen of the ethanolamine reacts with the activated hydroxy succinimidyl ester of $G^7$. If the conjugate contains a "CH$_2$I" functionality, the conjugate may be reacted with a lipid such as thiocholesterol. If the conjugate contains a disulfide, this disulfide may be selectively reduced, whereupon the resulting free thiol bound to the conjugate may react with a compound such as MPB-PE or MCC-PE. Preferably, the lipids used to bind the therapeutic agent/linker conjugate have already been incorporated into a composition of the invention.

In any of the above described procedures, the order of reactions and the choice of coupling partner will be determined by the stability of the therapeutic agent under a particular set of reaction conditions. It is within the skill of the ordinarily skilled artisan to determine the appropriate order of reactions to arrive at the desired bond connectivity.

In a further embodiment, the linker precursor may be a compound according to formula VII or VIII:

VII
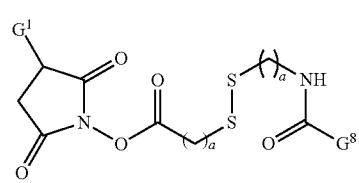

VIII
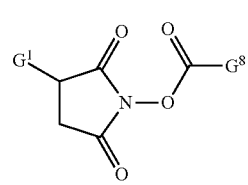

wherein $G^1$ is either H or $SO_3Na$ and $G^8$ is selected from the group consisting of 2-nitrophenyl-5-azido and

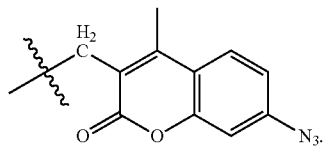

Subscript "a" is independently, at each occurrence, 1, 2, 3, 4, 5, 6, 7, or 8. Examples of compounds according to formula VII and VIII include, but are not limited to, sulfosuccinimidyl-2-(m-azido-o-nitrobenzamido)-ethyl-1,3'-proprionate ("SAND"), sulfosuccinimidyl 2-[7-amino-4-methylcoumarin-3-acetamido]ethyl-1,3'dithiopropionate ("SAED"), and sulfo-succinimidyl 7-azido-4-methylcoumarin-3-acetate ("Sulfo-SAMCA"). Linker precursors according to formula VII and VIII may be utilized in substantially the same ways as described with respect to linker precursors of formula VI.

In a further embodiment, the linker precursor may be a compound according to formula IX:

IX

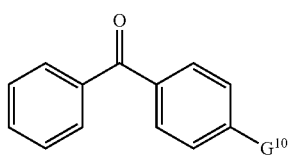

wherein $G^{10}$ is selected from the group consisting of maleimidyl and $NC(O)CH_2I$. Examples of linker precursors according to formula IX include, but are not limited to, benzophenone-4-iodoacetamide and benzophenone-4-maleimide. When using a linker precursor of formula IX, the free thiol of thiocholesterol displaces $I^-$ in a displacement reaction to form a linker/lipid conjugate. Subsequently, the linker/lipid conjugate is irradiated with UV light in the presence of a therapeutic agent to form a therapeutic agent/linker/lipid conjugate. This compound may then be incorporated into a composition of the invention.

In a further embodiment, the linker precursor may be a compound according to formula X:

X

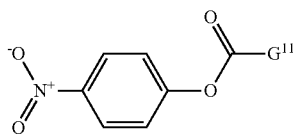

wherein $G^{11}$ is selected from the group consisting of $C(O)C(N_2)H$ and $C(N_2)CF_3$. When a linker precursor according to formula X is used, the linker precursor is first reacted with a therapeutic agent containing a free primary amine in order displace p-nitrophenol. This results in a therapeutic agent/linker conjugate. Subsequently, the conjugate is irradated to form a carbene. When $G^{11}$ is $C(O)C(N_2)H$, the conjugate is irradiated in the presence of a compound containing a nucleophilic amine, such as, for example, 1,2-distearoyl-sn-glycero-3-phosphoethanolamine. When $G^{11}$ is $C(N_2)CF_3$, the conjugate is irradiated in the presence of lipid or a composition of the invention.

Alternatively, the compound according to Formula X may first be reacted with a lipid such as 1,2-distearoyl-sn-glycero-3-phosphoethanolamine to displace p-nitrophenol and then irridated to form a carbene. When $G^{11}$ is $C(O)C(N_2)H$, the conjugate is irradiated in the presence of a therapeutic agent containing a nucleophilic amine. When $G^{11}$ is $C(N_2)CF_3$, the conjugate is irradiated in the presence of a therapeutic agent.

As with other reactions described herein, the order of reactions and the choice of coupling partner will be determined by the stability of the therapeutic agent under a particular set of reaction conditions. It is within the skill of the ordinarily skilled artisan to determine the appropriate order of reactions to arrive at the desired bond connectivity.

RES Masking and Avoidance

In addition to an optional targeting molecule, the composition of the invention may further include a reticuloendothelial sytem (RES) avoidance molecule. The RES avoidance molecule gives the composition a longer half life in the systemic circulation by shielding the composition from macrophage detection.

RES avoidance molecules may be incorporated into a composition of the invention by binding to a lipid comprising the composition of the invention. For example, U.S. Pat. No. 6,177,099 describes a process wherein ß-methoxy neuraminic acid was modified to contain a free thiol that was subsequently reacted with MPB-PE via a Michael reaction, as shown in Scheme 1.

Scheme 1

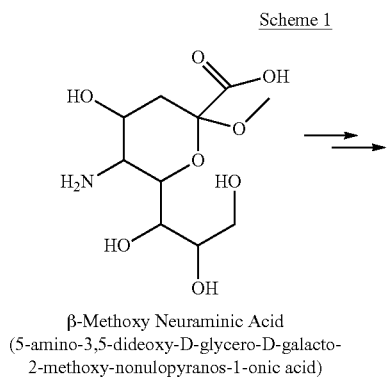

β-Methoxy Neuraminic Acid
(5-amino-3,5-dideoxy-D-glycero-D-galacto-
2-methoxy-nonulopyranos-1-onic acid)

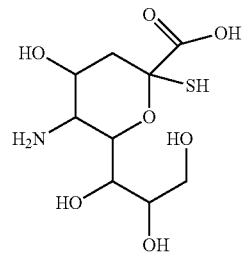

Along with the incorporation of neuraminic acid as described above, the present invention further contemplates the incorporation of other novel neuraminic acid derivatives. These novel derivatives include, but are not limited to the following N-acyl neuraminic acid derivatives:

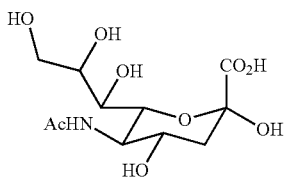

5-acetamido-3,5-dideoxy-D-glycerol-D-galacto-2-nonulopyranose-1-onic acid ("N-acetylneuraminic acid")

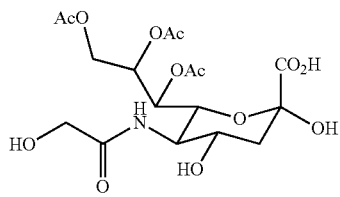

5-glycolamido-7,8,9-tri-O-acetyl-3,5-dideoxy-D-glycerol-D-galacto-2-nonulopyranose-1-onic acid ("7,8,9-tri-O-acetyl-N-glycolneuraminic acid")

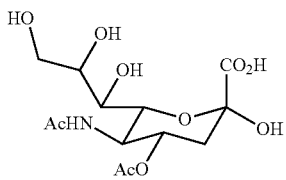

5-acetamido-4-O-acetyl-3,5-dideoxy-D-glycerol-D-galacto-2-nonulopyranose-1-onic acid ("N-acetyl-4-O-acetylneuramic acid")

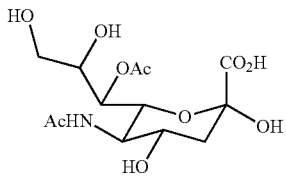

5-acetamido-7-O-acetyl-3,5-dideoxy-D-galacto-2-nonulopyranose-1-onic acid ("N-acetyl-7-O-acetylneuraminic acid")

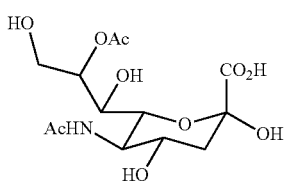

5-acetamido-8-O-acetyl-3,5,-dideoxy-D-glycerol-D-galacto-2-nonulopyranose-1-onic acid ("N-acetyl-8-O-acetylneuraminic acid")

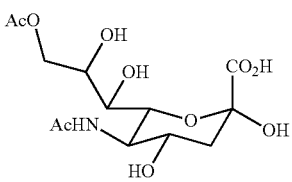

5-acetamido-9-O-acetyl-3,5,-dideoxy-D-glycerol-D-galacto-2-nonulopyranose-1-onic acid ("N-acetyl-9-O-acetylneuraminic acid")

-continued

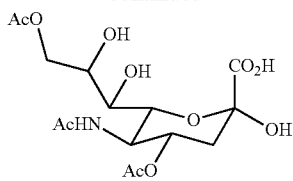

5-acetamido-4,9-di-O-acetyl-3,5,-dideoxy-D-glycerol-D-galacto-2-nonulopyranose-1-onic acid ("N-acetyl-4, 9-O-diacetylneuraminic acid")

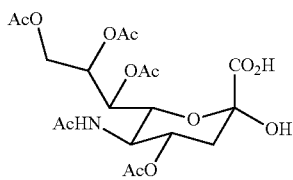

5-acetamido-7,9-di-O-acetyl-3,5,-dideoxy-D-glycerol-D-galacto-2-nonulopyranose-1-onic acid ("N-acetyl-7, 9-O-diacetylneuraminic acid")

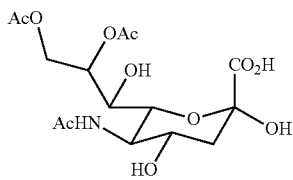

5-acetamido-8,9-di-O-acetyl-3,5,-dideoxy-D-glycerol-D-galacto-2-nonulopyranose-1-onic acid ("N-acetyl-8,9-di-O-acetylneuraminic acid")

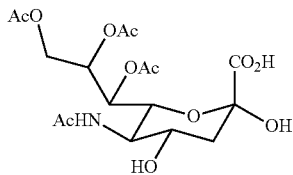

5-acetamido-7,8,9-tri-O-acetyl-3,5,-dideoxy-D-glycerol-D-galacto-2-nonulopyranose-1-onic acid ("N-acetyl-7,8,9-tri-O-acetylneuraminic acid")

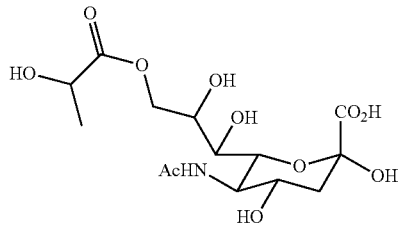

5-acetamido-9-O-lactyl-3,5,-dideoxy-D-glycerol-D-galacto-2-nonulopyranose-1-onic acid ("N-acetyl-9-O-L-lactylneuraminic acid")

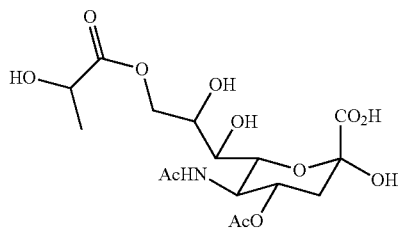

5-acetamido-4-O-acetyl-9-O-lactyl-3,5,-dideoxy-D-glycerol-D-galacto-2-nonulopyranose-1-onic acid ("N-acetyl-4-O-acetyl-9-O-lactylneuraminic acid")

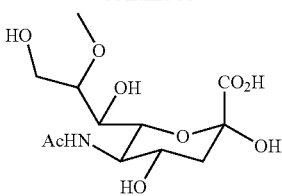

5-acetamido-8-O-methyl-3,5-dideoxy-D-glycerol-D-galacto-2-nonulopyranose-1-onic acid ("N-acetyl-8-O-methylneuraminic acid")

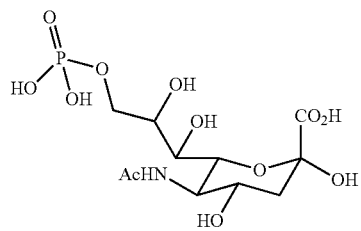

5-acetamido-9-O-phosphono-3,5-dideoxy-D-glycerol-D-galacto-2-nonulopyranose-1-onic acid ("N-acetyl-9-O-phosphononeuraminic acid")

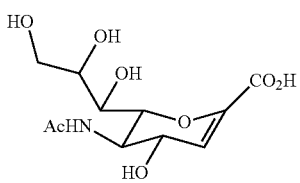

5-acetamido-2,6-anhydro-3,5-dideoxy-D-glycerol-D-galacto-2-nonulopyranose-1-onic acid

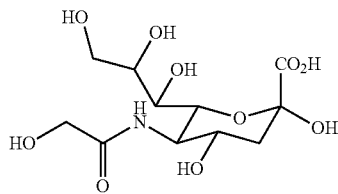

5-glycolamido-3,5-dideoxy-D-glycerol-D-galacto-2-nonulopyranose-1-onic acid ("glycolylneuraminic acid")

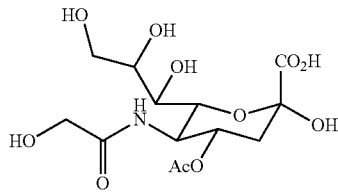

5-glycolamido-4-O-acetyl-3,5-dideoxy-D-glycerol-D-galacto-2-nonulopyranose-1-onic acid ("4-O-acetyl-N-glycolylneuraminic acid")

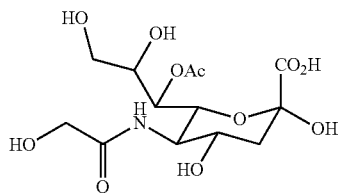

5-glycolamido-7-O-acetyl-3,5-dideoxy-D-glycerol-D-galacto-2-nonulopyranose-1-onic acid ("7-O-acetyl-N-glycolylneuraminic acid")

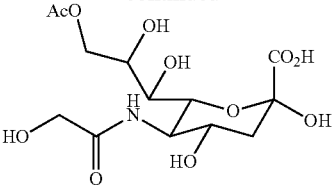

5-glycolamido-9-O-acetyl-3,5-dideoxy-D-glycerol-D-galacto-2-nonulopyranose-1-onic acid ("9-O-acetyl-N-glycolylneuraminic acid")

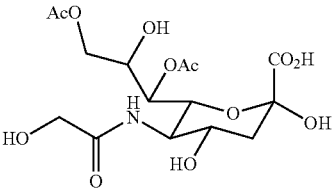

5-glycolamido-7,9-di-O-acetyl-3,5-dideoxy-D-glycerol-D-galacto-2-nonulopyranose-1-onic acid ("7,9-di-O-acetyl-N-glycolylneuraminic acid")

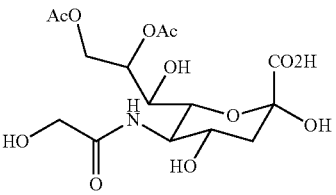

5-glycolamido-8,9-di-O-acetyl-3,5-dideoxy-D-glycerol-D-galacto-2-nonulopyranose-1-onic acid ("8,9-di-O-acetyl-N-glycolylneuraminic acid")

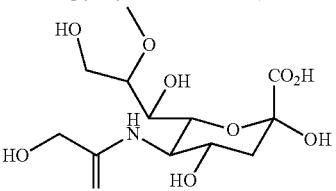

5-glycolamido-8-O-methyl-3,5-dideoxy-D-glycerol-D-galacto-2-nonulopyranose-1-onic acid ("N-glycolyl-8-O-methylneuraminic acid")

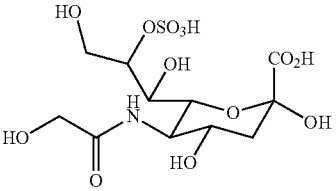

5-glycolamido-8-O-sulfo-3,5-dideoxy-D-glycerol-D-galacto-2-nonulopyranose-1-onic acid ("N-glycolyl-8-O-sulfoneuraminic acid")

α-2-8-poly-N-acetyl-neuraminic acid (colominic acid) and derivatives thereof

Although not shown, further examples of neuraminic acid derivatives include those in which the nitrogen is not acylated.

The above described neuraminic acid derivatives may be linked to a lipid of the invention via various methodologies. In one embodiment, an N-acyl neuraminic acid derivative containing a 1,2 diol functionality may be cleaved to an aldehyde using $NaIO_4$ under known conditions. The resulting aldehyde may then undergo reductive amination with the primary amine of a lipid such as 1,2-distearoyl-sn-glycero- 3-phosphoethanolamine according to known procedures. An example of this chemistry is shown in Scheme 2.

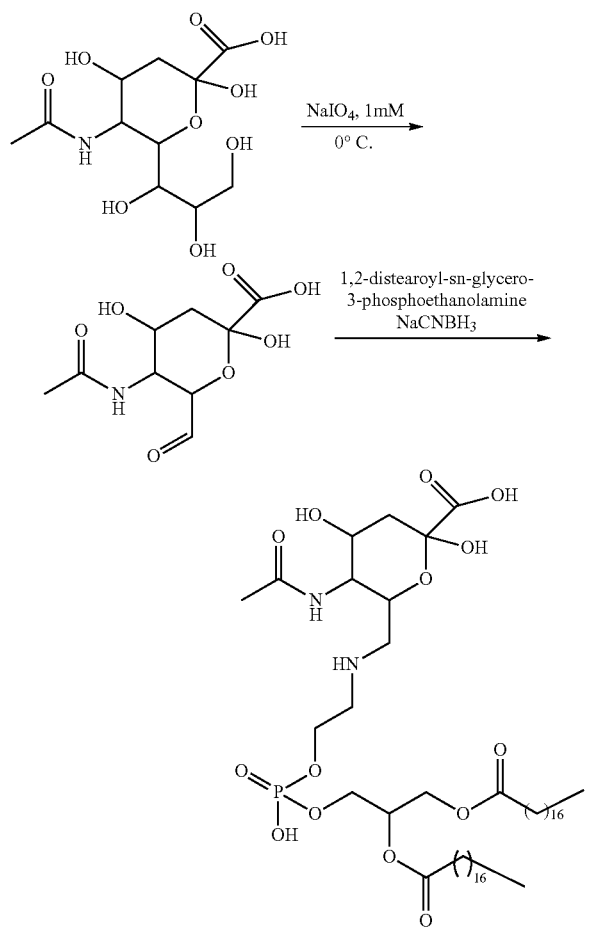

In an alternative embodiment, an N-acyl neuraminic acid derivative may be reacted with a phosgene equivalent such as N,N'-disuccinimidylcarbonate (DSC). In this embodiment, an alcohol on the neuraminic acid derivative reacts with DSC to produce an intermediate containing an activated carbonyl. This intermediate can then be reacted with a lipid presenting a free primary or secondary amine. A non-limiting example of an amine bearing lipid is 1,2-distearoyl-sn-glycero-3-phosphoethanolamine.

In a further embodiment, cholesterol may react with DSC to form intermediate that may be subsequently reacted with neuraminic acid derivative presenting a free amine.

In still another embodiment, a neuraminic acid derivative presenting a free amine may be condensed with formaldehyde to generate an iminium, which may be quenched by nucleophilic attack at the formaldehyde carbon with an appropriate nucleophile. Appropriate nucleophiles include primary and secondary amines, an example of which includes, but is not limited to, 1,2-distearoyl-sn-glycero-3-phosphoethanolamine.

As discussed elsewhere herein, RES masking agents may also be associated with a composition of the invention via non-covalent interactions. In the non-covalent embodiment, up to about 10 mole percent of the composition may comprise one or more RES masking agents.

Stability

Although a composition of the invention is formulated in aqueous media, the composition does not exhibit long term stability in water. Specifically, water aids hydrolysis of any acyl chains present in any of the lipids present in the composition. The aqueous environment also allows for the ready oxidation of any unsaturated acyl chains present in any of these lipids. In a preferred embodiment of the present invention, the composition of the present invention may be protected for long term storage via interaction with a proteoglycan such as a modified collagen, known generically as dry granulated gelatin. Dry granulated gelatin, when contacted with an aqueous suspension of a composition of the invention, reacts with the water, and stabilizes the composition.

The reaction of dried granulated gelatin with an aqueous suspension of a composition of the present invention results in a semi-solid colloidal gel that shields the composition from direct interaction with water. Any water not associated with gelatin is slowly evaporated via refrigerated storage at about 2° to about 8° C. The water may, however, be removed via techniques including, but not limited to, freeze drying and spray drying.

This results in a pellet like "dry" composition/gelatin complex. In the complex, the composition of the invention is partially dehydrated in a reversible manner and sequestered by the proteinaceous lattice of dry gelatin. This sequestration is enabled by structured water, structured lipid and structured gelatin all interacting through hydrogen bonding, ionic bonding, van der Waal's interactions, and hydrophobic bonding between the lipids, water, and protein structures, such as, for example, insulin. This evidences that gelatin is not acting as an emulsifying or suspending agent. As a result, the "dry" pellet is stable for long term storage because the activity of water has been mitigated. These pellets can be further processed to a granulated or free-flowing powder for final capsule filling or tabletting, while maintaining their stability.

Upon oral administration to a patient, the "dry" pellet becomes hydrated and once again assumes a semi-solid colloidal gel state. Upon further exposure to the gastric environment, the gel becomes liquid as gelatin is solubilized. Once the gelatin is completely solubilized, the composition of the invention rehydrates, resulting in the formation of a new suspension within the gastric environment. The reconstituted composition may then be absorbed into the portal blood flow.

It is important to realize that the role of gelatin in this aspect of the invention is as an active stabilizer of the composition and not an inert filler as is commonly found in oral formulations of many other pharmaceutical compositions. That said, the additional use of gelatin as an inert filler in addition to the aforementioned use is also contemplated.

Although gelatin is used in a preferred embodiment of the invention, other gelatin like compounds may be used as well. Examples of agents that will act as active stabilizers include, but are not limited to, acacia (gum arabic), agar (agar-agar; vegetable gelatin; gelosa; Chinese or Japanese gelatin), alginic acid, sodium alginate (alginic acid; sodium salt; algin; Manucol; Norgine; Kelgin), carbomer (carboxypolymethylene), carrageenan, carboxymethylcellulose sodium (carbose D; carboxymethocel S; CMC; cellulose gum), powdered cellulose (Degussa), hydroxyethyl cellulose (cellulose; 2-hydroxyethyl ether; Cellosize; Natrosol), hydroxypropyl cellulose (cellulose; 2-hydroxypropyl ether; Klucel), hydroxypropyl methylcellulose (cellulose; 2-hydroxypropyl methyl ether), methylcellulose (cellulose;

methyl ether Methocel), povidone (2-pyrrolidinone; 1-ethenyl-; homopolymer; polyvinylpyrrolidone), tragacanth (gum tragacanth; Hog Gum; Goat's Thorn), and xanthan gum (Keltrol). Like gelatin, and where appropriate, these compounds may also be used as inert fillers.

Formulations

A formulation of a composition of the invention and therapeutic agent (with or without the targeting agent)—hereinafter "composition"—for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, aqueous suspensions, or emulsions.

A tablet comprising the composition of the present invention, for example, be made by compressing or molding the composition optionally with one or more additional ingredients. Compressed tablets may be prepared by compressing, in a suitable device, the composition in a free-flowing form such as a powder or granular preparation, optionally mixed with one or more of a binder, a lubricant, an excipient, a surface active agent, and a dispersing agent. Molded tablets may be made by molding, in a suitable device, the composition, a pharmaceutically acceptable carrier, and at least sufficient liquid to moisten the mixture.

Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the composition. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the composition may be made using a physiologically degradable composition, such as gelatin. Such hard capsules comprise the active ingredient, and may further comprise additional ingredients including, for example, an inert solid diluent such as calcium carbonate, calcium phosphate, kaolin or cellulose acetate hydrogen phthalate.

Soft gelatin capsules comprising the composition may be made using a physiologically degradable composition, such as gelatin.

Liquid formulations of the composition which are suitable for oral administration may be prepared, packaged, and sold either in liquid form or in the form of a dry product intended for reconstitution with water or another suitable vehicle prior to use, subject to the stability limitations disclosed earlier.

Liquid suspensions may be prepared using conventional methods to achieve suspension of the constituents in an aqueous vehicle. Aqueous vehicles include, for example, water and isotonic saline. Oily vehicles may only be used to the extent that such solvents are not incompatible with the constituents of the composition of the present invention. To the extent that an oily suspension is not incompatible with the constituents of the composition of the present invention, an oily suspension may further comprise a thickening agent.

Liquid suspensions may further comprise one or more additional ingredients to the extent that said ingredients do not disrupt the structures of the constituents of the composition of the invention. Examples of additional ingredients include, but are not limited to, suspending agents, dispersing or wetting agents, emulsifying agents, demulcents, preservatives, buffers, salts, flavorings, coloring agents, and sweetening agents.

Known suspending agents include, but are not limited to, sorbitol syrup, sodium alginate, polyvinylpyrrolidone, gum tragacanth, gum acacia, and cellulose derivatives such as sodium carboxymethylcellulose, methylcellulose, hydroxypropylmethylcellulose.

Known emulsifying agents include, but are not limited to acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin.

Powdered and granular formulations of a pharmaceutical preparation of the invention may be prepared using known methods. Such formulations may be administered directly to a subject, used, for example, to form tablets, to fill capsules, or to prepare an aqueous suspension or solution by addition of an aqueous vehicle thereto. Each of these formulations may further comprise one or more of dispersing or wetting agent, a suspending agent, and a preservative. Additional excipients, such as fillers and sweetening, flavoring, or coloring agents, may also be included in these formulations.

Methods of Treating Diseases

Diseases, such as diabetes, may be treated by orally administering a composition of the invention wherein insulin is the associated therapeutic agent. Similarly, diabetes may be treated by orally administering a compound of the invention wherein insulin is the associated therapeutic and wherein another form of insulin is co-administered. Routes of co-administration include, but are not limited to, oral administration, intramuscular injection, inhalation, intravenous injection, intra-arterial injection, as well as any other form of administration.

Although a physician will be able to select the appropriate dose for a given patient, the range of doses that may be delivered in a given formulation of a compound of the invention is from about 1 to about 40 units, but may be 5, 10, 15, 20, 25, 30, or 35 units. A given formulation may, however, contain any whole or partial integer therebetween and may exceed 40 units.

Of course, diseases other than diabetes may be treated by orally administering a composition of the invention with a different associated therapeutic agent. A person of ordinary skill in the art, armed with the disclosure herein, will be able to select a given therapeutic agent, associate that therapeutic agent with the composition of the invention, and treat a disease or condition susceptible to treatment with the therapeutic agent.

Kits

The invention also includes a kit comprising a composition of the invention and an instructional material which describes administering the composition to a mammal. As used herein, an "instructional material" includes a publication, a recording, a diagram, or any other medium of expression which can be used to communicate the usefulness of the composition of the invention in the kit for effecting alleviation of the various diseases or disorders recited herein.

Optionally, or alternatively, the instructional material may describe one or more methods of alleviating the diseases or disorders in a cell or a tissue of a mammal. The instructional material of the kit may, for example, be affixed to a container which contains the invention or be shipped together with a container which contains the invention. Alternatively, the instructional material may be shipped separately from the container with the intention that the instructional material and the compound be used cooperatively by the recipient.

EXPERIMENTAL EXAMPLES

The invention is now described with reference to the following examples. These examples are provided for the purpose of illustration only and the invention should in no way be construed as being limited to these examples but rather should be construed to encompass any and all variations which become evident as a result of the teaching provided herein.

Experiment 1—Administration of Compositions not Containing a Targeting Agent

A composition prepared from a mixture of lipids including approximately 62 mole percent 1,2-distearoyl-sn-glycero-3-phosphocholine, approximately 22 mole percent dihexadecyl phosphate, approximately 16 mole percent cholesterol, and no targeting agent was prepared according to the microfluidization procedure generally described herein. A known portion of the lipid component comprised $^{14}C$ labeled phospholipid. Following filtration through a 0.2 micron filter, the average constituent size was less than 100 nm as measured with a Coulter Sub-micron Particle Size Analyzer.

Figure 2:
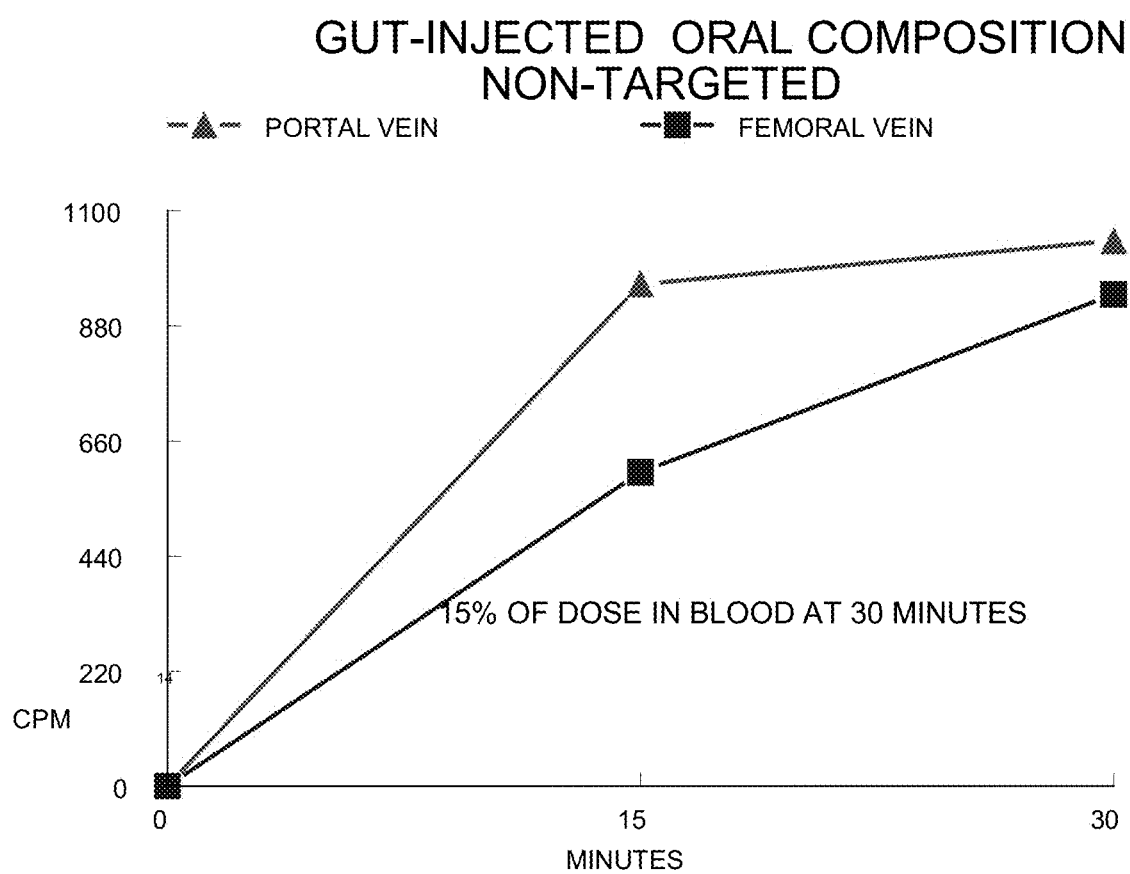
FIG. 2 is a graph depicting the counts of $^{14}C$ radio-labeled phospholipid found in the femoral and portal veins 15 and 30 minutes post injecting radio-labeled composition into the duodenum of a fasted and anesthetized 230 gram rat.
Figure 3:
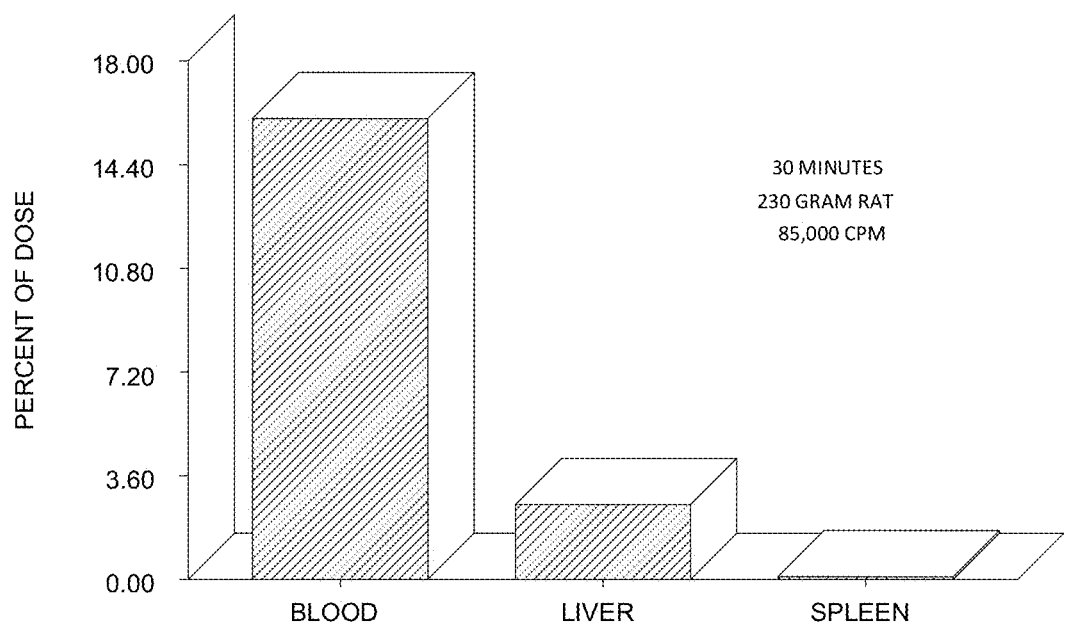
FIG. 3 is a bar graph depicting the distribution of $^{14}C$ radio-labeled phospholipid amongst the blood, liver, and spleen in the rats of FIG. 2, post-sacrifice.

A 10 mg/kg body weight sample of the composition (containing 85,000 cpm of $^{14}C$ radio-label) was then injected into the duodenum of an anesthetized 230 gram fasted, but otherwise normal, rat. Blood was taken from the portal and femoral veins at 15 and 30 minutes post-dosing for counting (FIG. 2). At 30 minutes post-dosing, the rat was sacrificed and representative samples of blood, liver, and spleen were removed for analysis (FIG. 3).

Labeled composition, as measured by $^{14}C$, was found in both portal and femoral blood of the rat. The portal blood levels of $^{14}C$ labeled composition was higher than the femoral blood levels (FIG. 2). At 30 minutes post-dosing, approximately 15% of the composition that was injected into the gut was found in the blood. Approximately 4% of the counts were found in the liver and about 1% were found in the spleen. Considering the relative sizes of the liver and spleen, the splenic uptake was much higher than liver uptake on a weight basis.

Experiment 2—Hepatocyte Targeting

Figure 4:
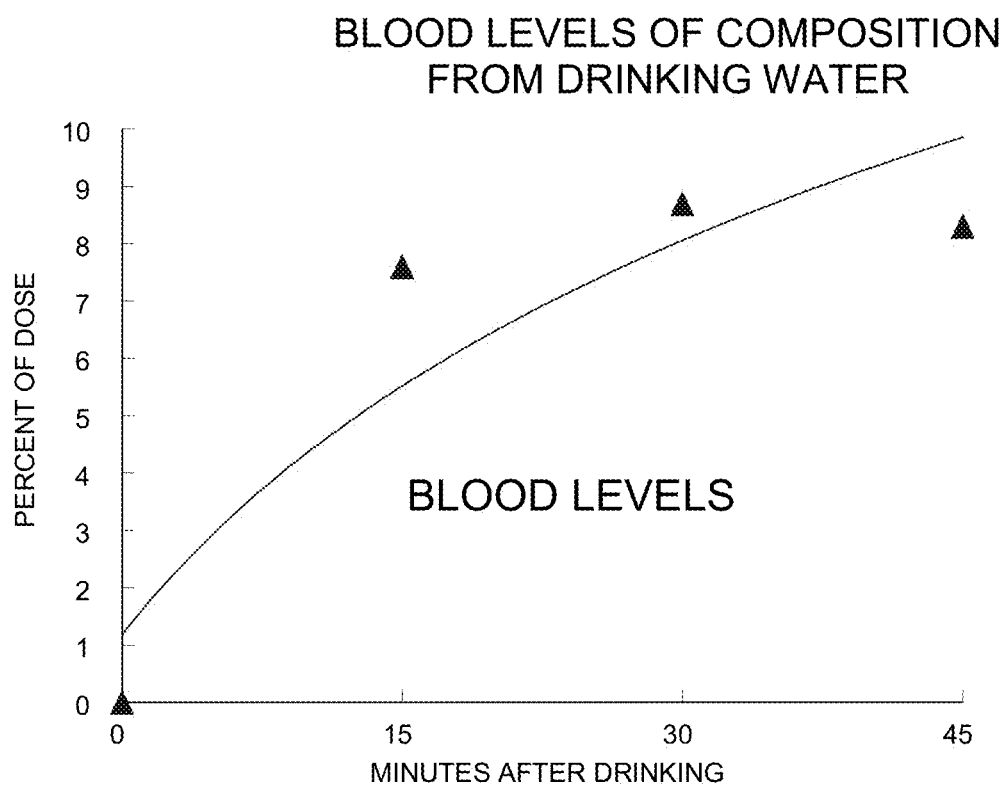
FIG. 4 is a graph depicting the absorption of radio-labeled composition from drinking water at 15, 30, and 45 minutes post-dosing.
Figure 5:
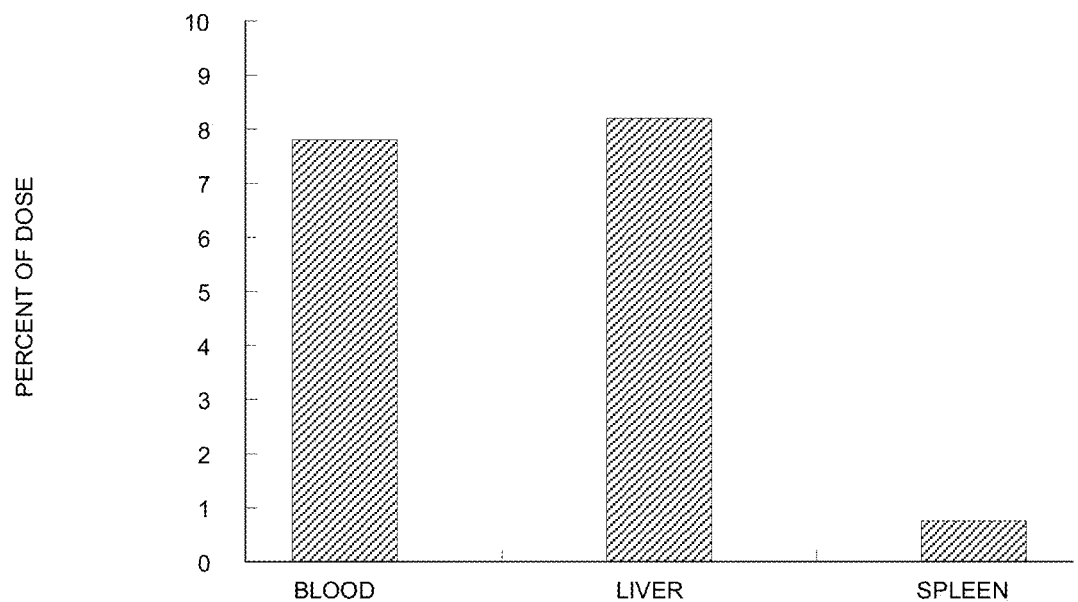
FIG. 5 is a bar graph depicting the distribution of the labeled composition amongst the blood, liver, and spleen in the rats of FIG. 4, post-sacrifice.

To demonstrate the absorption of the composition from the gut, a composition comprising insulin and approximately 61 mole percent 1,2 distearoyl-sn-glycero-3-phosphocholine, approximately 22 mole percent dihexadecyl phosphate, approximately 16 mole percent cholesterol, and approximately 1 mole percent poly[Cr-bis(N-2,6-diisopropylphenylcarbamoylmethyl iminodiacetic acid)] (wherein a known portion of the phospholipid component comprised $^{14}C$ labeled phospholipid) was prepared as recited in the general preparation disclosed herein. Prior to dosing the labeled composition to rats, the rats were fasted from food for 24 hours and from water for 4 hours. The fasted rats were then permitted to drink water from a graduated water bottle containing the composition. The drinking water bottle was removed from the cage after 15 minutes, the amount of water ingested from the drinking bottle was measured, and the amount of composition ingested was calculated. The rats' blood was sampled at 15, 30, and 45 minutes and the radiolabel in each sample was counted (FIG. 4). At 45 minutes the rats were sacrificed and the livers were counted for radio-label (FIG. 5).

As is shown in FIG. 4, approximately 8% of the ingested dose was found in the rats' blood 15 minutes after the water had been removed from the cage. The quantity in the rats' blood remained constant between 15 and 45 minutes. Liver uptake was approximately 8% at 45 minutes. Splenic uptake at 45 minutes was approximately 1% of the ingested dose (FIG. 5). The total absorption was approximately 17% (including blood, liver, and spleen).

Experiment 3—Hepatocyte Targeting with a Composition In Alloxan-Streptozotocin Treated Mice Mice used in the present experiment were made diabetic by administering streptozotocin and alloxan. The diabetic animals were then divided into two groups. The control group (11 mice) was orally dosed with regular insulin. The experimental group (7 mice) was orally dosed with a composition comprising insulin and approximately 61 mole percent 1,2 distearoyl-sn-glycero-3-phosphocholine, approximately 22 mole percent dihexadecyl phosphate, approximately 16 mole percent cholesterol, and approximately 1 mole percent poly[Cr-bis(N-2,6-diisopropylphenylcarbamoylmethyl iminodiacetic acid)] (wherein a known portion of the phospholipid component comprised $^{14}C$ labeled phospholipid). Dosing was accomplished utilizing the water bottle dosing method described in Experiment 2.

After being made diabetic, rats in both groups were treated identically over a 7 day period and fed with plain food and plain water. Following this 7 day period, rats in the control group were treated for an additional 7 day experimental period with food and regular insulin in the available drinking water at 0.1 U/ml. Over the same 7 day experimental period, the experimental group was fed regular food with the composition of the invention available in the drinking water at 0.1 U/ml. At the end of each 7-day period, blood glucose was measured in a tail-vein sample of blood by a Beckman Blood Glucose Analyzer.

Figure 6:
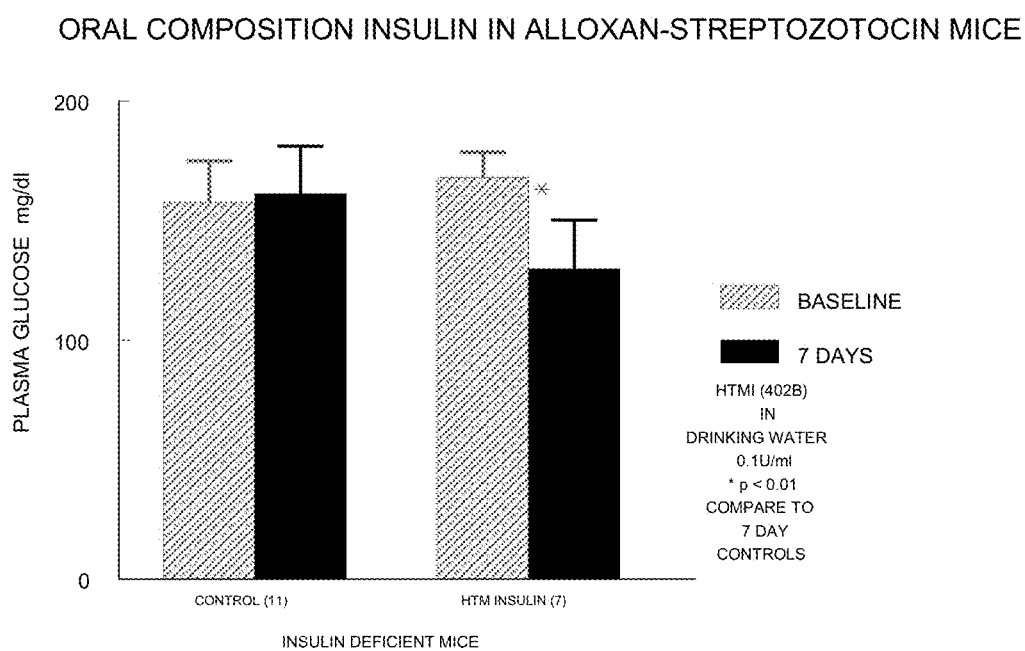
FIG. 6 is a graph depicting the efficacy of orally administered insulin in the form of a composition of the invention.

The pharmacologic efficacy of orally administered insulin in the group dosed with the above described composition is shown in FIG. 6. Mice receiving the composition had a statistically significant reduction in blood glucose on day seven (p<0.01) compared to mice receiving regular insulin, whose blood glucose was not altered at all.

Example 4—In Vivo Administration of Serotonin

Figure 7:
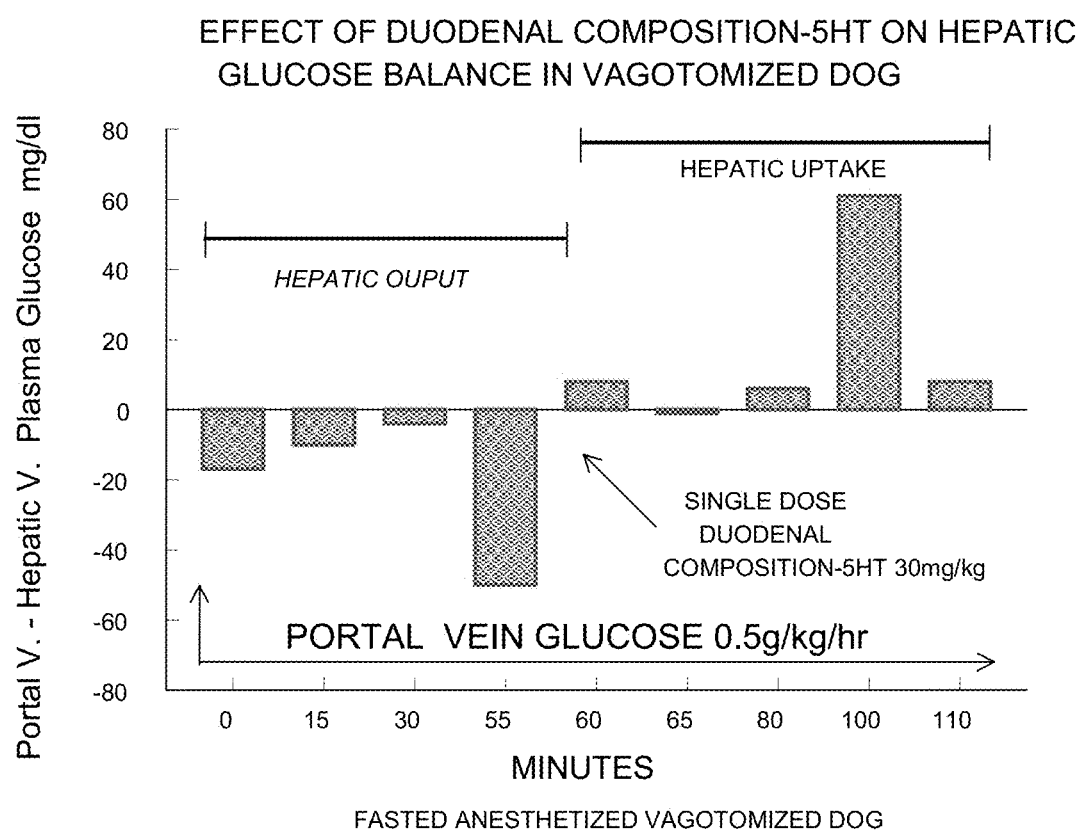
FIG. 7 is a bar graph depicting the efficacy of a composition of the invention (at low dosages), in converting a type 2 diabetic dog from hepatic glucose output to uptake during a portal glucose load.

The hepatic action of a composition comprising serotonin and approximately 61 mole percent 1,2 distearoyl-snglycero-3-phosphocholine, approximately 22 mole percent dihexadecyl phosphate, approximately 16 mole percent cholesterol, and 1 mole percent of poly[Cr-bis(N-2,6-diisopropylphenylcarbamoylmethyl iminodiacetic acid)] was demonstrated in a type 2 diabetic dog (truncal vagotomy). The dog was fasted, and then anesthetized. Blood sampling catheters were placed in the hepatic and portal veins to enable simultaneous blood sampling. Glucose was infused into the portal system at a rate of 0.5 g/kg/hour. Next, the above described composition was administered intraduodenally in a single dose of 30 µg/kg body weight. Results are depicted in FIG. 7 and demonstrate that serotonin (also referred to as 5-hydroxytryptamine or 5-HT), administered intraduodenally as a composition of the invention is effective at low doses in converting a type 2 diabetic dog from hepatic glucose output to uptake during a portal glucose load.

Example 5—In Vivo Administration of Calcitonin

Figure 8:
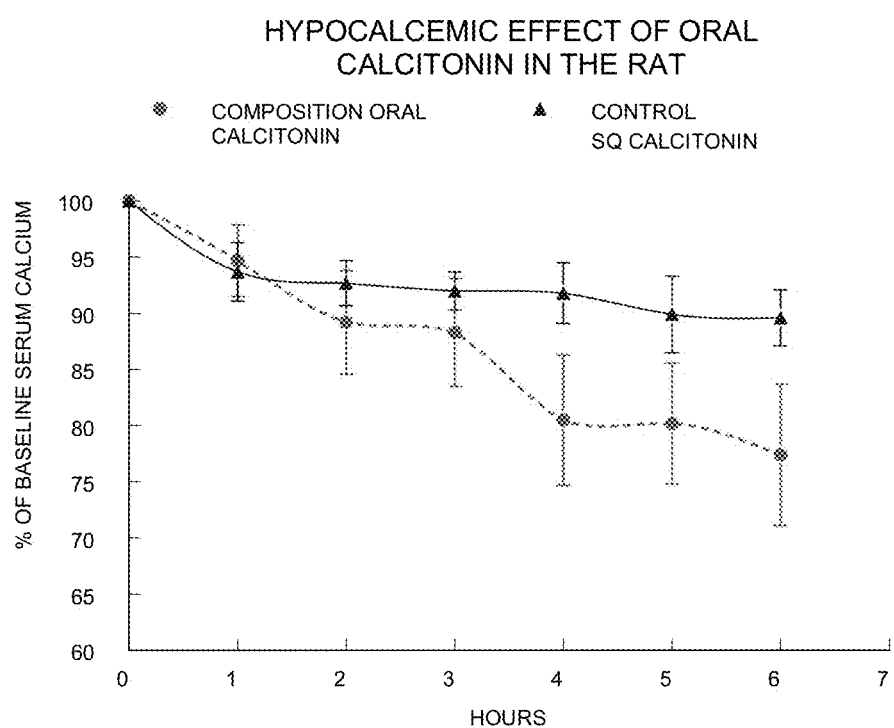
FIG. 8 is a plot of blood calcium levels after the administration of calcitonin associated with a non-targeted composition of the invention.

Normal, fasted, control rats were given a dose of salmon calcitonin via subcutaneous injection such that an initial 10% reduction in blood calcium was observed. Blood calcium levels were then measured for six hours post injection. An experimental group of rats was given the same effective dose of calcitonin by oral gavage, in the form of a composition comprising calcitonin and approximately 62 mole percent 1,2 distearoyl-sn-glycero-3-phosphocholine, approximately 22 mole percent dihexadecyl phosphate, and approximately 16 mole percent cholesterol. Blood calcium levels were followed for six hours (FIG. 8). A blood calcium reduction of up to 20% was observed in the non-control rats. This difference was statistically significant (FIG. 8).

Example 6—Clinical Trial with Targeted Insulin in Type 2 Diabetes Mellitus Subjects Capsules containing a composition of the invention were prepared. The composition comprised insulin as the therapeutic agent, gelatin, and approximately 61 mole percent 1,2 distearoyl-sn-glycero-3-phosphocholine, approximately 22 mole percent dihexadecyl phosphate, approximately 16 mole percent cholesterol, and about 1 mole percent of the sodium salt of Biotin-HDPE. Each capsule contained 2 U of insulin.

Six well characterized Type 2 diabetes patients participated in the controlled study. The patients were maintained on their customary Type 2 oral anti-diabetes therapy. Study participants were also given either placebo capsules or the above described capsules 30 minutes before a 60 gram carbohydrate meal at breakfast, lunch and dinner. Blood samples were drawn at frequent intervals over a 13 hour period and the Incremental Area Under the Curve for the blood glucose values was calculated for each subject.

Figure 10:
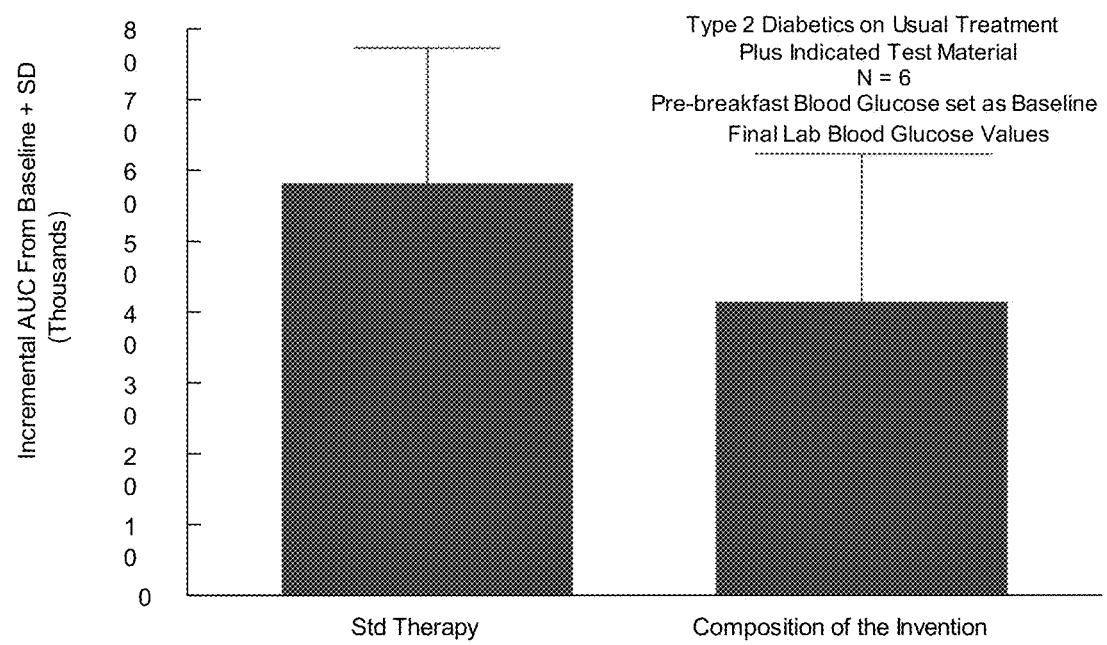
FIG. 10 is a graph of the efficacy of a composition of the invention comprising a biotin targeting agent and insulin at reducing the effects of type 2 diabetes in humans.

At 0.1 U/kg body weight/meal, the same dose that is frequently used with subcutaneous injection of insulin at a given meal, a statistically significant reduction in AUC for each of the three meals was observed. FIG. 10 depicts the results of the trial in graphical format.

Example 7—Insulin Concentration

Insulin U-500 contains 500 units of insulin/ml=0.5 units/1 µl
3.36 ml of U-500 insulin to 70 ml of constituent suspension in 18 mM phosphate buffer @ pH 7.01.
(3,360 µl)*(0.5 units of insulin/µl)=1,680 units of insulin total in 73.36 ml
(1,680 units of insulin)/(73.36 ml)=22.9 units of insulin/ml—or—34.35 units of insulin/1.5 ml
Load insulin for 21 hours;
Post loading, chromatograph 1.5 ml of sample over a 1.5 cm×25 cm column with Sepharose CL-6B gel equilibrated with 18 mM phosphate buffer @ pH 7.01
0% of free insulin recovered from column; The recovery of 0% of the total loaded insulin implies that 100% of the total "loaded" insulin is associated with a constituent of the composition.
34.35 units of insulin×100%=34.35 units of insulin bound or associated with the constituents of the invention.

Figure 11:
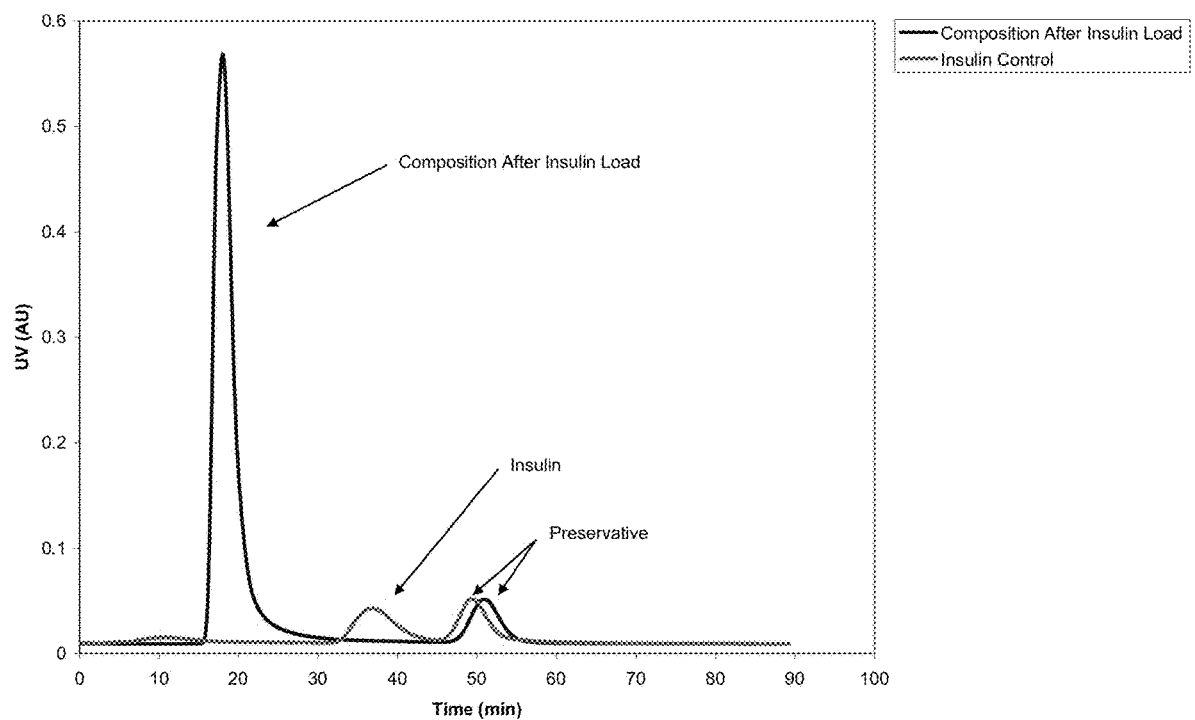
FIG. 11 is a chromatogram of a composition of the invention showing the efficacy of insulin loading.

FIG. 11 depicts the above described chromatography. A trace showing the elution time of free insulin is included for purposes of comparison. As can be seen from the chromatogram, insulin is associated with the constituents of the invention and no free insulin is in solution. A preservative included with insulin does not associate with the constituents of the composition of the invention and is visible in the chromatogram.

Example 8—Oral Delivery of GLP-1

Rats were fasted overnight. Subsequently, 800 mg each of alloxan and streptozotocin were dissolved in 40 mL of PBS (pH 7, 0.01M). The fasted rats were then treated immediately with a 0.5 mL IP dose to induce insulin deficiency. The animals were then stabilized overnight with water and food. Following stabilization, the rats were fasted overnight to deplete liver glycogen.

Subsequently, the rats were administered 1.5 g glucose/kg body weight and GLP-1 in the form of a GLP-1 associated with a composition comprising approximately 62 mole percent 1,2 distearoyl-sn-glycero-3-phosphocholine, approximately 22 mole percent dihexadecyl phosphate, and approximately 16 mole percent cholesterol ("associated GLP-1"). In separate experiments, the amount of associated GLP-1 was varied. Liver glycogen was measured chemically at 2 hours post dosing.

As a control, unassociated GLP-1 was gavaged in place of associated GLP-1. In a separate control, GLP-1, in a dose similar to that orally gavaged, was injected intraperitoneally. As is shown in Table 3, below, substantially enhanced oral efficacy was observed for the associated GLP-1 versus non-associated GLP-1.

TABLE 3

| Treatment | Dose GLP-1 mg/rat | Liver Glycogen mg/g liver |
| --- | --- | --- |
| Control Oral GLP-1 | 0.01 | 40 ± 22 |
| Intraperitoneal GLP-1 | 0.01 | 59 ± 44 |
| Oral Associated GLP-1 | 0.005 | 73 ± 56* |
| Oral Associated GLP-1 | 0.01 | 90 ± 75* |

*p = 0.05 compared to Control Oral GLP-1

Example 10—Oral Thyroxine

Thyroxine is known to lower blood cholesterol and triglyceride levels. However, at the doses required to treat high cholesterol and triglyceride, thyroxine causes hyperthyroidism as an unwanted side effect. The goal of this study was to demonstrate that orally administered targeted thyroxine associated with a compound of the invention would act at the liver with the result of lowering blood lipids without inducing the unwanted hyperthyroidism.

Normal laboratory mice, on high caloric diets, were administered low oral doses (0.2 to 1.0 μg) thyroxine in the form of a composition comprising thyroxine and constituents generated from a mixture of lipid components comprising approximately 61 mole percent 1,2 distearoyl-sn-glycero-3-phosphocholine, approximately 22 mole percent dihexadecyl phosphate, approximately 16 mole percent cholesterol, and approximately 1 mole percent of the sodium salt of Biotin-HDPE, a liver-targeting agent.

Figure 13:
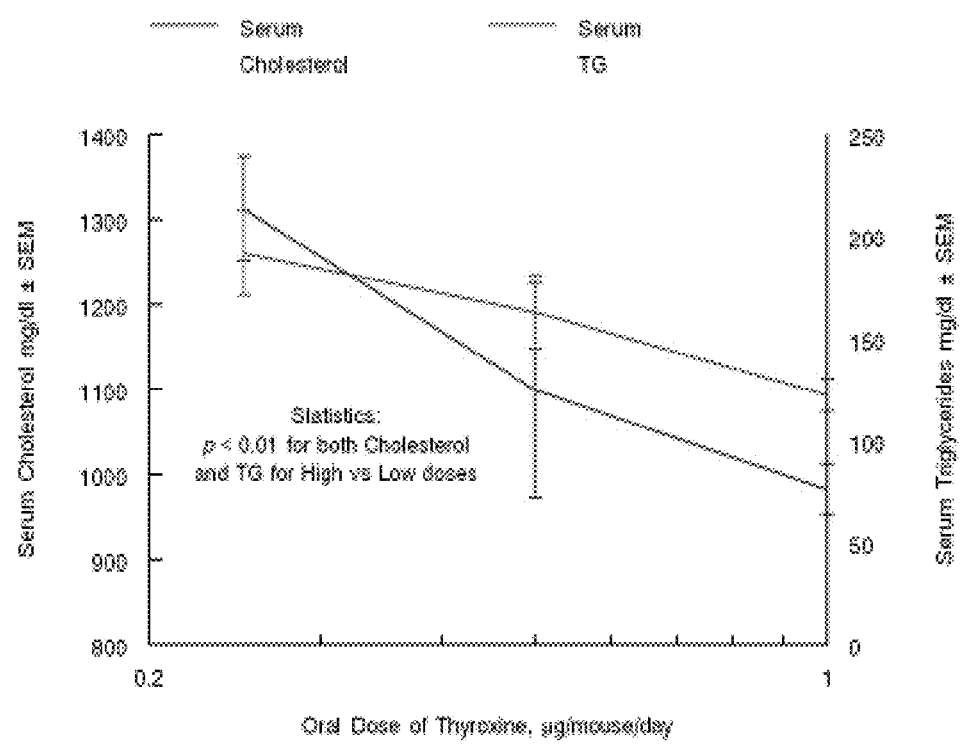
FIG. 13 is a graph depicting the effect of oral administration of thyroxine associated with a composition of the invention on serum cholesterol and triglycerides ("TG") in mice.

The mice, in groups of 4, were dosed daily by oral gavage for one week in a dose response study. Blood cholesterol and triglycerides were measured after one week treatment. Baseline values for cholesterol and triglycerides for all the groups were similar. The dose responses, shown in FIG. 13, demonstrates the efficacy of orally administered, hepatic targeted thyroxine associated with a composition of the invention. Blood levels of thyroid hormone did not increase with the dosing of hepatic targeted oral thyroxine, demonstrating the safety of the product.

Other published studies (Erion, M., et al., PNAS Sep. 25, 2007 vol 104, #39, pp 15490-15495) with hepatic targeted thyroxine analogs required doses at least 10 fold higher than those described herein to elicit similar reductions in blood cholesterol and triglycerides.

Example 11—Oral Interferon

A composition was prepared comprising interferon-α as the therapeutic agent and approximately 61 mole percent 1,2 distearoyl-sn-glycero-3-phosphocholine, approximately 22 mole percent dihexadecyl phosphate, approximately 16 mole percent cholesterol, and about 1 mole percent of the sodium salt of Biotin-HDPE.

Six patients with Hepatitis C, genotype 3, were treated with an aqueous suspension of the above described composition and Ribivirin daily for 8 weeks. The interferon-α dose in the aqueous suspension of the composition was 60,000 Units/day.

Figure 14:
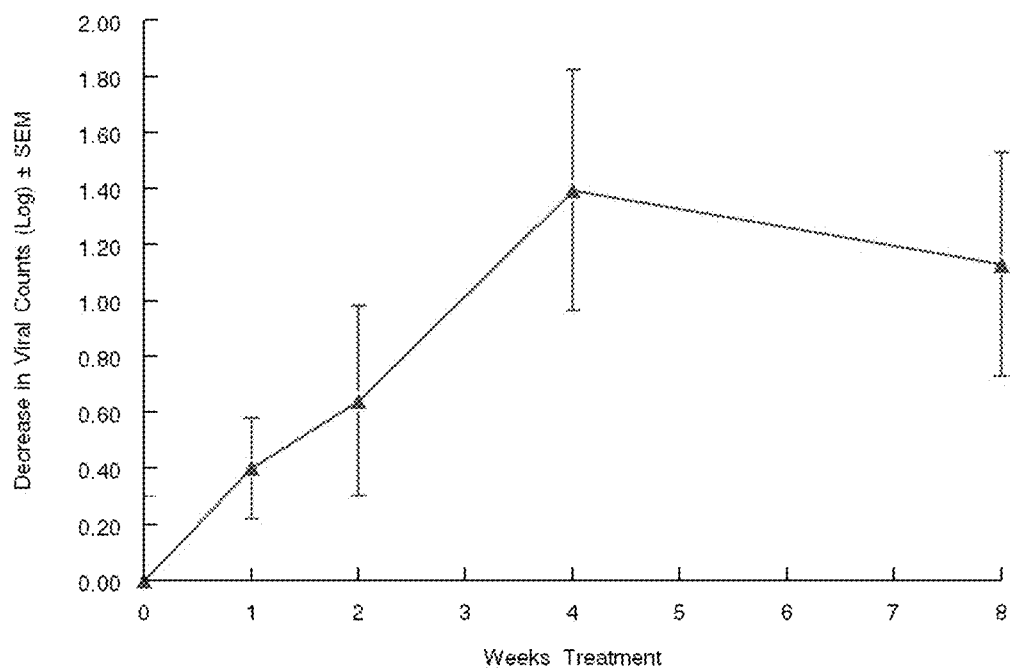
FIG. 14 is a graph depicting the effect of oral administration of interferon associated with a composition of the invention on reducing viral load in humans suffering from hepatitis-C.

Hepatitis C viral loads were measured at the beginning of the study, then at weeks 1, 2, 4, and 8. See FIG. 14. The data demonstrates the ability of the aqueous suspension of a composision of the invention to lower viral load with a minimal dose of interferon. Side effects were likewise minimized.

Example 12

In an example of a covalent interaction, IgG (human immunoglobulin, mixture of antibodies) was covalently linked to MPB-PE to form a IgG construct. IgG is an antibody that is not normally orally bioavailable. In this embodiment of the invention, the lipids selected to form the composition of the invention included approximately 68 mole percent 1,2-dipalmitoyl-sn-glycero-3-phosphocholine, approximately 19 mole percent dihexadecyl phosphate, approximately 10 mole percent cholesterol, and approximately 3 mol percent MPB-PE.

In order to form the composition of the invention, 1,2-dipalmitoyl-sn-glycero-3-phosphocholine, dihexadecyl phosphate, and cholesterol were microfluidized as set forth earlier herein to form constituents with an average size of between 50 and 60 nanometers. This suspension of constituents was then transferred to a round bottom flask that had been coated with a thin film of MPB-PE. The suspension was heated to about 62° C., with the temperature not falling below 60° C. or exceeding 65° C. The heated suspension was subsequently stirred for 15 minutes until all of the MPB-PE had been incorporated into the lipid construct.

Separately, IgG was reacted with a 10 fold excess of linker precursor XI to form XII, per Scheme III.

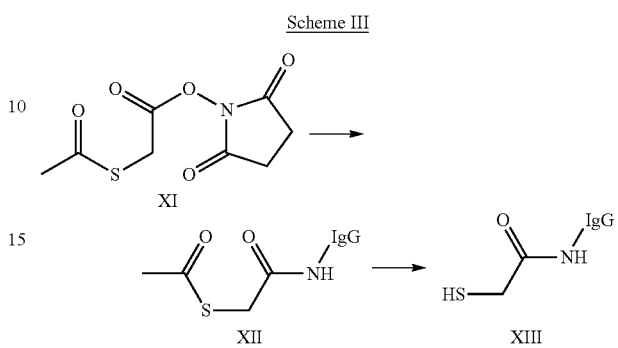

Scheme III

Compound XII was then purified using a 2.5×25 cm Sephadex G-25 column equilibrated with 18 mM phosphate buffer plus 1.0 mM EDTA buffer at pH 7.4. Next, the acetyl protecting group on compound XII was removed by stirring compound XII with 50 mM hydroxylamine hydrochloride in 18 mM sodium phosphate buffer containing 1.0 mM EDTA (pH 7.4) for 2 hours at ambient temperature. The resulting free thiol, XIII, was purified on 2.5×25 cm Sephadex G-25 column, as set forth for compound XII.

Immediately following purification, 200μ-moles of compound XIII was mixed with 10 ml of the composition prepared earlier. The reaction mixture was stirred for 15 minutes, during which time compound XIII underwent a Michael reaction with the maleimide functionality of the MBP-PE incorporated in the lipid construct. The conjugation reaction was stopped, and excess XIII removed, by the addition of a 50× molar excess of N-ethylmaleimide.

Although the above example was described with respect to IgG, it is equally applicable to any therapeutic agent with a nucleophilic nitrogen.

Example 13—Administration of Covalent Oral IgG

Human IgG antibodies were covalently attached to a constituent of the invention, as described in Example 12. Subsequently, eight 250 gram laboratory rats were prepared with intra-duodenal catheters for the administration of covalent IgG. After an overnight fast, 5 ug of covalent IgG was infused into the duodenal catheter. The catheter was subsequently washed with 0.5 ml buffer. Blood samples were taken at 15, 30, 60 and 120 minutes to assay the plasma concentration of human IgG antibodies by ELISA reaction.

In a control experiment, 5 ug of free IgG was infused into the duodenal catheter. The catheter was subsequently washed with 0.5 ml buffer. Blood samples were taken at 15, 30, 60 and 120 minutes to assay the plasma concentration of human IgG antibodies by ELISA reaction. The results of both studies are shown in FIG. 12.

Figure 12:
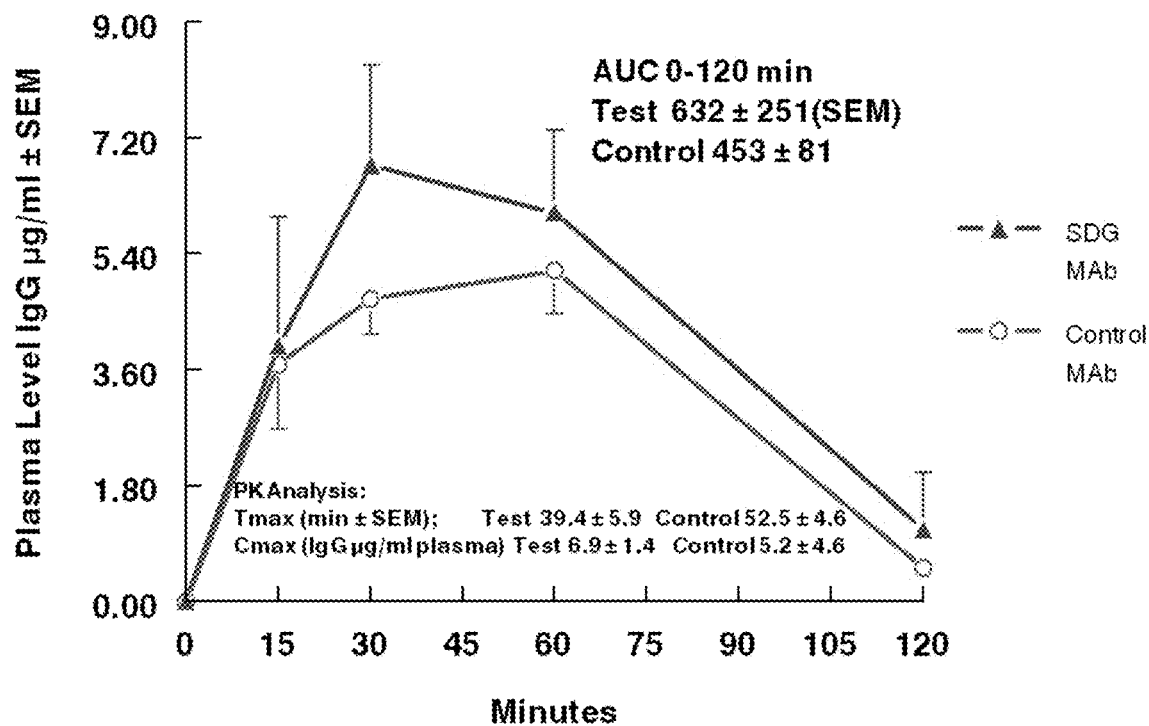
FIG. 12 is a graph depicting the efficacy of oral delivery of IgG antibodies covalently linked to a composition of the invention versus oral absorption of non-associated (free) IgG antibodies.

As can be seen in FIG. 12, covalent IgG provided enhanced plasma concentration of human IgG (AUC) as compared to free IgG. Likewise, covalent IgG enhanced T max—the time to maximum concentration, and C max—the maximum plasma concentration observed upon dosing. The enhanced efficacy of covalent IgG, as compared to free IgG, thus demonstrates the ability of a compound of the invention to enhance oral absorption of very large proteins into the systemic circulation.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An orally bioavailable composition comprising constituents comprising
1,2-distearoyl-sn-glycero-3-phosphocholine;
cholesterol;
dihexadecyl phosphate;
and at least one additional lipid selected from the group consisting of MCC-PE (1,2-Dipalmitoyl-sn-glycero-3-phosphoethanolamine-N-[4-(p-maleimidomethyl)cyclohexane-carboxamide]) and MPB-PE (1,2-Dipalmitoyl-sn-glycero-3-phosphoethanolamine-N-[4-(p-maleimido) phenylbutyrate]);
wherein said 1,2-distearoyl-sn-glycero-3-phosphocholine, said dihexadecyl phosphate, and said cholesterol are present in said constituents in a ratio of 62 mole %:22 mole %:16 mole %;
wherein said composition further comprises at least one polypeptide therapeutic or diagnostic agent;
wherein said at least one therapeutic or diagnostic agent is covalently bound to said at least one additional lipid through a linker of formula —C(=O)—(CH$_2$)$_n$S—, wherein n is an integer ranging from 1 to 10, wherein the carbonyl group of said linker is covalently bound to said at least one therapeutic or diagnostic agent, wherein the sulfur atom of said linker is covalently bound to said at least one additional lipid,
wherein a percentage ranging from 5% to 50% of said constituents exhibits an average diameter equal to or lower than 20 nm; and
wherein said composition is orally bioavailable in a mammal.

2. The composition of claim 1, wherein said linker is derived from a linker precursor of formula succinimidyl-O—C(=O)—(CH$_2$)$_n$SR, wherein R is a thiol-protecting group.

3. The composition of claim 1, wherein said therapeutic agent is selected from the group consisting of insulin, interferon, erythropoietin, parathyroid hormone, calcitonin, rituximab, trastuzumab, uricase, tissue plasminogen activator, thymoglobin, a vaccine, antithrombin III, filgrastin, pramilitide acetate, exanatide, epifibatide, antivenins, IgG, IgM, HGH, GLP-1, blood clotting Factors VII and VIII, IX, X, and a monoclonal antibody.

4. The composition of claim 1, wherein at least 25% of the cholesterol is thiocholesterol.

5. A method of preparing an orally bioavailable composition comprising constituents comprising 1,2-distearoyl-sn-glycero-3-phosphocholine; cholesterol; dihexadecyl phosphate; and at least one additional lipid selected from the group consisting of MCC-PE and MPB-PE;
the composition further comprising at least one polypeptide therapeutic or diagnostic agent; wherein said at least one therapeutic or diagnostic agent is covalently bound to said at least one additional lipid through a linker of formula —C(=O)—(CH$_2$)$_n$S—, wherein n is an integer ranging from 1 to 10, wherein the carbonyl group of said linker is covalently bound to said at least one therapeutic or diagnostic agent, and wherein the sulfur atom of said linker is covalently bound to said at least one additional lipid, wherein a percentage ranging from 5% to 50% of said constituents exhibits an average diameter equal to or lower than 20 nm and wherein said composition is orally bioavailable in a mammal,
said method comprising:
mixing 1,2-distearoyl-sn-glycero-3-phosphocholine, cholesterol, dihexadecyl phosphate and said at least one additional lipid to form a mixture of lipid-based constituents,
wherein said 1,2-distearoyl-sn-glycero-3-phosphocholine, said dihexadecyl phosphate, and said cholesterol are present in said mixture in a ratio of 62 mole %:22 mole %:16 mole %;
reacting a therapeutic agent with a linker precursor of formula succinimidyl-O—C(=O)—(CH$_2$)$_n$SR, wherein R is a thiol-protecting group and n is an integer ranging from 1 to 10, thus forming a therapeutic agent/linker conjugate wherein the carbonyl group of said linker precursor is covalently bound to said at least one therapeutic or diagnostic agent;
deprotecting said R group in said conjugate to form a deprotected conjugate comprising a thiol; and
contacting said deprotected conjugate comprising a thiol with said mixture of lipid-based constituents to form said composition.

6. The composition of claim 1, further comprising a targeting agent selected from the group consisting of biotin-DHPE (2,3-diacetoxypropyl 2-(5-((3aS,6aR)-2-oxohexahydro-1H-thieno[3,4-d]imidazol-4-yl) pentanamido)ethyl phosphate) and biotin-X-DHPE (2,3-diacetoxypropyl 2-(6-(5-((3aS,6aR)-2-oxohexahydro-1H-thieno[3,4-d]imidazol-4-yl)pentanamido)hexanamido)ethyl phosphate).

7. The composition of claim 1, further comprising a reticuloendothelial system (RES) avoidance molecule.

8. The method of claim 5, wherein the composition further comprises a targeting agent selected from the group consisting of biotin-DHPE (2,3-diacetoxypropyl 2-(5-((3aS,6aR)-2-oxohexahydro-1H-thieno[3,4-d]imidazol-4-yl)pentanamido)ethyl phosphate) and biotin-X-DHPE (2,3-diacetoxypropyl 2-(6-(5-((3aS,6aR)-2-oxohexahydro-1H-thieno[3,4-d]imidazol-4-yl)pentanamido)hexanamido)ethyl phosphate).

9. The method of claim 5, wherein the composition further comprises a reticuloendothelial system (RES) avoidance molecule.

* * * * *